(12) United States Patent
Bush, Jr.

(10) Patent No.: US 11,166,709 B2
(45) Date of Patent: Nov. 9, 2021

(54) INSTRUMENTATION AND METHODS FOR THE IMPLANTATION OF SPINAL IMPLANTS

(71) Applicant: Stryker European Operations Holdings LLC, Kalamazoo, MI (US)

(72) Inventor: Charles L. Bush, Jr., Wayne, NJ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 83 days.

(21) Appl. No.: 16/327,672

(22) PCT Filed: Aug. 22, 2017

(86) PCT No.: PCT/US2017/048009
§ 371 (c)(1),
(2) Date: Feb. 22, 2019

(87) PCT Pub. No.: WO2018/039228
PCT Pub. Date: Mar. 1, 2018

(65) Prior Publication Data
US 2019/0192131 A1    Jun. 27, 2019

Related U.S. Application Data

(60) Provisional application No. 62/470,534, filed on Mar. 13, 2017, provisional application No. 62/378,485, filed on Aug. 23, 2016.

(51) Int. Cl.
*A61B 17/02* (2006.01)
(52) U.S. Cl.
CPC ........ *A61B 17/025* (2013.01); *A61B 17/0206* (2013.01); *A61B 2017/0256* (2013.01)
(58) Field of Classification Search
CPC .......... A61B 2017/0256; A61B 17/025; A61B 17/0206
See application file for complete search history.

(56) References Cited

U.S. PATENT DOCUMENTS

| 380,745 | A | * | 4/1888 | Chamberlin | ............. | A61B 1/32 |
| | | | | | | 600/224 |
| 447,761 | A | | 3/1891 | Clough | | |

(Continued)

FOREIGN PATENT DOCUMENTS

| FR | 2807313 A1 | 10/2001 |
| WO | 9609013 A1 | 3/1996 |

(Continued)

OTHER PUBLICATIONS

International Search Report for Application No. PCT/US2017/048009 dated Dec. 11, 2017, 7 pages.

(Continued)

*Primary Examiner* — Julianna N Harvey
(74) *Attorney, Agent, or Firm* — Lerner, David, Littenberg, Krumholz & Mentlik, LLP

(57) ABSTRACT

The present invention relates to systems and methods for accessing the spine to place implants. In one embodiment, a system includes an adjustable rod structure having four rods radially surrounding a probe, a ring and a retractor. The adjustable rod structure is configured to have a closed and open profile controlled by the retractor such that the open profile creates a space between rods of the structure. The ring is configured to be placed within retracted rods to maintain the open profile after retraction. In a method embodiment, the adjustable rod structure is inserted through a percutaneous incision in the closed position until it reaches a target site. The retractor is then attached to the rods and used to retract the rods. The probe is then removed from within an opening created and a ring is advanced into the opening to hold the rods in place.

19 Claims, 27 Drawing Sheets

(56) References Cited

U.S. PATENT DOCUMENTS

| | | |
|---|---|---|
| 832,201 A | 10/1906 | Fistler |
| 1,157,202 A | 10/1915 | Bates et al. |
| 1,428,653 A | 9/1922 | Nick |
| 1,618,261 A | 2/1927 | Arbogast |
| 1,827,497 A | 10/1931 | Varney |
| 1,839,726 A | 1/1932 | Arnold |
| 1,863,057 A | 6/1932 | Innes |
| 1,944,009 A | 1/1934 | Homer |
| 2,313,164 A | 3/1943 | Nelson |
| 2,586,488 A | 2/1952 | Smith |
| 2,812,758 A | 11/1957 | Blumenschein |
| 2,854,983 A | 10/1958 | Baskin |
| 3,070,088 A | 12/1962 | Brahos |
| 3,087,486 A | 4/1963 | Kilpatrick |
| 3,221,743 A | 12/1965 | Thompson et al. |
| 3,394,700 A | 7/1968 | Yamamoto |
| 3,397,699 A | 8/1968 | Kohl |
| 3,417,746 A | 12/1968 | Moore et al. |
| 3,509,883 A | 5/1970 | Dibelius |
| 3,522,799 A | 8/1970 | Gauthier |
| 3,731,673 A | 5/1973 | Halloran |
| 3,749,088 A | 7/1973 | Kohlmann |
| 3,770,342 A | 11/1973 | Dudragne |
| 3,782,370 A | 1/1974 | McDonald |
| 3,788,318 A | 1/1974 | Kim et al. |
| 3,789,852 A | 2/1974 | Kim et al. |
| 3,796,214 A | 3/1974 | Davis |
| 3,807,393 A | 4/1974 | McDonald |
| 3,944,341 A | 3/1976 | Pomerantzeff |
| 3,965,890 A | 6/1976 | Gauthier |
| 3,998,217 A | 12/1976 | Trumbull et al. |
| 4,010,741 A | 3/1977 | Gauthier |
| 4,130,113 A | 12/1978 | Graham |
| 4,141,364 A | 2/1979 | Schultze |
| 4,226,228 A | 10/1980 | Shin et al. |
| 4,254,763 A | 3/1981 | McCready et al. |
| 4,312,353 A | 1/1982 | Shahbabian |
| 4,337,763 A | 7/1982 | Petrassevich |
| 4,545,374 A | 10/1985 | Jacobson |
| 4,589,868 A | 5/1986 | Dretler |
| 4,616,635 A | 10/1986 | Caspar et al. |
| 4,617,916 A | 10/1986 | LeVahn et al. |
| 4,716,901 A | 1/1988 | Jackson et al. |
| 4,718,151 A | 1/1988 | LeVahn et al. |
| 4,739,762 A | 4/1988 | Palmaz |
| 4,779,611 A | 10/1988 | Grooters et al. |
| 4,813,401 A | 3/1989 | Grieshaber |
| 4,817,587 A | 4/1989 | Janese |
| 4,896,669 A | 1/1990 | Bhate et al. |
| 4,949,707 A | 8/1990 | LeVahn et al. |
| 4,971,037 A | 11/1990 | Pelta |
| 4,971,038 A | 11/1990 | Farley |
| 5,032,113 A | 7/1991 | Burns |
| 5,052,373 A | 10/1991 | Michelson |
| 5,092,314 A | 3/1992 | Zeitels |
| 5,116,318 A | 5/1992 | Hillstead |
| 5,139,511 A | 8/1992 | Gill et al. |
| 5,183,464 A | 2/1993 | Dubrul et al. |
| 5,312,417 A | 5/1994 | Wilk |
| 5,320,611 A | 6/1994 | Bonutti et al. |
| 5,351,679 A | 10/1994 | Mayzels et al. |
| 5,377,667 A | 1/1995 | Patton et al. |
| 5,383,889 A | 1/1995 | Warner et al. |
| 5,391,156 A | 2/1995 | Hildwein et al. |
| 5,391,178 A | 2/1995 | Yapor |
| 5,425,730 A | 6/1995 | Luloh |
| 5,431,676 A | 7/1995 | Dubrul et al. |
| 5,452,732 A | 9/1995 | Bircoll |
| 5,460,170 A | 10/1995 | Hammerslag |
| 5,474,057 A | 12/1995 | Makower et al. |
| 5,496,345 A | 3/1996 | Kieturakis et al. |
| 5,505,690 A | 4/1996 | Patton et al. |
| 5,512,038 A | 4/1996 | O'Neal et al. |
| 5,514,153 A | 5/1996 | Bonutti |
| 5,520,611 A | 5/1996 | Rao et al. |
| 5,522,790 A | 6/1996 | Moll et al. |
| 5,580,344 A | 12/1996 | Hasson |
| 5,607,441 A | 3/1997 | Sierocuk et al. |
| 5,653,726 A | 8/1997 | Kieturakis |
| 5,678,572 A | 10/1997 | Shaw et al. |
| 5,685,826 A | 11/1997 | Bonutti |
| 5,688,223 A | 11/1997 | Rosendahl |
| 5,702,417 A | 12/1997 | Hermann |
| 5,707,362 A | 1/1998 | Yoon |
| 5,728,046 A | 3/1998 | Mayer et al. |
| 5,755,661 A | 5/1998 | Schwartzman |
| 5,772,661 A | 6/1998 | Michelson |
| 5,772,681 A | 6/1998 | Leoni |
| 5,782,854 A | 7/1998 | Hermann |
| 5,827,318 A | 10/1998 | Bonutti |
| 5,827,319 A | 10/1998 | Carlson et al. |
| 5,830,191 A | 11/1998 | Hildwein et al. |
| 5,860,997 A | 1/1999 | Bonutti |
| 5,865,802 A | 2/1999 | Yoon et al. |
| 5,888,196 A | 3/1999 | Bonutti |
| 5,888,197 A | 3/1999 | Mulac et al. |
| 5,893,866 A | 4/1999 | Hermann et al. |
| 5,897,087 A | 4/1999 | Farley |
| 5,916,151 A | 6/1999 | Charters |
| 5,919,128 A | 7/1999 | Fitch |
| 5,928,139 A * | 7/1999 | Koros ............... A61B 17/0206 600/205 |
| 5,941,777 A | 8/1999 | Moser et al. |
| 5,944,658 A | 8/1999 | Koros et al. |
| 5,944,734 A | 8/1999 | Hermann et al. |
| 5,954,739 A | 9/1999 | Bonutti |
| 5,957,832 A | 9/1999 | Taylor et al. |
| 5,961,499 A | 10/1999 | Bonutti et al. |
| 5,967,970 A | 10/1999 | Cowan et al. |
| 5,993,472 A | 11/1999 | Hermann et al. |
| 6,004,337 A | 12/1999 | Kieturakis et al. |
| 6,004,340 A | 12/1999 | Hermann et al. |
| 6,022,340 A | 2/2000 | Sepetka et al. |
| 6,027,518 A | 2/2000 | Gaber |
| 6,032,671 A | 3/2000 | Mollenauer et al. |
| 6,036,689 A | 3/2000 | Tu et al. |
| 6,074,343 A | 6/2000 | Nathanson et al. |
| 6,079,761 A | 6/2000 | Sadeck |
| 6,080,174 A | 6/2000 | Dubrul et al. |
| 6,083,154 A | 7/2000 | Liu et al. |
| 6,093,173 A | 7/2000 | Balceta et al. |
| 6,102,928 A | 8/2000 | Bonutti |
| 6,139,493 A | 10/2000 | Koros et al. |
| 6,171,299 B1 | 1/2001 | Bonutti |
| 6,187,023 B1 | 2/2001 | Bonutti |
| 6,206,826 B1 | 3/2001 | Mathews et al. |
| 6,206,886 B1 | 3/2001 | Bennett |
| 6,234,961 B1 | 5/2001 | Gray |
| 6,235,043 B1 | 5/2001 | Reiley et al. |
| 6,258,089 B1 | 7/2001 | Campbell et al. |
| 6,267,424 B1 | 7/2001 | Gillette |
| 6,277,136 B1 | 8/2001 | Bonutti |
| 6,312,443 B1 | 11/2001 | Stone |
| 6,322,500 B1 | 11/2001 | Sikora et al. |
| 6,325,812 B1 | 12/2001 | Dubrul et al. |
| 6,338,730 B1 | 1/2002 | Bonutti et al. |
| 6,354,995 B1 | 3/2002 | Hoftman et al. |
| 6,387,095 B1 | 5/2002 | Kennett et al. |
| 6,431,025 B1 | 8/2002 | Koros et al. |
| 6,436,119 B1 | 8/2002 | Erb et al. |
| 6,464,634 B1 | 10/2002 | Fraser |
| 6,464,697 B1 | 10/2002 | Edwards et al. |
| 6,466,817 B1 | 10/2002 | Kaula et al. |
| 6,468,205 B1 | 10/2002 | Mollenauer et al. |
| 6,494,893 B2 | 12/2002 | Dubrul et al. |
| 6,511,423 B2 | 1/2003 | Farley |
| 6,564,078 B1 | 5/2003 | Marino et al. |
| 6,569,182 B1 | 5/2003 | Balceta et al. |
| 6,592,602 B1 | 7/2003 | Peartree et al. |
| 6,602,190 B2 | 8/2003 | Dobrovolny |
| 6,616,605 B2 | 9/2003 | Wright et al. |
| 6,632,234 B2 | 10/2003 | Kieturakis et al. |
| 6,632,235 B2 | 10/2003 | Weikel et al. |
| 6,689,152 B2 | 2/2004 | Balceta et al. |

(56) References Cited

U.S. PATENT DOCUMENTS

| | | |
|---|---|---|
| 6,692,462 B2 | 2/2004 | Mackenzie et al. |
| 6,760,616 B2 | 7/2004 | Hoey et al. |
| 6,814,715 B2 | 11/2004 | Bonutti et al. |
| 6,846,287 B2 | 1/2005 | Bonadio et al. |
| 6,849,064 B2 | 2/2005 | Hamada |
| 6,866,676 B2 | 3/2005 | Kieturakis et al. |
| 6,869,398 B2 | 3/2005 | Obenchain et al. |
| 6,921,364 B2 | 7/2005 | Mollenauer et al. |
| 6,945,933 B2 | 9/2005 | Branch et al. |
| 6,948,751 B2 | 9/2005 | Wooten et al. |
| 7,050,848 B2 | 5/2006 | Hoey et al. |
| 7,056,321 B2 | 6/2006 | Pagliuca et al. |
| 7,079,883 B2 | 7/2006 | Marino et al. |
| 7,144,368 B2 | 12/2006 | Larson et al. |
| 7,150,714 B2 | 12/2006 | Myles |
| 7,177,677 B2 | 2/2007 | Kaula et al. |
| 7,195,592 B2 | 3/2007 | Ravikumar et al. |
| 7,207,949 B2 | 4/2007 | Miles et al. |
| 7,211,098 B2 | 5/2007 | Dallara et al. |
| 7,217,273 B2 | 5/2007 | Bonutti |
| 7,223,233 B2 | 5/2007 | Branch et al. |
| 7,235,064 B2 | 6/2007 | Hopper et al. |
| 7,261,688 B2 | 8/2007 | Smith et al. |
| 7,294,136 B2 | 11/2007 | Dubrul et al. |
| 7,311,719 B2 | 12/2007 | Bonutti |
| 7,326,226 B2 | 2/2008 | Root et al. |
| 7,329,268 B2 | 2/2008 | Van Nguyen et al. |
| 7,344,495 B2 | 3/2008 | Ravikumar et al. |
| 7,374,534 B2 | 5/2008 | Dalton |
| 7,390,298 B2 | 6/2008 | Chu |
| 7,396,329 B2 | 7/2008 | Nakao |
| 7,407,483 B2 | 8/2008 | Perez-Cruet et al. |
| 7,435,219 B2 | 10/2008 | Kim |
| 7,455,639 B2 | 11/2008 | Ritland |
| 7,458,933 B2 | 12/2008 | LeVahn et al. |
| 7,470,236 B1 | 12/2008 | Kelleher et al. |
| 7,473,222 B2 | 1/2009 | Dewey et al. |
| 7,476,232 B2 | 1/2009 | Deal |
| 7,488,337 B2 | 2/2009 | Saab et al. |
| 7,491,168 B2 | 2/2009 | Raymond et al. |
| 7,510,524 B2 | 3/2009 | Vayser et al. |
| 7,513,869 B2 | 4/2009 | Branch et al. |
| 7,522,953 B2 | 4/2009 | Kaula et al. |
| 7,556,600 B2 | 7/2009 | Landry et al. |
| 7,582,058 B1 | 9/2009 | Miles et al. |
| 7,594,888 B2 | 9/2009 | Raymond et al. |
| 7,641,664 B2 | 1/2010 | Pagano |
| 7,645,232 B2 | 1/2010 | Shluzas |
| 7,682,378 B2 | 3/2010 | Truckai et al. |
| 7,683,565 B2 | 3/2010 | Quaid et al. |
| 7,686,492 B2 | 3/2010 | Vayser et al. |
| 7,691,057 B2 | 4/2010 | Miles et al. |
| 7,691,657 B2 | 4/2010 | Lee |
| 7,693,562 B2 | 4/2010 | Marino et al. |
| 7,704,267 B2 | 4/2010 | Tessmer |
| 7,744,612 B2 | 6/2010 | Blain |
| 7,747,311 B2 | 6/2010 | Quaid, III |
| 7,758,501 B2 | 7/2010 | Frasier et al. |
| 7,780,594 B2 | 8/2010 | Hutton |
| 7,785,253 B1 | 8/2010 | Arambula et al. |
| 7,811,230 B2 | 10/2010 | Hsueh et al. |
| 7,819,801 B2 | 10/2010 | Miles et al. |
| 7,850,608 B2 | 12/2010 | Hamada |
| 7,874,982 B2 | 1/2011 | Selover et al. |
| 7,883,522 B2 | 2/2011 | Hamada |
| 7,887,482 B2 | 2/2011 | Hamada |
| 7,891,801 B2 | 2/2011 | Nakajima |
| 7,892,173 B2 | 2/2011 | Miles et al. |
| 7,905,840 B2 | 3/2011 | Pimenta et al. |
| 7,909,761 B2 | 3/2011 | Banchieri et al. |
| 7,909,832 B2 | 3/2011 | Michelson |
| 7,918,891 B1 | 4/2011 | Curran et al. |
| 7,920,922 B2 | 4/2011 | Gharib et al. |
| 7,931,589 B2 | 4/2011 | Cohen et al. |
| 7,935,051 B2 | 5/2011 | Miles et al. |
| 7,935,053 B2 | 5/2011 | Karpowicz et al. |
| 7,946,982 B2 | 5/2011 | Hamada |
| 7,962,191 B2 | 6/2011 | Marino et al. |
| 7,963,927 B2 | 6/2011 | Kelleher et al. |
| 7,976,463 B2 | 7/2011 | Dewey et al. |
| 7,981,029 B2 | 7/2011 | Branch et al. |
| 7,985,179 B2 | 7/2011 | Gephart et al. |
| 7,988,623 B2 | 8/2011 | Pagliuca et al. |
| 7,988,624 B2 | 8/2011 | Smith et al. |
| 7,991,463 B2 | 8/2011 | Kelleher et al. |
| 8,000,782 B2 | 8/2011 | Gharib et al. |
| 8,005,535 B2 | 8/2011 | Gharib et al. |
| 8,010,180 B2 | 8/2011 | Quaid et al. |
| 8,016,767 B2 | 9/2011 | Miles et al. |
| 8,027,716 B2 | 9/2011 | Gharib et al. |
| 8,050,769 B2 | 11/2011 | Gharib et al. |
| 8,055,349 B2 | 11/2011 | Gharib et al. |
| 8,062,217 B2 | 11/2011 | Boucher et al. |
| 8,062,303 B2 | 11/2011 | Berry et al. |
| 8,068,912 B2 | 11/2011 | Kaula et al. |
| D652,519 S | 1/2012 | Miles et al. |
| D652,921 S | 1/2012 | Miles et al. |
| D652,922 S | 1/2012 | Miles et al. |
| 8,090,436 B2 | 1/2012 | Hoey et al. |
| 8,095,200 B2 | 1/2012 | Quaid, III |
| 8,105,236 B2 | 1/2012 | Malandain et al. |
| 8,114,019 B2 | 2/2012 | Miles et al. |
| 8,114,161 B2 | 2/2012 | Evans et al. |
| 8,114,689 B2 | 2/2012 | Kang et al. |
| 8,133,173 B2 | 3/2012 | Miles et al. |
| 8,137,284 B2 | 3/2012 | Miles et al. |
| 8,152,721 B2 | 4/2012 | Michaeli et al. |
| 8,157,728 B2 | 4/2012 | Danna et al. |
| 8,165,653 B2 | 4/2012 | Marino et al. |
| 8,172,750 B2 | 5/2012 | Miles et al. |
| 8,182,423 B2 | 5/2012 | Miles et al. |
| 8,187,179 B2 | 5/2012 | Miles et al. |
| 8,187,334 B2 | 5/2012 | Curran et al. |
| 8,192,356 B2 | 6/2012 | Miles et al. |
| 8,192,357 B2 | 6/2012 | Miles et al. |
| 8,206,293 B2 | 6/2012 | Reglos et al. |
| D666,292 S | 8/2012 | Miles et al. |
| D666,293 S | 8/2012 | Miles et al. |
| D666,294 S | 8/2012 | Miles et al. |
| 8,244,343 B2 | 8/2012 | Gharib et al. |
| 8,246,686 B1 | 8/2012 | Curran et al. |
| 8,265,744 B2 | 9/2012 | Gharib et al. |
| 8,287,522 B2 | 10/2012 | Moses et al. |
| 8,298,139 B2 | 10/2012 | Hamada |
| 8,303,498 B2 | 11/2012 | Miles et al. |
| 8,303,499 B2 | 11/2012 | Hamada |
| 8,303,515 B2 | 11/2012 | Miles et al. |
| 8,317,693 B2 | 11/2012 | Grey et al. |
| 8,323,185 B2 | 12/2012 | Perez-Cruet et al. |
| 8,337,410 B2 | 12/2012 | Kelleher et al. |
| 8,343,046 B2 | 1/2013 | Miles et al. |
| 8,343,065 B2 | 1/2013 | Bartol et al. |
| 8,343,079 B2 | 1/2013 | Bartol et al. |
| 8,348,837 B2 | 1/2013 | Wenchell |
| 8,353,826 B2 | 1/2013 | Weiman |
| 8,355,780 B2 | 1/2013 | Miles et al. |
| 8,361,156 B2 | 1/2013 | Curran et al. |
| 8,376,937 B2 | 2/2013 | Xia et al. |
| 8,388,527 B2 | 3/2013 | Miles et al. |
| 8,403,841 B2 | 3/2013 | Miles et al. |
| 8,409,089 B2 | 4/2013 | Michaeli et al. |
| 8,430,813 B2 | 4/2013 | Selover et al. |
| 8,439,832 B2 | 5/2013 | Miles et al. |
| 8,449,463 B2 | 5/2013 | Nunley et al. |
| 8,454,504 B2 | 6/2013 | Michaeli et al. |
| 8,480,704 B2 | 7/2013 | Heiges et al. |
| 8,489,170 B2 | 7/2013 | Marino et al. |
| 8,491,471 B2 | 7/2013 | Deshmukh et al. |
| 8,500,634 B2 | 8/2013 | Miles et al. |
| 8,512,235 B2 | 8/2013 | Miles et al. |
| 8,517,954 B2 | 8/2013 | Bartol et al. |
| 8,523,767 B2 | 9/2013 | DeRidder et al. |
| 8,523,768 B2 | 9/2013 | Miles et al. |
| 8,545,531 B2 | 10/2013 | Geist et al. |

(56) References Cited

U.S. PATENT DOCUMENTS

| | | |
|---|---|---|
| 8,548,579 B2 | 10/2013 | Gharib et al. |
| 8,550,994 B2 | 10/2013 | Miles et al. |
| 8,556,808 B2 | 10/2013 | Miles et al. |
| 8,562,521 B2 | 10/2013 | Miles et al. |
| 8,562,539 B2 | 10/2013 | Marino |
| 8,568,317 B1 | 10/2013 | Gharib et al. |
| 8,571,628 B2 | 10/2013 | Kang et al. |
| 8,574,301 B2 | 11/2013 | Curran et al. |
| 8,585,762 B2 | 11/2013 | Hall |
| 8,591,432 B2 | 11/2013 | Pimenta et al. |
| 8,591,567 B2 | 11/2013 | Chau et al. |
| 8,602,982 B2 | 12/2013 | Miles et al. |
| 8,602,984 B2 | 12/2013 | Raymond et al. |
| 8,608,652 B2 | 12/2013 | Voegele et al. |
| 8,608,804 B2 | 12/2013 | Curran et al. |
| 8,622,897 B2 | 1/2014 | Raymond et al. |
| 8,628,469 B2 | 1/2014 | Miles et al. |
| 8,634,904 B2 | 1/2014 | Kaula et al. |
| 8,635,725 B2 | 1/2014 | Tannoury et al. |
| 8,636,656 B2 | 1/2014 | Nichter et al. |
| 8,636,657 B2 | 1/2014 | Hamada |
| 8,641,638 B2 | 2/2014 | Kelleher et al. |
| 8,663,100 B2 | 3/2014 | Miles et al. |
| 8,663,102 B2 | 3/2014 | Michaeli et al. |
| 8,672,840 B2 | 3/2014 | Miles et al. |
| 8,679,006 B2 | 3/2014 | Miles et al. |
| 8,685,105 B2 | 4/2014 | Curran et al. |
| 8,696,559 B2 | 4/2014 | Miles et al. |
| 8,702,600 B2 | 4/2014 | Perrow |
| 8,708,899 B2 | 4/2014 | Miles et al. |
| 8,738,123 B2 | 5/2014 | Gharib et al. |
| 8,747,307 B2 | 6/2014 | Miles et al. |
| 8,753,270 B2 | 6/2014 | Miles et al. |
| 8,753,271 B1 | 6/2014 | Miles et al. |
| 8,758,236 B2 | 6/2014 | Albrecht et al. |
| 8,764,649 B2 | 7/2014 | Miles et al. |
| 8,768,450 B2 | 7/2014 | Gharib et al. |
| 8,795,167 B2 | 8/2014 | Ainsworth et al. |
| 8,801,608 B2 | 8/2014 | Hardenbrook |
| 8,808,172 B2 | 8/2014 | Manzanares |
| 8,812,116 B2 | 8/2014 | Kaula et al. |
| 8,814,940 B2 | 8/2014 | Curran et al. |
| 8,821,394 B2 | 9/2014 | Hawkins et al. |
| 8,821,396 B1 | 9/2014 | Miles et al. |
| 8,852,089 B2 | 10/2014 | Blackwell et al. |
| 8,855,822 B2 | 10/2014 | Bartol et al. |
| 8,870,760 B2 | 10/2014 | Heiges et al. |
| 8,876,687 B2 | 11/2014 | Jones et al. |
| 8,882,661 B2 | 11/2014 | Hutton et al. |
| 8,882,679 B2 | 11/2014 | Bartol et al. |
| 8,892,259 B2 | 11/2014 | Bartol et al. |
| 8,894,574 B2 | 11/2014 | Ellman |
| 8,900,137 B1 | 12/2014 | Lovell et al. |
| 8,911,364 B2 | 12/2014 | Feigenwinter et al. |
| 8,915,846 B2 | 12/2014 | Miles et al. |
| 8,932,360 B2 | 1/2015 | Womble et al. |
| 8,942,797 B2 | 1/2015 | Bartol et al. |
| 8,942,801 B2 | 1/2015 | Miles et al. |
| 8,945,004 B2 | 2/2015 | Miles et al. |
| 8,956,283 B2 | 2/2015 | Miles et al. |
| 8,958,869 B2 | 2/2015 | Kelleher et al. |
| 8,968,363 B2 | 3/2015 | Weiman et al. |
| 8,977,352 B2 | 3/2015 | Gharib et al. |
| 8,979,767 B2 | 3/2015 | Bartol et al. |
| 8,983,593 B2 | 3/2015 | Bartol et al. |
| 8,986,344 B2 | 3/2015 | Sandhu |
| 8,992,425 B2 | 3/2015 | Karpowicz et al. |
| 8,992,558 B2 | 3/2015 | Stone et al. |
| 9,014,776 B2 | 4/2015 | Marino et al. |
| 9,037,250 B2 | 5/2015 | Kaula et al. |
| 9,039,630 B2 | 5/2015 | Bartol et al. |
| 9,044,280 B1 | 6/2015 | Arambula et al. |
| 9,050,146 B2 | 6/2015 | Woolley et al. |
| 9,060,757 B2 | 6/2015 | Lawson et al. |
| 9,066,701 B1 | 6/2015 | Finley et al. |
| 9,084,550 B1 | 7/2015 | Bartol et al. |
| 9,095,301 B2 | 8/2015 | Hamada |
| 9,113,854 B2 | 8/2015 | Ellman |
| 9,125,587 B2 | 9/2015 | Hawkins et al. |
| 9,138,137 B2 | 9/2015 | Deshmukh et al. |
| 9,138,217 B2 | 9/2015 | Smith et al. |
| 9,180,021 B2 | 11/2015 | Curran et al. |
| 9,204,871 B2 | 12/2015 | Miles et al. |
| 9,206,947 B2 | 12/2015 | Baumgartner et al. |
| 9,220,491 B2 | 12/2015 | Nunley et al. |
| 9,259,144 B2 | 2/2016 | Smith et al. |
| 9,265,493 B2 | 2/2016 | Miles et al. |
| 9,271,709 B2 | 3/2016 | Grey et al. |
| 9,271,711 B2 | 3/2016 | Hawkins et al. |
| 9,301,711 B2 | 4/2016 | Bartol et al. |
| 9,301,743 B2 | 4/2016 | Miles et al. |
| 9,314,152 B2 | 4/2016 | Pimenta et al. |
| 9,320,506 B2 | 4/2016 | Bertagnoli et al. |
| 9,339,263 B2 | 5/2016 | Fenn et al. |
| 9,351,718 B1 | 5/2016 | Arambula et al. |
| 9,380,932 B1 | 7/2016 | Lynn et al. |
| 9,386,916 B2 | 7/2016 | Predick et al. |
| 9,387,009 B2 | 7/2016 | Fatone et al. |
| 9,408,598 B1 | 8/2016 | Fantini et al. |
| 9,429,746 B2 | 8/2016 | Vayser et al. |
| 9,458,935 B2 | 10/2016 | Fricke et al. |
| 9,480,855 B2 | 11/2016 | DiMauro et al. |
| 9,486,133 B2 | 11/2016 | Lee et al. |
| 9,498,200 B2 | 11/2016 | Pfabe et al. |
| 9,554,789 B2 | 1/2017 | Overes et al. |
| 9,572,560 B2 | 2/2017 | Mast et al. |
| 9,610,130 B2 | 4/2017 | Vayser et al. |
| 9,615,818 B2 | 4/2017 | Baudouin et al. |
| 9,636,097 B2 | 5/2017 | Bass |
| 9,642,607 B2 | 5/2017 | Bootwala |
| 9,649,101 B2 | 5/2017 | Karpowicz et al. |
| 9,655,505 B1 | 5/2017 | Gharib et al. |
| 9,693,761 B2 | 7/2017 | Fedorov et al. |
| 9,782,158 B2 | 10/2017 | Nunley et al. |
| 9,795,370 B2 | 10/2017 | O'Connell et al. |
| 9,808,231 B2 | 11/2017 | Miraki et al. |
| 9,808,232 B2 | 11/2017 | Heiman et al. |
| 9,848,863 B2 | 12/2017 | Cryder et al. |
| 9,968,347 B2 | 5/2018 | Hutton et al. |
| 10,004,488 B2 | 6/2018 | Simonson |
| 10,046,149 B2 | 8/2018 | Bootwala |
| 10,172,515 B2 | 1/2019 | Lee et al. |
| 10,188,376 B2 | 1/2019 | Miraki et al. |
| 10,548,738 B2 | 2/2020 | Milz et al. |
| 2001/0039430 A1 | 11/2001 | Dubrul et al. |
| 2002/0193822 A1 | 12/2002 | Hung et al. |
| 2003/0018352 A1 | 1/2003 | Mollenauer et al. |
| 2003/0023259 A1 | 1/2003 | Dubrul et al. |
| 2003/0181939 A1 | 9/2003 | Bonutti |
| 2003/0191371 A1 | 10/2003 | Smith et al. |
| 2003/0195405 A1 | 10/2003 | Marino et al. |
| 2003/0225432 A1 | 12/2003 | Baptiste et al. |
| 2003/0225433 A1 | 12/2003 | Nakao |
| 2003/0229273 A1 | 12/2003 | Mulac et al. |
| 2003/0233115 A1 | 12/2003 | Eversull et al. |
| 2004/0087833 A1 | 5/2004 | Bauer et al. |
| 2004/0236186 A1 | 11/2004 | Chu |
| 2004/0243158 A1 | 12/2004 | Konstantino et al. |
| 2004/0243167 A1 | 12/2004 | Tanaka et al. |
| 2005/0119531 A1 | 6/2005 | Sharratt |
| 2005/0124937 A1 | 6/2005 | Kick et al. |
| 2005/0182436 A1 | 8/2005 | Chopra |
| 2005/0234304 A1 | 10/2005 | Dewey et al. |
| 2005/0234493 A1 | 10/2005 | Carr et al. |
| 2006/0004398 A1 | 1/2006 | Binder et al. |
| 2006/0052750 A1 | 3/2006 | Lenker et al. |
| 2006/0135852 A1 | 6/2006 | Koros et al. |
| 2006/0135981 A1 | 6/2006 | Lenker et al. |
| 2006/0135987 A1 | 6/2006 | Jones et al. |
| 2006/0206008 A1 | 9/2006 | Dalton |
| 2006/0206009 A1 | 9/2006 | Von Wald et al. |
| 2006/0224044 A1 | 10/2006 | Marchek et al. |
| 2006/0224045 A1 | 10/2006 | Whipple et al. |
| 2006/0224078 A1 | 10/2006 | Hoey et al. |

(56) References Cited

U.S. PATENT DOCUMENTS

| | | |
|---|---|---|
| 2006/0258951 A1 | 11/2006 | Bleich et al. |
| 2006/0287574 A1 | 12/2006 | Chin |
| 2007/0010716 A1* | 1/2007 | Malandain ......... A61B 17/3403 600/224 |
| 2007/0032703 A1 | 2/2007 | Sankaran et al. |
| 2007/0049962 A1 | 3/2007 | Marino et al. |
| 2007/0060939 A1 | 3/2007 | Lancial et al. |
| 2007/0168043 A1 | 7/2007 | Ferree |
| 2007/0208366 A1 | 9/2007 | Pellegrino et al. |
| 2007/0213591 A1 | 9/2007 | Aizenfeld et al. |
| 2007/0219416 A1 | 9/2007 | Perez-Cruet et al. |
| 2007/0239159 A1 | 10/2007 | Altarac et al. |
| 2007/0270623 A1 | 11/2007 | Merrill |
| 2007/0270653 A1 | 11/2007 | Vayser et al. |
| 2008/0058606 A1 | 3/2008 | Miles et al. |
| 2008/0064945 A1 | 3/2008 | Marino et al. |
| 2008/0065135 A1 | 3/2008 | Marino et al. |
| 2008/0065140 A1 | 3/2008 | Bonutti |
| 2008/0065144 A1 | 3/2008 | Marino et al. |
| 2008/0065178 A1 | 3/2008 | Kelleher et al. |
| 2008/0071191 A1 | 3/2008 | Kelleher et al. |
| 2008/0103519 A1 | 5/2008 | Bonutti |
| 2008/0109026 A1 | 5/2008 | Kassam |
| 2008/0132764 A1 | 6/2008 | Hamada |
| 2008/0147109 A1 | 6/2008 | Kambin et al. |
| 2008/0183204 A1 | 7/2008 | Greenhalgh et al. |
| 2008/0215081 A1 | 9/2008 | Hsueh et al. |
| 2008/0221586 A1 | 9/2008 | Garcia-Bengochea et al. |
| 2008/0255563 A1 | 10/2008 | Farr et al. |
| 2008/0319268 A1 | 12/2008 | Michaeli et al. |
| 2008/0319432 A1 | 12/2008 | Ely et al. |
| 2009/0024158 A1 | 1/2009 | Viker |
| 2009/0036744 A1 | 2/2009 | Vayser |
| 2009/0036746 A1 | 2/2009 | Blackwell et al. |
| 2009/0062871 A1 | 3/2009 | Chin et al. |
| 2009/0149716 A1 | 6/2009 | Diao et al. |
| 2009/0171284 A1 | 7/2009 | Burke et al. |
| 2010/0041955 A1 | 2/2010 | Grey et al. |
| 2010/0160947 A1 | 6/2010 | Akyuz et al. |
| 2010/0178100 A1 | 7/2010 | Fricke et al. |
| 2010/0180906 A1 | 7/2010 | Marozsan et al. |
| 2010/0241129 A1 | 9/2010 | Markey et al. |
| 2011/0208005 A1* | 8/2011 | Michaeli ................ A61B 90/35 600/215 |
| 2011/0237898 A1 | 9/2011 | Stone et al. |
| 2011/0313312 A1 | 12/2011 | Hoey et al. |
| 2012/0010472 A1 | 1/2012 | Spann |
| 2012/0022575 A1 | 1/2012 | Mire et al. |
| 2012/0029382 A1 | 2/2012 | Kelleher et al. |
| 2012/0035730 A1 | 2/2012 | Spann |
| 2012/0041272 A1 | 2/2012 | Dietze, Jr. et al. |
| 2012/0046526 A1 | 2/2012 | Boettner et al. |
| 2012/0101341 A1 | 4/2012 | Malandain et al. |
| 2012/0232349 A1 | 9/2012 | Perrow |
| 2013/0090680 A1 | 4/2013 | Akyuz et al. |
| 2013/0103103 A1 | 4/2013 | Mire et al. |
| 2013/0123582 A1 | 5/2013 | Xia et al. |
| 2013/0190575 A1 | 7/2013 | Mast et al. |
| 2013/0211202 A1 | 8/2013 | Perez-Cruet et al. |
| 2013/0317303 A1 | 11/2013 | Deshmukh et al. |
| 2014/0039264 A1 | 2/2014 | Heiman |
| 2014/0114135 A1 | 4/2014 | Ellman |
| 2014/0114138 A1 | 4/2014 | Fedorov et al. |
| 2014/0114139 A1 | 4/2014 | Ziolo et al. |
| 2014/0128979 A1 | 5/2014 | Womble et al. |
| 2014/0142420 A1 | 5/2014 | Jackson, III |
| 2014/0148650 A1 | 5/2014 | Miles et al. |
| 2014/0172002 A1 | 6/2014 | Predick |
| 2014/0235950 A1 | 8/2014 | Miles et al. |
| 2014/0257035 A1 | 9/2014 | Blain |
| 2014/0257044 A1 | 9/2014 | Blain et al. |
| 2014/0275801 A1 | 9/2014 | Menchaca et al. |
| 2014/0276869 A1 | 9/2014 | Tatsumi |
| 2014/0288374 A1 | 9/2014 | Miles et al. |
| 2014/0288375 A1 | 9/2014 | Miles et al. |
| 2014/0316212 A1 | 10/2014 | Reimels |
| 2014/0357946 A1 | 12/2014 | Golden et al. |
| 2015/0018623 A1 | 1/2015 | Friedrich et al. |
| 2015/0018625 A1 | 1/2015 | Miraki et al. |
| 2015/0045626 A1 | 2/2015 | Reimels |
| 2015/0051448 A1 | 2/2015 | Hunt et al. |
| 2015/0051506 A1 | 2/2015 | Wybo et al. |
| 2015/0051507 A1 | 2/2015 | Wybo et al. |
| 2015/0080717 A1 | 3/2015 | Ferko |
| 2015/0088029 A1 | 3/2015 | Wybo |
| 2015/0088030 A1 | 3/2015 | Taylor |
| 2015/0105624 A1 | 4/2015 | Martinelli et al. |
| 2015/0112148 A1 | 4/2015 | Bouquet |
| 2015/0119987 A1 | 4/2015 | Davignon et al. |
| 2015/0133734 A1 | 5/2015 | Miles et al. |
| 2015/0150693 A1 | 6/2015 | Gharib et al. |
| 2015/0157227 A1 | 6/2015 | Kelleher et al. |
| 2015/0157228 A1 | 6/2015 | Marino et al. |
| 2015/0164496 A1 | 6/2015 | Karpowicz et al. |
| 2015/0164569 A1 | 6/2015 | Reitblat et al. |
| 2015/0216478 A1 | 8/2015 | Kaula et al. |
| 2015/0230749 A1 | 8/2015 | Gharib et al. |
| 2015/0230787 A1 | 8/2015 | Friedrich et al. |
| 2015/0257784 A1 | 9/2015 | Corbin et al. |
| 2015/0327948 A1 | 11/2015 | Schoepp et al. |
| 2015/0342589 A1 | 12/2015 | Bootwala |
| 2015/0366548 A1 | 12/2015 | Lauchner |
| 2016/0038302 A1 | 2/2016 | Curran et al. |
| 2016/0051242 A1 | 2/2016 | Predick et al. |
| 2016/0081681 A1 | 3/2016 | Waugh et al. |
| 2016/0081682 A1 | 3/2016 | Miles et al. |
| 2016/0120530 A1 | 5/2016 | Miles et al. |
| 2016/0120532 A1 | 5/2016 | Donald |
| 2016/0174958 A1 | 6/2016 | Miles et al. |
| 2016/0174959 A1 | 6/2016 | Miles et al. |
| 2016/0183913 A1 | 6/2016 | Singh et al. |
| 2016/0192921 A1 | 7/2016 | Pimenta et al. |
| 2016/0192922 A1 | 7/2016 | Friedrich et al. |
| 2016/0199193 A1 | 7/2016 | Willis et al. |
| 2016/0242736 A1 | 8/2016 | Freiburg et al. |
| 2016/0278755 A1 | 9/2016 | Stone et al. |
| 2016/0338795 A1 | 11/2016 | Vayser et al. |
| 2016/0345949 A1 | 12/2016 | Harvey et al. |
| 2016/0361052 A1 | 12/2016 | Reimels |
| 2017/0000562 A1 | 1/2017 | Frank et al. |
| 2017/0007228 A1 | 1/2017 | Costabile |
| 2017/0014118 A1 | 1/2017 | Capote |
| 2017/0014119 A1 | 1/2017 | Capote et al. |
| 2017/0027555 A1 | 2/2017 | Paumier et al. |
| 2017/0065268 A1 | 3/2017 | Sindram |
| 2017/0071589 A1 | 3/2017 | Simonson |
| 2017/0150956 A1 | 6/2017 | Baudouin et al. |
| 2017/0215856 A1 | 8/2017 | Martinelli et al. |
| 2017/0231614 A1 | 8/2017 | Vogel et al. |
| 2017/0340317 A1 | 11/2017 | Fatone et al. |
| 2018/0064450 A1 | 3/2018 | Jackson, III |
| 2018/0333152 A1 | 11/2018 | Heiman |

FOREIGN PATENT DOCUMENTS

| | | |
|---|---|---|
| WO | 9916499 A1 | 4/1999 |
| WO | 2006102085 A2 | 9/2006 |
| WO | 2008039427 A2 | 4/2008 |
| WO | 2009137700 A1 | 11/2009 |
| WO | 2018039228 A1 | 3/2018 |

OTHER PUBLICATIONS

Bush et al., U.S. Appl. No. 62/546,841, filed Aug. 17, 2017, titled "Independent Rod Suspension".

Popejoy et al., U.S. Appl. No. 62/546,796, filed Aug. 17, 2017, titled "Bridges and Lighting for Lateral Access".

Milz et al., U.S. Appl. No. 62/319,513, filed Apr. 7, 2016, titled "Expandable Interbody Implant."

Extended European Search Report including Written Opinion for Application No. EP19166059.6, dated Nov. 29, 2019, pp. 1-11.

Aesculap Spine; Caspar Cervical Retractor System, Product Brochure Apr. 2009 Doc# 510, 16 pages.

(56) References Cited

OTHER PUBLICATIONS

Biomet Spine, "Timberline Lateral Fusion System, Surgical Technique Guide", Copyright 2014, 52 pages.
Biomet Spine; AccuVision Minimally Invasive Spinal Exposure System, Surgical Technique Dec. 2009, 28 pages.
Biomet Spine; VuePASS, Surgical Technique Jun. 2007 P/N 216001L. 36 pages.
Depuy; Pipeline Concorde, Surgical Technique Jul. 2007 M102-20-001, 24 pages.
Extended European Search Report for Application No. 09837915.9 dated Mar. 28, 2014.
International Search Report for Application No. PCT/US2009/068474 dated Aug. 9, 2010.
International Search Report for Application No. PCT/US2011/032525 dated Dec. 15, 2011.
K2M; Tera Nova, Product Brochure 2012 K2-15/7002-01 Rev.3, 2 pages.
Krause et al., U.S. Appl. No. 62/546,780, filed Aug. 17, 2017, titled "Lateral Access Alignment Guide and Rigid Arm".
Medtronic; Mast Quadrant, Product Brochure 2005 MLITQUDST5, 40 pages.
Milz et al., U.S. Appl. No. 62/560,910, filed Sep. 20, 2017, titled "Spinal Implants".
NuVasive; Maxcess-XLIF, Surgical Technique 2007 9500138 A.0, 32 pages.
Synthes; Oracle Spacer, Technique Guide Dec. 2010 J8158-C, 40 pages.
Wills et al., U.S. Appl. No. 62/103,276, filed Jan. 14, 2015, titled "Spinal Implant With Porous and Solid Surfaces".
Zimmer Spine; Harmony Retractor System, Surgical Technique L1477 Rev. A Aug. 2009, 20 pages.
Zimmer; ARAS Retractor, Surgical Technique L1377 Rev. A 2007, 20 pages.
Partial European Search Report including Provisional Opinion for EP19166059.6 dated Aug. 26, 2019.
Lanx; Timberline Lateral Fusion System, Surgical Technique LIT8710-0111.03, copyright 2012, Lanx Inc., Broomfield, CO. 42 pages.

* cited by examiner

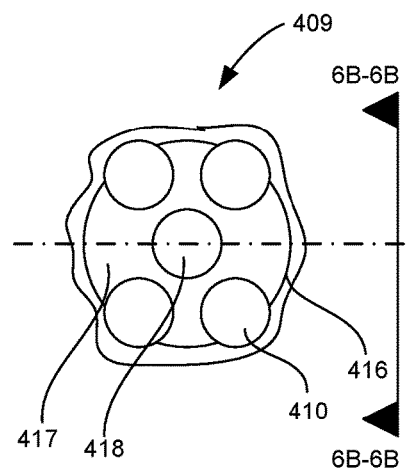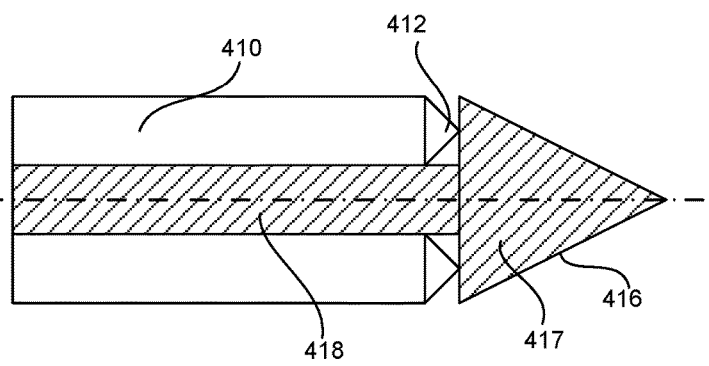
FIG. 6A  FIG. 6B
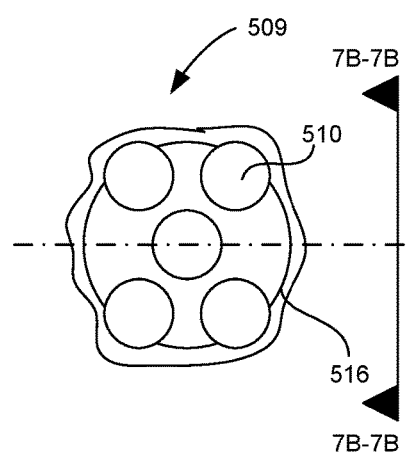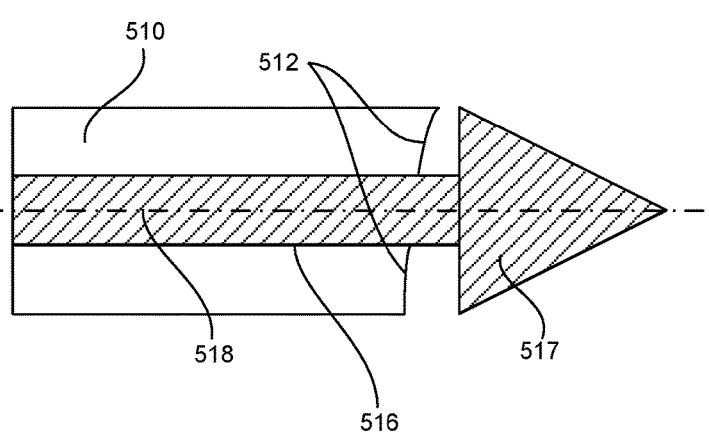
FIG. 7A  FIG. 7B

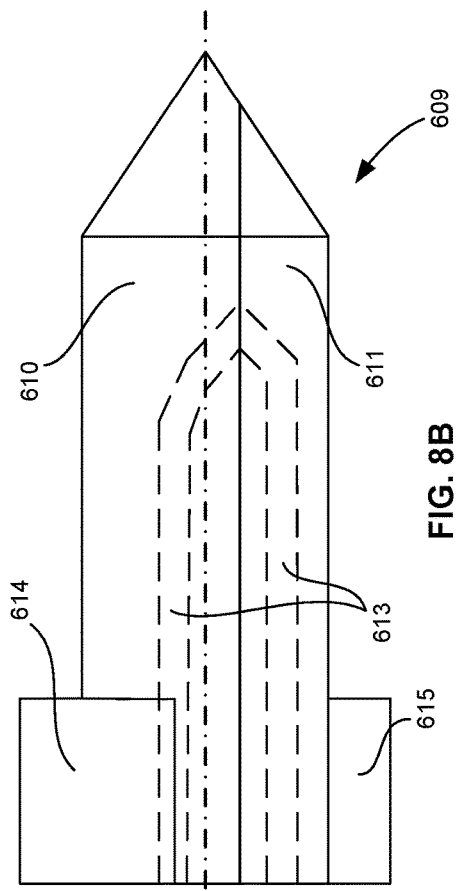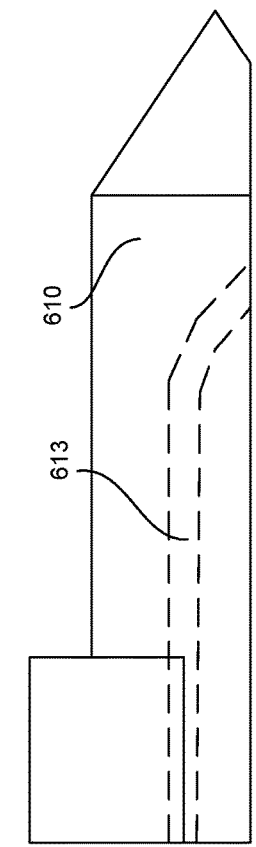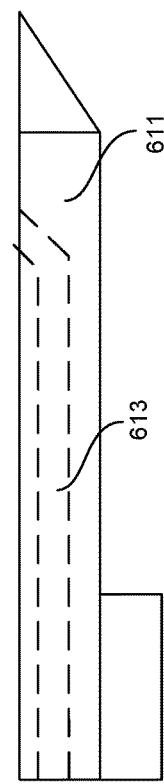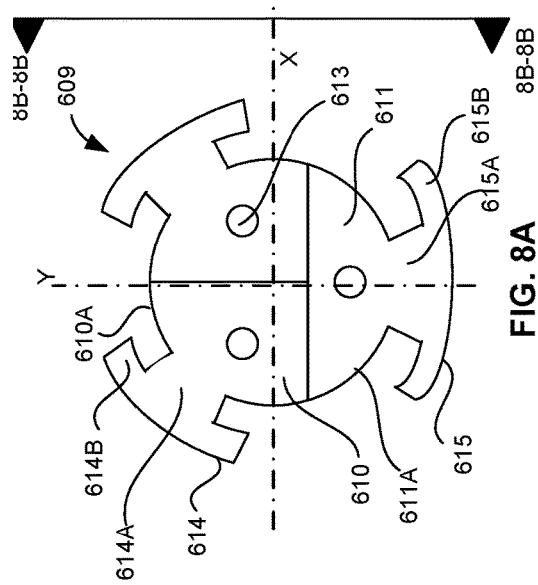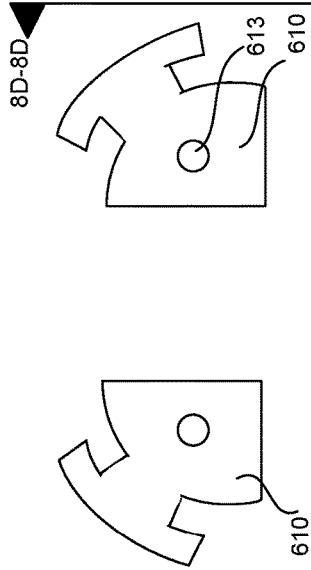
FIG. 8A  FIG. 8B  FIG. 8C  FIG. 8D

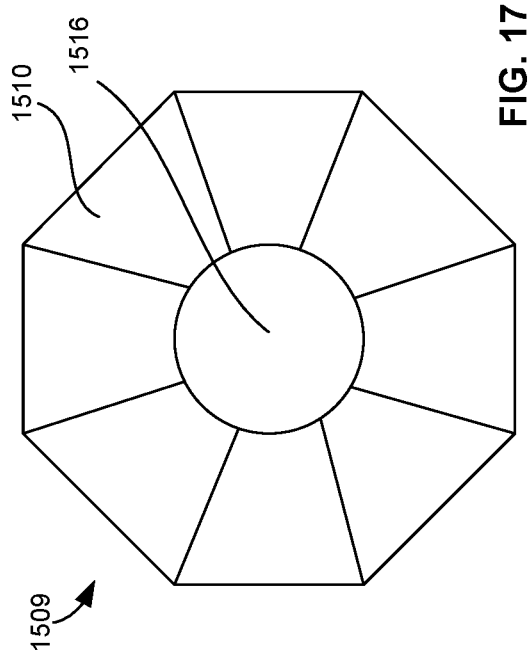
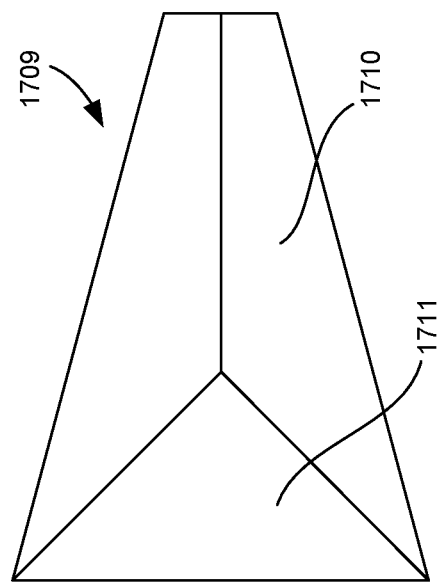
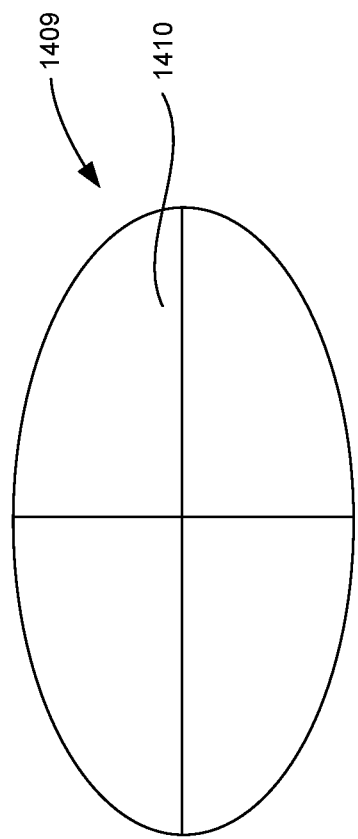
FIG. 16
FIG. 17
FIG. 18
FIG. 19

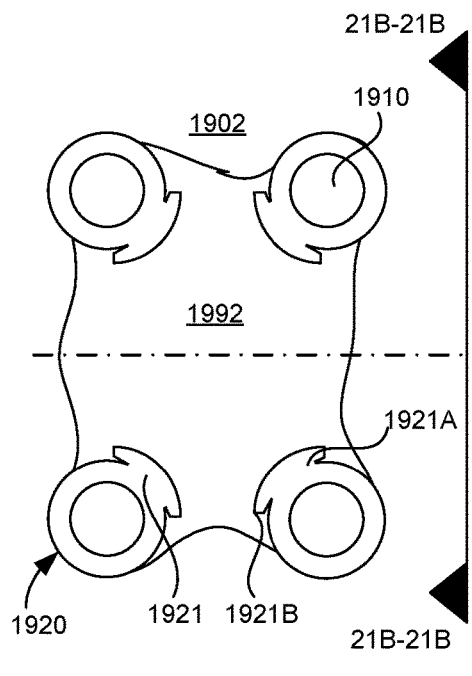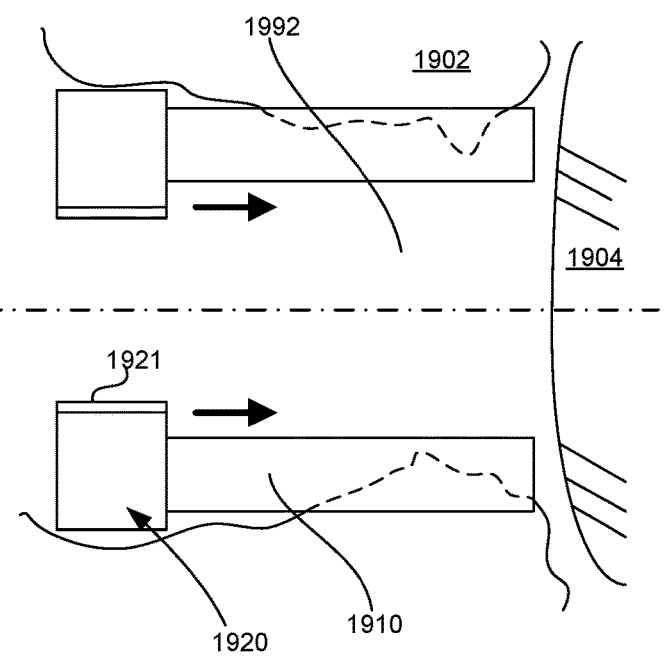
FIG. 21A            FIG. 21B
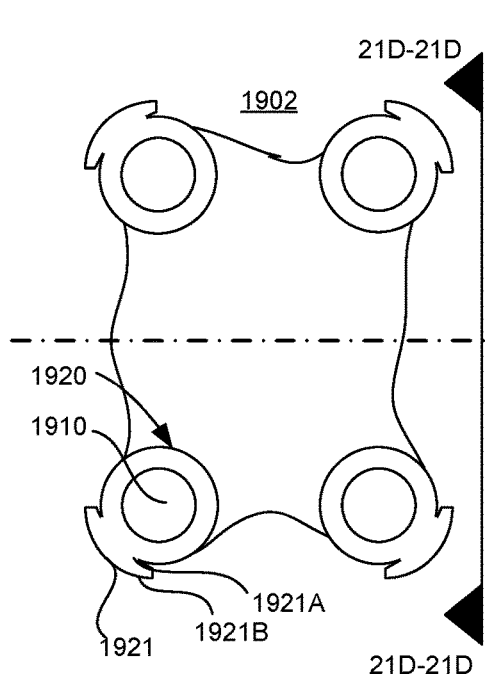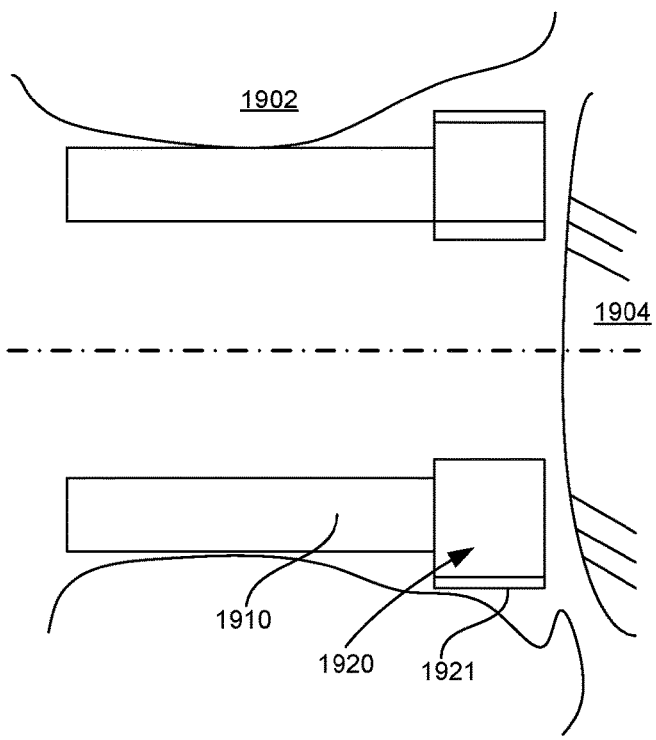
FIG. 21C            FIG. 21D

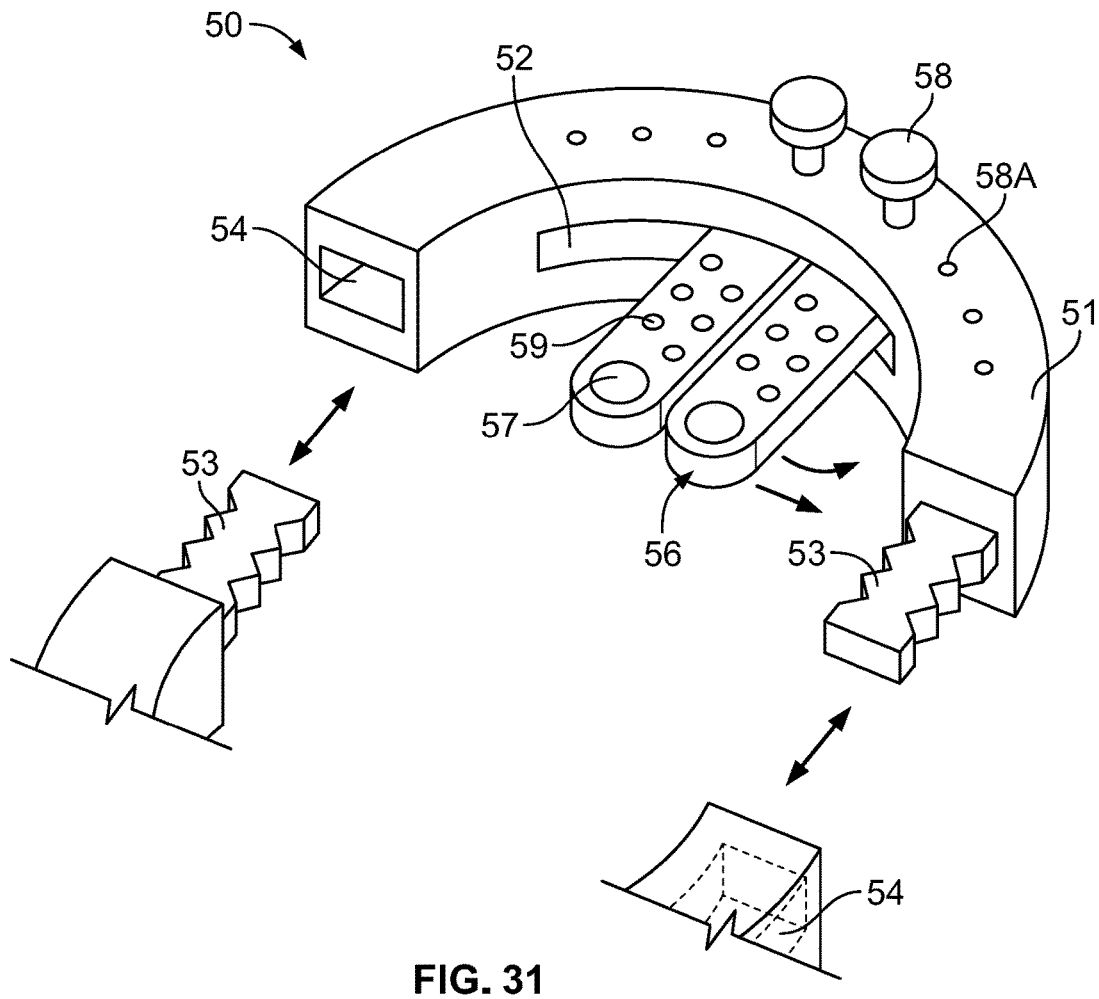
FIG. 31
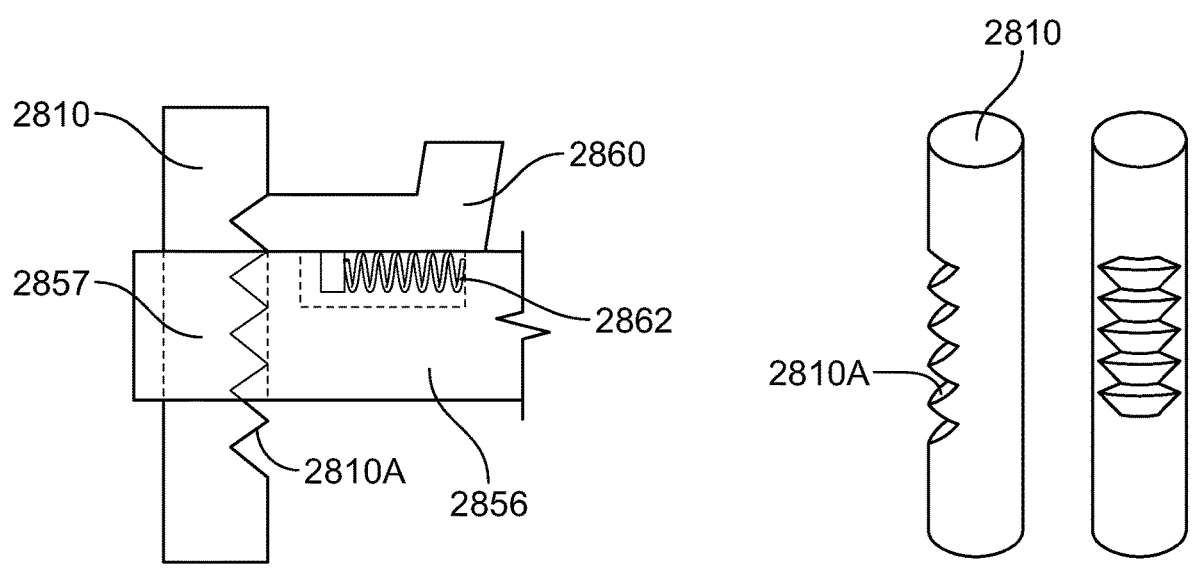
FIG. 32A  FIG. 32B

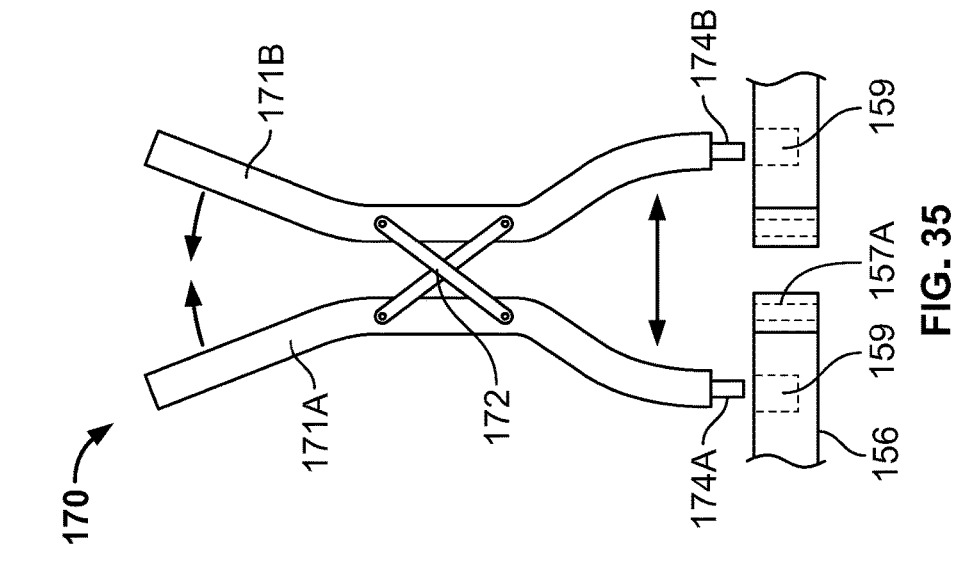
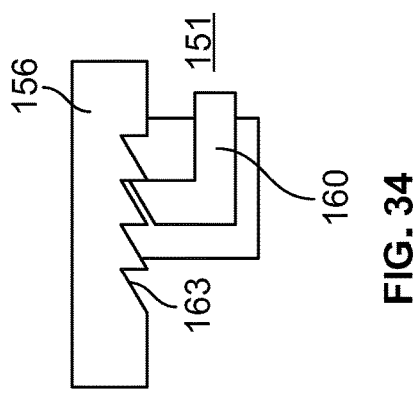
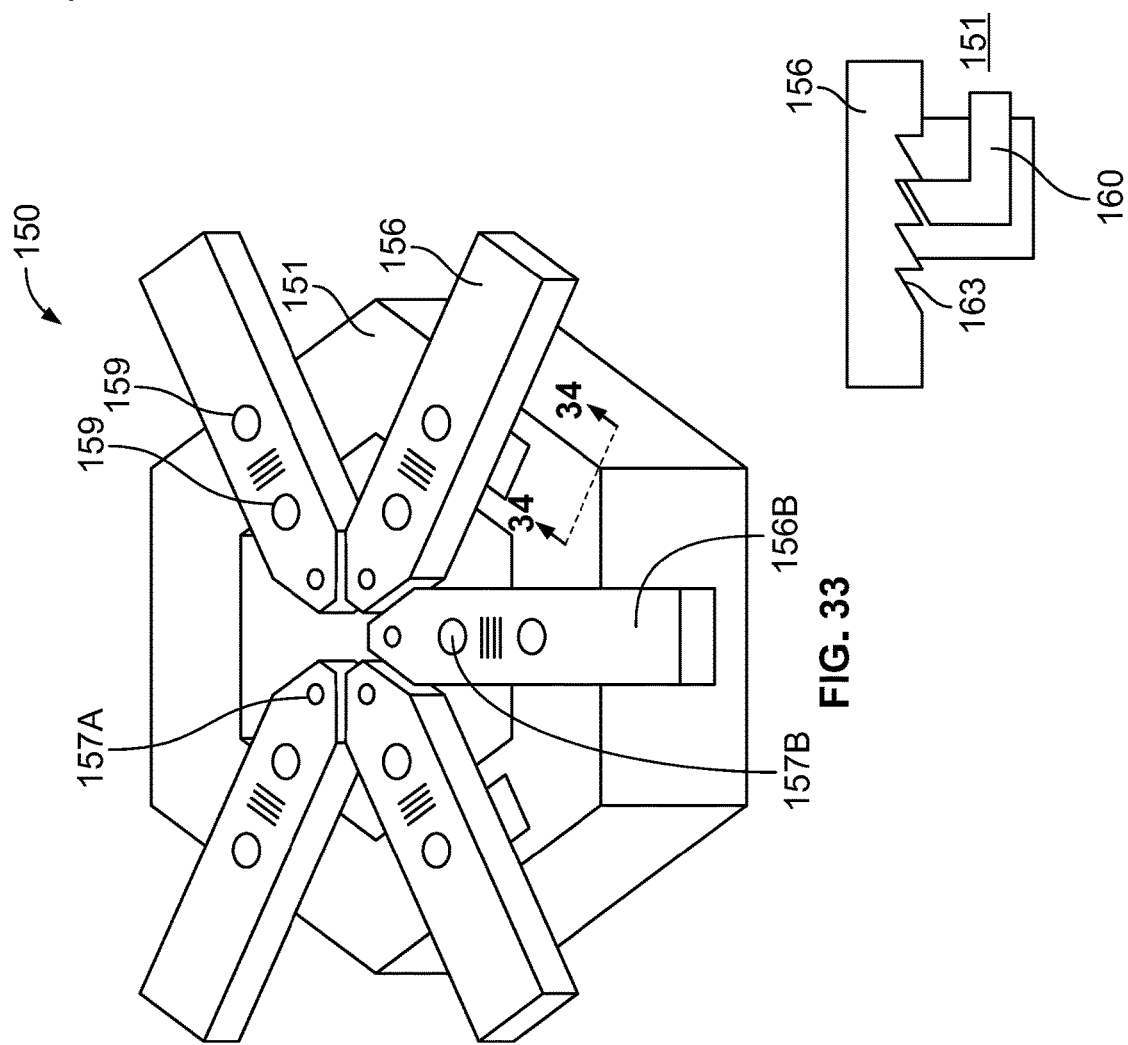

INSTRUMENTATION AND METHODS FOR THE IMPLANTATION OF SPINAL IMPLANTS

The present application is a national phase entry under 35 U.S.C. § 371 of International Application No. PCT/US2017/048009 filed Aug. 22, 2017, which claims priority from U.S. Provisional Patent Application Nos. 62/378,485 and 62/470,534, filed Aug. 23, 2016 and Mar. 13, 2017, respectively, the disclosures of which are hereby incorporated by reference herein in their entirety.

BACKGROUND OF THE INVENTION

Spinal implants are widely utilized in spinal procedures. In particular, spinal fusion implants are often employed to immobilize and fuse adjacent vertebral bodies. These implants may be packed with materials that promote bone growth between the vertebral bodies, and may be utilized in conjunction with other fixation devices, such as pedicle screws. In any event, spinal implants are among the most important devices for curing spinal maladies, such as disc disease and scoliosis.

There are many different types of spinal implants, as well as methods for implanting them. For instance, implants that are inserted along a posterior approach include posterior lumbar interbody fusion (PLIF) and transforaminal lumbar interbody fusion (TLIF) implants. Likewise, implants that are inserted along an anterior approach include anterior lumbar interbody fusion (ALIF) implants. One type of implant that has garnered more acceptance in recent years are lateral implants. These implants are inserted laterally, which allows them to be larger than typical PLIF, TLIF and ALIF implants. This in turn provides for a more stable construct between the vertebral bodies, as well as more fusion to occur through the implant.

One method for implanting lateral implants is via a lateral trans-psoas approach. This typically involves the creation of an incision on the lateral side of the patient. Thereafter, a path to the vertebral bodies is systematically created by dilating the skin and muscle tissue through the use of sequential dilators. This allows for the path to be created in a step-wise fashion without tearing or otherwise significantly traumatizing the surrounding tissue. Ultimately, a retractor is placed over the last placed sequential dilator, which can even further retract the surrounding tissue and provides for a suitable passage in which the surgery can be conducted.

Among the most important anatomical structures that needs to be passed through during a lateral approach is the psoas muscle. This is a muscle that abuts up against spine in various places and includes many nerves. The aforementioned sequential dilation is often coupled with neuro-monitoring techniques to ensure even the slow dilation procedure does not result in unwanted nerve impingement. Thus, even the step-wise enlargement of the path to the spinal in this procedure can, without significant aid from nerve monitoring equipment, result in irreparable harm to the patient. Moreover, this deliberate sequential enlargement adds time to an already time consuming procedure.

Thus, there is a need for improved apparatuses and systems for implanting spinal implants, including without limitation, those implanted via a lateral approach.

BRIEF SUMMARY OF THE INVENTION

The present invention may generally, in a first aspect, relate to a minimally invasive system for accessing the spine. Such access may be for the purpose of removing spinal material and/or for the placement of implants, for example. In another aspect, the system is applied in a method. The system and method are particularly advantageous when access to the spine requires traversing the psoas muscle, as the system is configured to be minimally invasive during insertion and advancement into a body of a patient, thus minimizing the risk of making contact with any nerves during the advancement of the adjustable rod structure. Moreover, the system allows for the controlled expansion of a pathway to a surgical site.

In one embodiment, the system includes three or more rods, a combined profile of the rods forming a taper at a distal end. The system also includes at least one ring adapted to hold, separate and/or engage with the rods when the rods are retracted from one another. To facilitate retraction of the rods, a retractor configured to engage and secure the rods is also included as part of the system.

In another embodiment, the present invention relates to a system for implantation of spinal implants. The system includes three or more rods moveable from a first position to a second position, a retractor configured to move the rods between the first and second positions; and at least one ring configured to hold the rods in the second position.

In other embodiments, the system also includes four rods and a probe, the probe being removable when the rods are in the second position. In a variant, the probe is cannulated. In another embodiment, the system also includes a plurality of rings. In yet another embodiment, the ring is slidable over at least one rod. In a variant, the placement of ring moves the rods to a third position. In one embodiment, the rods form a tapered end in the first position. In another embodiment, the probe forms a tapered end.

In another embodiment, the present invention is a method that involves initially identifying an approach to the spine, such as a lateral approach. The method includes the following steps: inserting an adjustable rod structure including three or more rods adjacent to one another into a patient through a percutaneous incision; advancing the adjustable rod structure until a distal end of the adjustable rod structure is proximal to a target site internal to the patient; retracting the three or more rods of the adjustable rod structure creating a portal extending from a location external to the patient to the target site; and advancing a ring into the portal, the ring maintaining a separation between the rods. To the extent the rods pass through the psoas muscle, the tapered end, or tip, of the combined rods splits and/or separates the muscle tissue as it advances. In other embodiments, the method further includes removing a probe included with the adjustable rod structure after retracting the three or more rods. Other embodiments, may include the use of more than one ring to create a rigid pathway to the surgical site.

In yet another embodiment, the present invention is a method of creating access to the spine. The method includes steps as follows: inserting an adjustable rod structure including three or more rods adjacent to one another into a patient through an incision; advancing the adjustable rod structure until a distal end of the adjustable rod structure is proximal to a target site internal to the patient; retracting the three or more rods of the adjustable rod structure creating a portal extending from a location external to the patient to the target site; and advancing a ring into the portal, the ring maintaining a separation between the rods.

In another embodiment, the method also includes a step of removing a probe of the adjustable rod structure after retracting the three or more rods. In another embodiment, the method includes an additional step of engaging a retractor with the adjustable rod structure. In a variant of this embodiment, a probe is removed from the adjustable rod structure. In a further variant, the inserting step includes placing the probe over a K-wire. In yet another embodiment, the inserting step includes monitoring the presence of nerves proximate the adjustable rod structure.

In any of the above embodiments and in additional embodiments, the systems and methods can also include neuromonitoring, endoscopic devices and techniques, robotic devices, and navigation technology.

BRIEF DESCRIPTION OF THE DRAWINGS

A more complete appreciation of the subject matter of the present invention and of the various advantages thereof can be realized by reference to the following detailed description in which reference is made to the accompanying drawings in which:

FIGS. 6A and 6B are rear facing and side views of an adjustable rod structure according to another embodiment of the present invention.

FIGS. 7A and 7B are rear facing and side views of an adjustable rod structure according to another embodiment of the present invention.

FIGS. 8A and 8B are rear facing and side views of an adjustable rod structure according to another embodiment of the present invention in a closed position.

FIGS. 8C and 8D are rear facing and side views of the adjustable rod structure shown in FIG. 8A in a retracted position.

FIG. 16 is a rear facing view of an adjustable rod structure according to another embodiment of the present invention.

FIG. 17 is a rear facing view of an adjustable rod structure according to another embodiment of the present invention.

FIG. 18 is a rear facing view of an adjustable rod structure according to another embodiment of the present invention.

FIG. 19 is a rear facing view of an adjustable rod structure according to another embodiment of the present invention.

FIGS. 21A and 21B are rear facing and side views of rings disposed on rods for use with an adjustable rod structure according to one embodiment of the present invention, the rings being in a first position on the rods.

FIGS. 21C and 21D are rear facing and side views of the rings and rods of FIGS. 21A and 21B, the rings being in a second position on the rods.

FIG. 31 is a perspective view of a retractor according to another embodiment of the present invention.

FIG. 32A is a partial side view of a retractor according to another embodiment of the present invention.

FIG. 32B is a perspective view of a rod for use with the retractor of FIG. 32A.

FIG. 33 is a perspective view of a retractor according to another embodiment of the present invention.

FIG. 34 is a partial side view of the retractor shown in FIG. 33.

FIG. 35 is a side view of a distracter engaging the retractor of FIG. 33.

DETAILED DESCRIPTION

Figure 1:
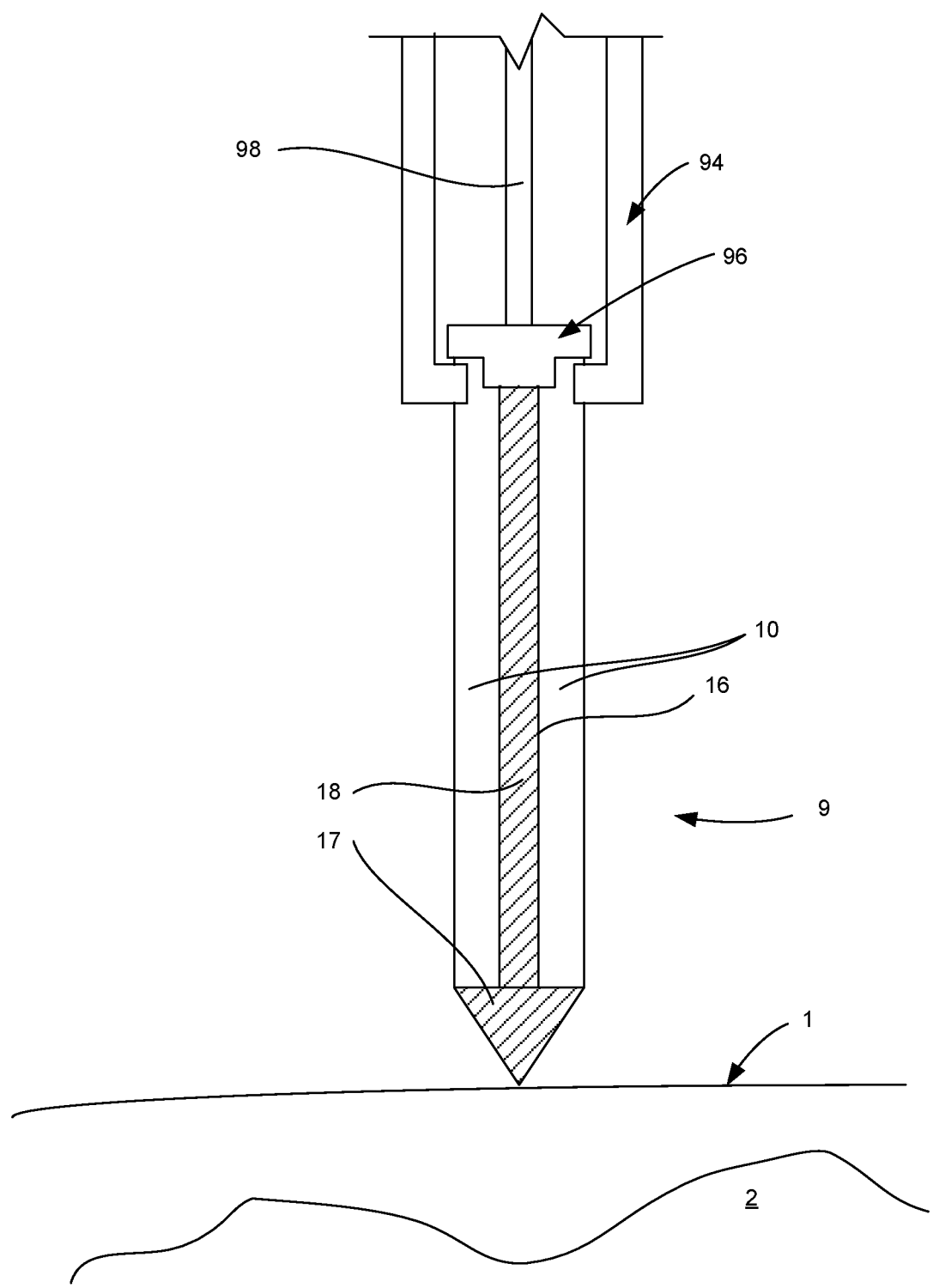
FIG. 1 is a side view of several components of instrumentation for implantation of a spinal implant according to one embodiment of the present invention.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

The various apparatuses, systems, kits and methods of the present invention are intended to improve and streamline access to anatomical structures within the body, in particular, structures of and relating to the vertebrae. However, the present invention is not limited to accessing the spine via specific approaches. In fact, the present invention has applicability to many spinal implantation approaches, and for use in other areas of the body. Through the embodiments described herein, access is achieved under a wide variety of surgical conditions efficiently, safely and with fewer tools than with techniques known in the art.

As used herein, when referring to the system employed in the methods of accessing an intended anatomical location, the term "proximal" means closer to the surgeon operating and/or holding a retractor and adjustable rod structure and the term "distal" means closer to the intended anatomical location, such as an intervertebral disc space. The term "target anatomical location" as used herein is intended to refer to a location in the body that is the subject of the surgery and for which a portal must be created to achieve access. Examples of a target anatomical location include an intervertebral disc between vertebral bodies in the spine. Other terms that are used interchangeably with target anatomical location herein include intended anatomical location, anatomical location, surgical target site, target site and target anatomical site.

Figure 2A:
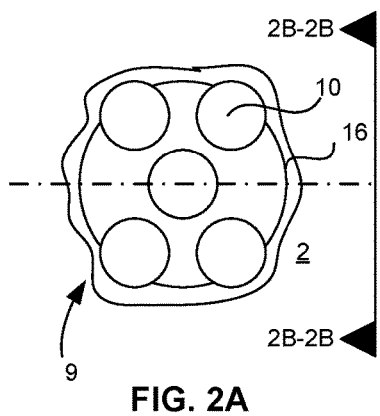
FIGS. 2A and 2B are rear facing and side views of the adjustable rod structure shown in FIG. 1 in the closed position.
Figure 2B:
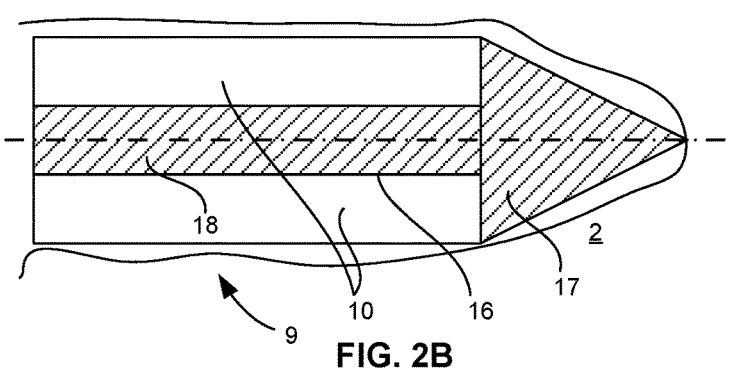

The present invention provides instruments and methodology for providing access to different areas of the body. Although discussed below largely in relation to instruments and methods for providing access to the spine during a spinal fusion procedure, it is to be understood that the present invention may have applicability to other areas of the body, as well as surgery in general. In one embodiment, as is shown in FIGS. 2A-2F, the present invention includes an adjustable rod structure 9 that is actuated by a retractor. Adjustable rod structure 9, as shown, includes a central rod, or probe 16, that is located at a center surrounded by other, shorter rods 10. FIGS. 2A and 2B depict adjustable rod structure 9 in a closed position, while FIGS. 2C-2F depict such structure in different open positions. Adjustable rod structure 9 is designed such that it is easily inserted through an incision and moved towards a surgical target site, such as the lumbar spine. Thereafter, adjustable rod structure 9 can be opened/closed by the retractor, which in one example shown in FIG. 39 (a retractor 50), is supported by a stabilizing element 90, such as a table. However, it is contemplated that the retractors as described herein can be supported by hand, by static structures (e.g., table) or by other means (e.g., robotic systems, as described below) that provide stability for the rods and do not impede access to the anatomical location sought to be accessed for performance of surgery. The various components of the present invention will now be discussed in more detail.

Probe

Figure 2C:
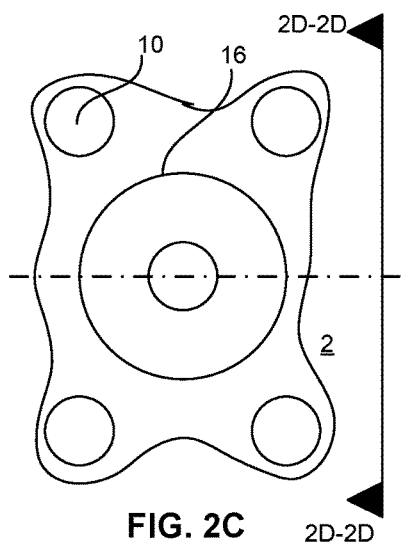
FIGS. 2C and 2D are rear facing and side views of the adjustable rod structure shown in FIG. 1 in a retracted position.
Figure 2D:
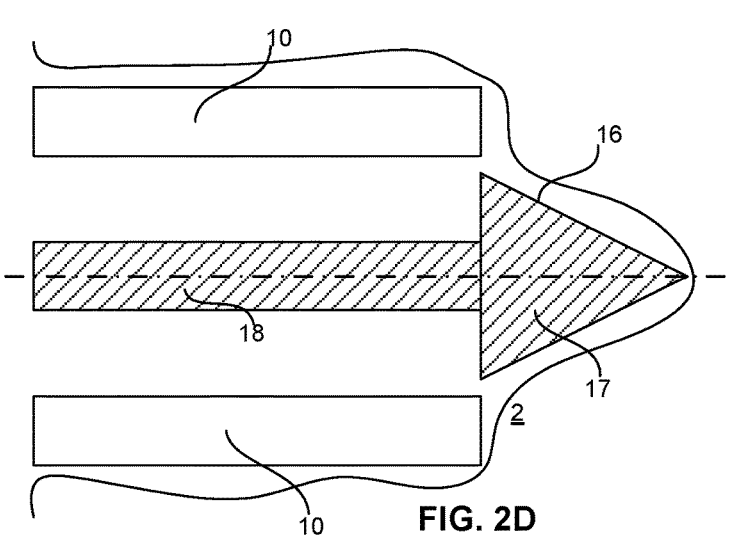
Figure 2E:
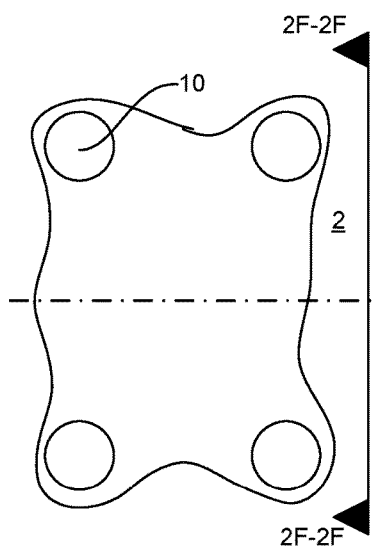
FIGS. 2E and 2F are rear facing and side views of the adjustable rod structure shown in FIG. 1 in a retracted position with a probe removed.

As described herein, probe 16 includes an insertion portion 17 and an extension portion 18. In the embodiment shown in FIGS. 2A-2F, extension portion 18 of probe 16 has the same or similar cross section as each individual rod 10 through a portion of its length, but is connected with the larger, conical shaped insertion portion 17 at its distal end. Insertion portion 17 can also be described as a tapered end. Of course, and as described in greater detail below, it is contemplated that a diameter of extension portion 18 can vary in dimension with respect to a diameter of one or more rods 10. At its largest cross-section (see FIG. 2B, for example), insertion portion 17 of probe 16 has a profile matching the combined cross section of rods 10 and extension portion 18, and tapers to a point remote from rods 10. The tip of insertion portion 17 can be sharp, rounded or blunt. In addition, as shown in FIGS. 2B, and 2D, insertion portion 17 has an outer surface at a small angle relative to a longitudinal axis of probe 16 so that the outer surface is at an angle less than 45 degrees relative to the longitudinal axis. Such a tip structure is advantageous in that muscle tearing is minimized compared with shallower tip surfaces. The steep angle makes it easier for muscle fibers to separate as the probe is advanced. Nonetheless, in some variants, the aforementioned angle can be greater than 45 degrees. The shape of insertion portion 17 of probe 16 is conical, but can exhibit other shapes, such as an overall bullet-shape, arrow-shape, or any other shape so that it tapers from a proximal to a distal end, the distal end corresponding to the tip. In one exemplary construction, the largest outer cross-sectional dimension of probe 16 at a base of insertion portion 17 is between approximately 7 and 10 mm in diameter. Again, this is approximately the same as the cross section for all rods 10 and extension portion 18 combined (i.e., profile of adjustable rod structure 9) so that it forms a cylinder when in the closed position, as seen in FIG. 2A. In other examples, the profile of the closed adjustable rod structure can be up to 16 mm. A length of extension portion 18 as shown in FIGS. 2A-F is approximately equal to a length of rods 10. Extension portion 18 extends in a proximal direction from and is centered on the same longitudinal axis as insertion portion 17. At the proximal end of extension portion 18 (i.e., the end of probe 16 furthest from insertion portion 17), a surface of extension portion 18 can be configured or otherwise contoured for attachment to external equipment, such as that used for neuro-monitoring (discussed more fully below).

The probe structure can be varied in many respects. In one example, the length of the extension portion of the probe can be shorter or longer than one or more of the rods. In other examples, the extension portion of the probe is shorter than the rods, but the overall probe is longer than the rods. In still other examples, the cross-sectional dimension of the base of insertion portion 17 can be smaller or larger than the combined cross-sectional area of the rods surrounding extension portion 18 of probe 16 (i.e., profile). In yet another example, extension portion 18 of probe 16 can be cylindrical as shown in FIGS. 2A and 2C, however, it can also be conical so that it includes an increasing or decreasing cross-section toward insertion portion 17. Surfaces of extension portion 18 and/or insertion portion 17 that are adjacent to and face rods 10 can also include surface features so that the rods can nest into the probe and vice versa. Additionally, it is contemplated that the extension portion of the probe can have a square, rectangular, polygonal or other cross-sectional shape, as described in greater detail below. In other examples, the adjustable rod structure includes gaps between rods and between the rods and the probe when in the closed position. In such configurations, the profile of the rods in the closed position can be the same, larger or smaller than the profile of the insertion portion of the probe.

Probe 16 as shown can be a single construction or it can be assembled from components or modules, such as separate extension 18 and insertion 17 portions that are physically connected together. For instance, male-female threaded connections can be used to connect the components together either before or during surgery. Of course, other forms of interconnection between probe components are also contemplated. Probe 16 may be manufactured from a variety of biocompatible materials, such as metal materials like titanium or stainless steel, or polymer materials like PEEK. The material of the probe can also be dictated by its use, such as a polymer/metal composite for use with neuro-monitoring equipment, as described below.

Rods

Figure 38:
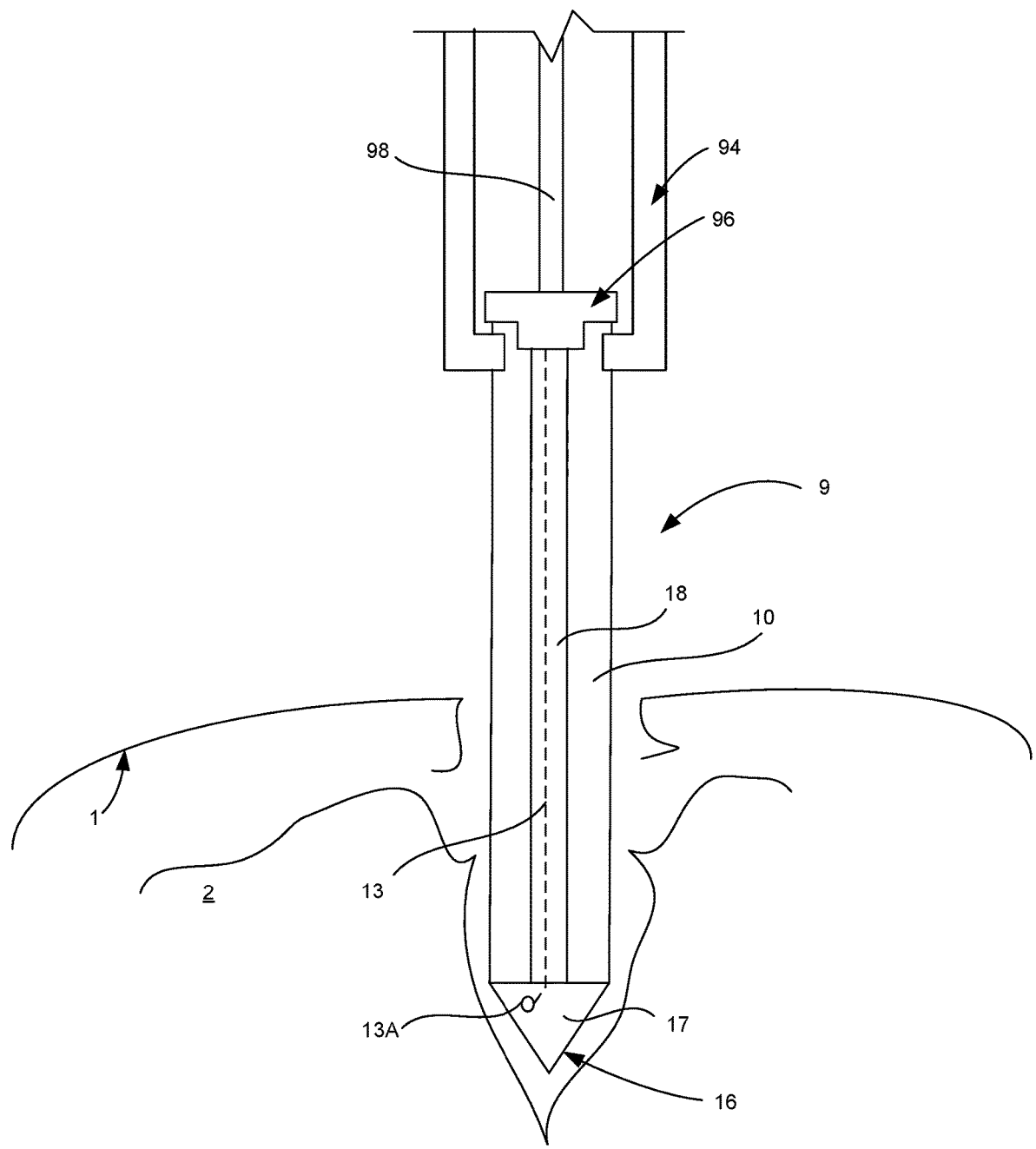
FIGS. 38-43 depict different steps in the use of the system shown in FIG. 1.

As mentioned above, probe 16 is surrounded radially by rods 10. As best seen in FIGS. 2A-2D, four rods 10 surround probe 16 in a manner so that the rods are symmetrical about a central axis through a length of adjustable rod structure 9. Each rod is circular in cross-section and includes a common diameter. Maintenance of the adjustable rod structure in a closed position is accomplished by application of a stabilizing force to outer surfaces of the rods that is sufficient to hold each rod in position surrounding the probe. For example, a closed position of adjustable rod structure 9 is maintained by holding an outer perimeter of rods 10 and probe 16 together by hand. In another example, shown in FIGS. 1 and 38, a closed position of adjustable rod structure 9 is maintained by holding an outer perimeter of rods 10 and probe 16 together with a holding element 96. Holding element 96 keeps the rods and probe substantially fixed with respect to one another in a closed position so that adjustable rod structure 9 can be transported and/or inserted into a patient as a unitary construct (FIGS. 1 and 38). As shown in FIG. 1, holding element 96 is connected to a handle 98 for use in positioning holding element 96. Although not shown, holding element 96 includes holes with sizes corresponding to rods 10 so that holding element 96 is disposable over rods 10. In this manner, holding element 96 resembles a cylinder with multiple chambers, similar to a cylinder of a revolver. An example of the holding element includes a sterile plastic cap with a flat base and a plurality of tubular extensions extending therefrom, extensions for the rods being shorter than an extension for the probe and each extension closed at one end by the base. The cross sectional area of the holding element in this example would match the profile of the adjustable rod structure in the closed position. Further, to lock holding element 96 to rods 10 and probe 16, a bayonet structure is used as a lock and release mechanism. The bayonet structure (not shown) is placed on corresponding surfaces of (1) rods 10 and probe 16 and (2) holes (not shown) within holding element 96. Other lock and release mechanisms can also be incorporated into the combined structure as known in the art. In addition to holding element 96, a clamp 94 can also be used to advance adjustable rod structure 9 into the body either with holding element 96 or separately. The rods and probe can further be adapted to engage with holding element 96 at a distal or proximal end of the rods.

Figure 2F:
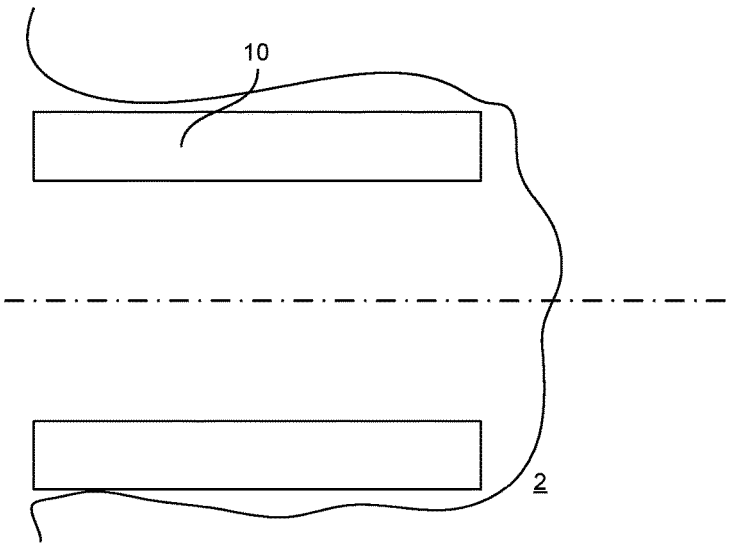

Rods 10 are also configured so that a device, such as a retractor as described further below, can be engaged thereto and operated to retract rods 10 away from probe 16 to create an opening, also referred to as a portal, therebetween. FIGS. 2C and 2D illustrate adjustable rod structure 9 in retracted positions. In particular, adjustable rod structure 9 is configured to retract at least to the extent shown in FIG. 2D, so that a space between rods 10 is wide enough to pull probe 16 through the opening created (FIG. 2F). A retractor can be attached to the rods once fully advanced or prior to initial insertion. When attached prior to insertion, the retractor remains engaged to the rods as the rods are advanced toward the target anatomical location.

The rods are further configured so that any material 2, such as tissue or muscle, surrounding the rods is held separated by the rods in the retracted position, as shown in FIG. 2C. Thus, the rods need to be of a suitable size and material to provide for the necessary strength to retract the tissue. Given that rods 10 can be provided in various lengths (discussed below), this can vary between longer and shorter rod constructs. Each rod is also engineered to withstand a certain amount of deflection under loading. Put another way, the properties of the rod provide sufficient elastic flexibility to withstand deflection that can result from tissue bearing on the rods during use without reaching yield under the highest possible loads. The maintenance of below yield stresses on the rods ensures that the rods return to their original shape once loads are removed, and thus increases the life cycle of the rods. Flexibility in the rods as described above is determined as a function of the rod length, its cross-sectional area and material properties of the rod. Properties of the tissue that bears on the rod during advancement of the adjustable rod structure may also be considered in determining rod properties for purposes of manufacture. As a result of the flexibility of the rods being a design consideration of the present invention, differences in one of the above variables for a rod can change the value for another variable. For example, it is possible that a diameter of the rods can vary based on the length of the rod so that a desired flexibility is achieved for both (i.e., same flexibility for each rod). An example of flexible rods is described in U.S. Pat. No. 8,992,558, the disclosure of which is hereby incorporated by reference herein. Exemplary materials for rods 10 include those described above for probe 16. Other examples of rod material include carbon fiber reinforced metal.

The rods can be varied in many respects. As described above, the rods can be different lengths with respect to each other. The length of each rod can be determined based on the relevant anatomy for an intended surgery. For example, where a target anatomical surface is convex in shape, one side may be closer to the point to the point of entry than the other. Respective rod lengths of the adjustable rod structure can be made to reflect this difference to optimize the effectiveness of the portal created. In a similar manner, one or more of the rods can be a different length relative to the probe. In other examples, the cross-section of the rods and probe can vary with respect to each other in any number of ways. In further examples, a bayonet structure is included where the structure only exists on certain holes in the holding element and on certain rods so that at last some rods are not part of the bayonet structure. This may be advantageous in certain applications where locking of certain rods is not desired. In some examples, the rods can have varying cross-sectional size along their length so that when combined with the probe, the adjustable rod structure has a tapering shape. These rods with varying cross-sectional size can also be included with a similarly varying probe. For example, the rods can have a cross-sectional size decreasing in a distal direction while the extension portion of the probe has a constant cross-section. In another example, both the rods and extension portion of the probe can have a decreasing cross-section in a distal direction. In yet another example, the cross-section of the rods is constant in a distal direction while the extension portion of the probe has a cross sectional size that increases in a distal direction toward the probe tip.

Patients are of various sizes, and therefore, rods and probes with varying lengths are contemplated. For instance, rods 10 and probes 16 can be provided in small, medium and large sizes, with a length range between approximately 30 mm for the small size to approximately 170 mm for the large size. Of course, these are just examples and various sizes within this range can be included as part of a kit, described in greater detail below.

Other features can also be included in one or more rods 10. For instance, the rods may include sensors for use in neuro-monitoring procedures, tracking devices, markers such as LEDs, as well as physical features (not shown) such as indentations, notches, grooves or protrusions configured to correspond to features on retractor 50 and/or the below discussed ring elements. Such features enhance securement between the rods and the retractor and/or ring and may also improve control when adjusting the position of rods relative to the retractor and/or ring.

Additional Elements: K-Wire and Neuro-Monitoring

Figures 20A, 20B:
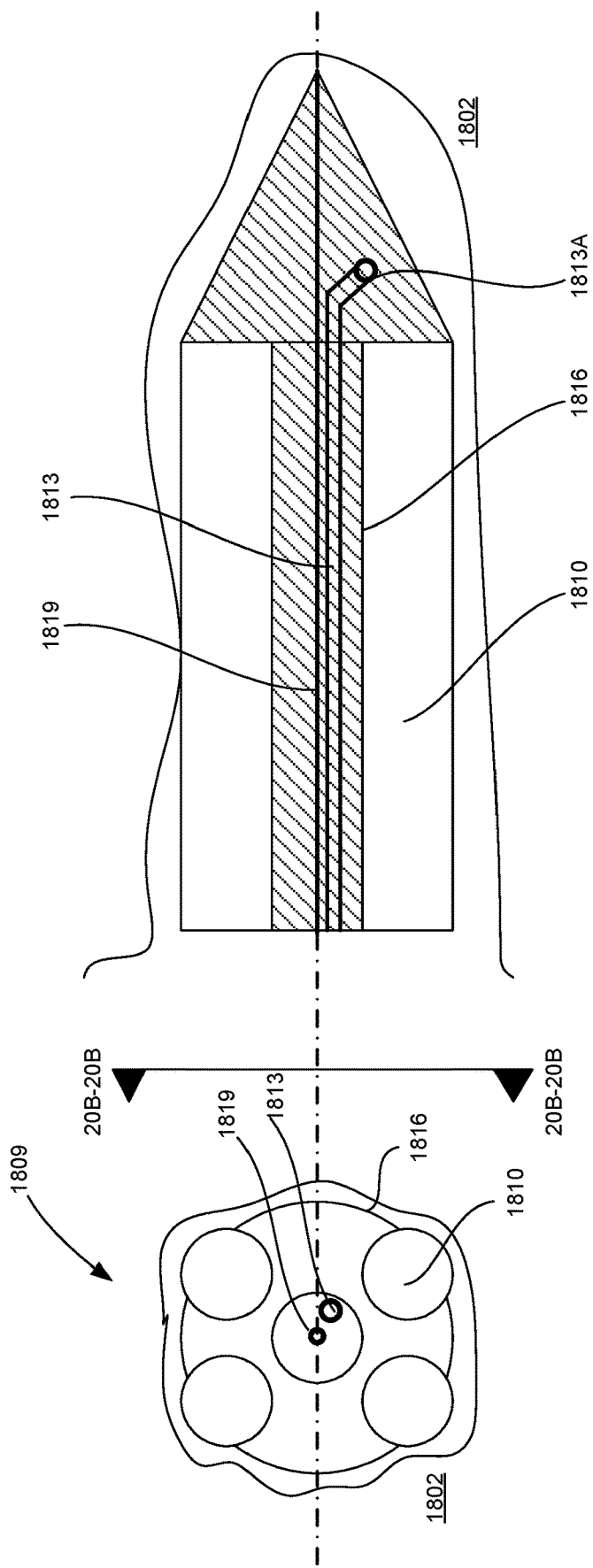
FIGS. 20A and 20B are rear facing and side views of an adjustable rod structure according to yet another embodiment of the present invention.

In certain embodiments, adjustable rod structure 9 may be configured to advance over k-wire or y-wire that guides the structure to a target site within the body. While k-wires are widely known, an example of y-wire is described in U.S. Pat. No. 8,545,531, the disclosure of which is hereby incorporated by reference herein in its entirety. FIGS. 20A and 20B illustrate an adjustable rod structure 1809 that is so configured. As shown, probe 1816 is cannulated so that it can receive wire 1819. Additionally or alternatively, a rod 1810 of adjustable rod structure 1809 can also be cannulated in the same way as the probe 1816. Probe 1816 can further be varied so that it is cannulated 1813 to incorporate structures that aid in a neuro-monitoring procedure. In general, neuro-monitoring technology is used to detect the proximity of nerves to a sensor. Here, for instance, as best shown in FIGS. 20A and 20B, probe 1816 includes a neuro-monitoring electrode 1813 disposed in a cannulation of probe 1816. Electrode 1813 is shown offset from a longitudinal centerline of probe 1816. While wire is shown situated along the longitudinal axis of probe 1816, other embodiments could include electrodes placed differently. For example, cannulations for electrodes can be in locations on probe 1816 or rods 1810 other than those shown in FIGS. 20A and 20B. In addition, electrode 1813 can also be insulated and disposed external to the probe 1816 and rods 1810. In any event, the offset nature of neuro-monitoring electrode 1813 allows for an exposed sensor 1813A located at a distal end of probe 1816 to rotate as the probe rotates. For many neuro-monitoring applications, movement of the sensors is used to obtain readings to detect the proximity of nerves in multiple directions. Sensors 1813A as contemplated herein are adapted so that an external controller (not shown) can be calibrated to read measurements by the sensor at any time during advancement of the adjustable rod structure. Although only a single electrode 1813 is shown in FIG. 20, it is also contemplated that two or more sensors can be included on the probe 1816. The inclusion of multiple electrodes may allow for the determination of direction with respect to nerve location. Examples of nerve detection as contemplated herein include electromyography ("EMG"), described, for example, in U.S. Pat. Pub. No. 2010/0241129, mechanomyography ("MMG") described, for example, in U.S. Pat. Nos. 8,343,065, 8,343,079, 8,517,954, 8,882,679, 8,855,822, 8,892,259, 8,942,797, 8,979,767, 8,983,593, 9,039,630, 9,084,550 and 9,301,711, and U.S. Pat. Pub. Nos. 2015/0051506, 2015/0051507, 2015/0088029, the disclosures of which are hereby incorporated by reference herein, and ultrasound described, for example, in U.S. Pat. Pub. Nos. 2016/0183913 and 2016/0242736, the disclosures of which is hereby incorporated by reference herein in their entirety, among others. In one example of MMG, an accelerometer is positioned to be in communication with a muscle so that when a device, such as the adjustable rod structure, is advanced into the body toward a target anatomical location, the accelerometer can provide output indicating the proximity of the adjustable rod structure to a nerve. In one example of ultrasound neuromonitoring, a transducer is disposed on the probe and is configured to launch sound pulses into tissue. The sound of the reflection from the part of the body contacted by the pulse can indicate whether such sound is originating from tissue, nerves, or other distinct anatomical structures.

In still further embodiments, the probes and/or rods can themselves be configured for use with a neuro-monitoring system. For instance, instead of including a cannulation for an electrode or the like, the rods and/or probes could be constructed of a combination of polymer and metallic material. The latter may operate as an electrode, while the former may serve as an insulator. Thus, only a portion of the metallic material (for instance, at the ends of the probe) could be exposed. This serves essentially the same purpose as the above discussed electrode. Of course, variants may include probes and/or rods only having a partially composite structure while the remainder of the probe and/or rod is manufactured from a non-composite metal. For example, the bullet shaped tip of the probe can be a composite material while the extension can be metallic.

Other Embodiments of Probe/Rod

Figure 3A:
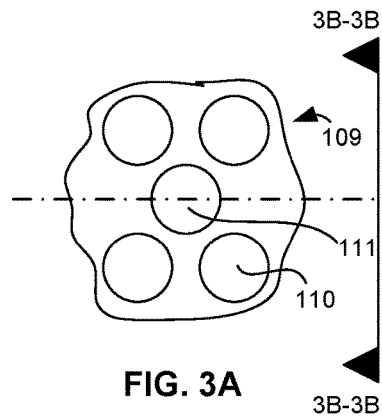
FIGS. 3A and 3B are rear facing and side views of an adjustable rod structure according to another embodiment of the present invention.
Figure 3B:
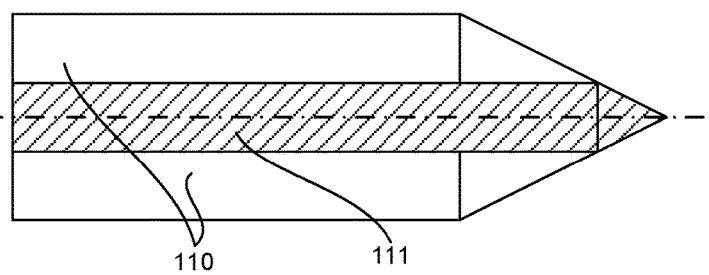

Different embodiments of adjustable rod structures are shown in FIGS. 3-19. Rods, and probes where applicable, of these embodiments are manufactured from various materials, such as those described above. Particular materials for individual rods and probes within an adjustable rod structure can vary and such determinations are a matter of design choice. FIGS. 3A and 3B illustrate a rod structure 109 having a probe 111 without a tapered insertion portion in the closed position. In addition to probe 111, rod structure 109 includes four rods 110, all having a similar or equal circular cross section over a proximal portion of their length. Each rod 110 further includes a taper towards a distal end, as shown. The taper is shaped so that an outward facing portion of the rod surface tapers inward, and in this way, the overall cross section of adjustable rod structure 109 becomes smaller toward the distal insertion end. Probe 111 maintains a circular cross section through most of a length of adjustment structure 109 and only tapers at the extreme distal tip, where it tapers to a point, as shown. Over an extreme distal end of the length of the tapered portion, the profile of rod structure 109 is solely comprised of probe 111.

Figure 4A:
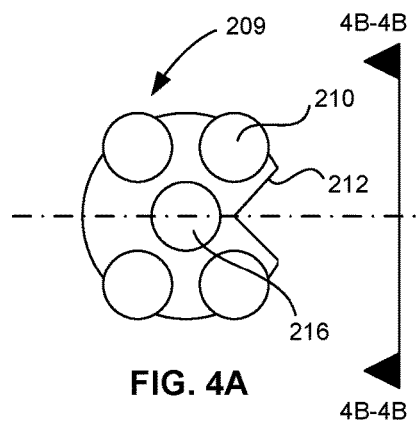
FIGS. 4A and 4B are rear facing and side views of an adjustable rod structure according to another embodiment of the present invention.
Figure 4B:
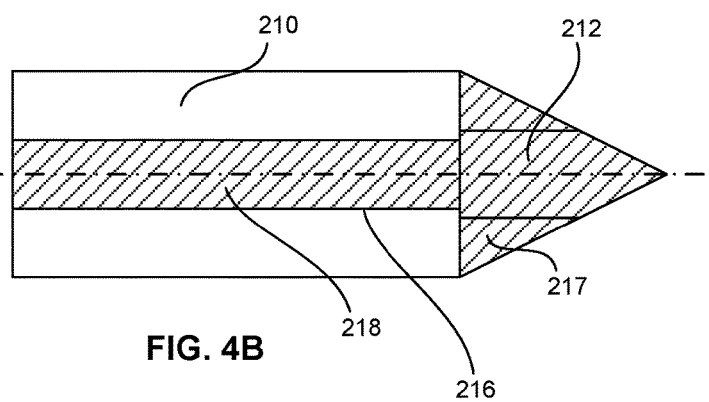

FIGS. 4A and 4B illustrate another embodiment of an adjustable rod structure 209. This structure includes four rods 210 and a probe 216. Rods 210 as illustrated are the same as rods 10 described above. Probe 216 includes an insertion portion 217 and an extension portion 218. The insertion portion 217 further includes a cut portion 212 defined by two non-tapering planar surfaces (best shown in FIG. 4A). In other words, cut portion 212 is a groove in insertion portion 217 of probe 216 and is configured to leave space within a profile of adjustable rod structure 209 so that an element, such as a fixation post described in greater detail below, can be inserted into the space as a step of one embodiment of a method. The groove is also of sufficient size so that a finger of a surgeon can be disposed therein when adjustable rod structure 209 is positioned inside the body.

Figure 5A:
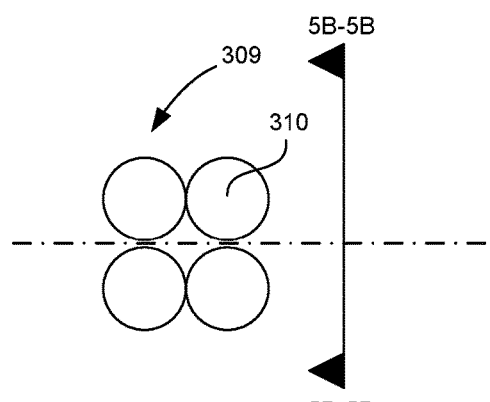
FIGS. 5A and 5B are rear facing and side views of an adjustable rod structure according to another embodiment of the present invention.
Figure 5B:
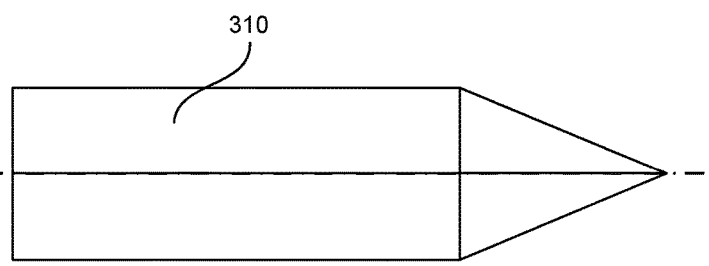

FIGS. 5A and 5B illustrate a four rod adjustable rod structure 309 in a closed position. Each rod 310 includes the same or similar circular cross-section and tapered tip. In the closed position, the taper of each rod tapers inward so that each terminates at approximately a common point at an insertion end of the adjustable rod structure 309.

FIGS. 6A and 6B illustrate another embodiment of adjustable rod structure 409 including four rods 410 and a probe 416 in a closed position. Rods 410 are positioned in a symmetric manner surrounding a center of the adjustable rod structure cross-section, and each rod 410 includes a cone-shaped tip 412 (FIG. 6B) at its distal end adjacent to and facing a back surface of a tapered insertion portion 417 of the probe 416. Tips 412 are cone shaped so that rods 410 are configured to anchor to a target site, such as an intervertebral disc, when fully inserted into the patient. In variants, tips can include other shapes that taper to a distal end. As shown, the rods 410 and an extension portion 418 of the probe 416 all have a circular cross-section of the same diameter.

Figure 44A:
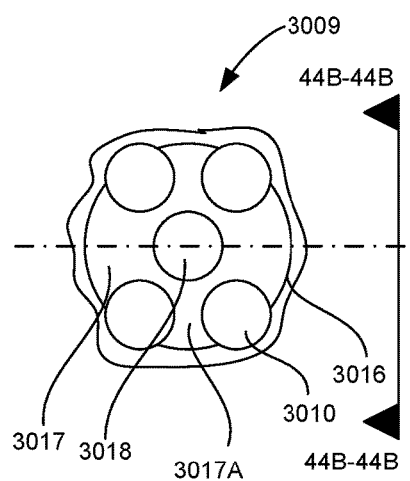
FIGS. 44A and 44B are rear facing and side views of an adjustable rod structure according to another embodiment of the present invention.
Figure 44B:
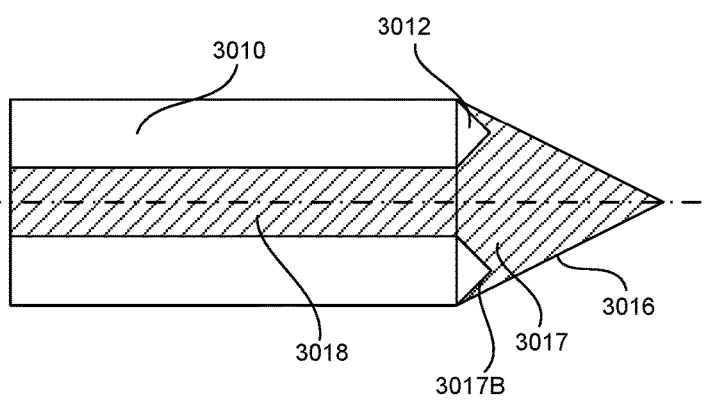

In a variant of the embodiment shown in FIGS. 6A and 6B shown in FIGS. 44A and 44B, rods 3010 are longer than extension portion 3018 of probe 3016. Insertion portion 3017 of the probe includes cavities 3017B on its bottom surface 3017A shaped to correspond to rod tips 3012 which are disposable therein (FIG. 44B). Tips 3012 of rods 3010 as shown are conical, however, it is contemplated that tips of other shapes can be included in a similar manner in conjunction with a probe having corresponding surface features to allow such tips to be disposed in the probe. In further variants, these principles can be applied in the opposite manner. For example, the tips of the rods can instead include cavities tapering into a body of each rod, and a corresponding bottom surface on the insertion portion of the probe can have protrusions to match the cavities in the rods. In yet another variant, the adjustable rod structure can include more than one type of rod where at least one rod includes a tip corresponding to a cavity in the probe and at least one rod has a flat distal end matching a planar portion of a bottom surface of the insertion portion of the probe, such as the rods of FIGS. 2A-2F.

FIGS. 7A and 7B illustrate yet another embodiment of a four rod and probe adjustable rod structure 509. As seen in the side view of structure 509, a distally facing end surface 512 of rods 510 is contoured along an arc. The arc is oriented so that rods 510 have a concave end surface that mates with a convex bone surface, such as the vertebrae of the spine, when adjustable rod structure 509 is retracted into an open position. As shown, rods 510 and an extension portion 518 of probe 516 all have a circular cross-section of the same or similar diameter. Of course, in variants, the contour of the bottom surface of rods 510 can be convex and can otherwise vary from the end surface 512 shown to suit the anatomy of a particular patient or group of patients or even to cooperate with different anatomical structures.

FIGS. 8A-8D illustrate a three element adjustable rod structure 609. As shown in FIG. 8A, two of the rods 610 are of the same structure, while a third rod 611 traversing a width of rod structure 609 includes similar geometric features but is wider and includes a larger cross-section than rods 610. Thus, identical rods 610 have a combined profile slightly larger than a profile of rod 611, as shown. Inner surfaces of each rod are planar so that when adjustable rod structure 609 is closed, as shown in FIGS. 8A and 8B, the surfaces of the respective rods press together and are flush with one another, leaving only a nominal amount space between each if any space at all. Generally, an outer surface 610A, 611A of each rod 610, 611 forms part of a circular surface so that when the rods are closed, rod structure 609 is largely cylindrical, but with a tapered distal end. As shown, the tapered end is conical and is formed from tapered end portions of each rod 610, 611. As best shown in FIGS. 8A-8D, rods 610, 611 also include a circular hole 613 that is entirely within a cross-section of each rod and is configured to provide a pathway to distribute lighting into a distal region of adjustable rod structure 609. Of course, differently shaped/sized holes can be provided for different purposes. Each rod 610, 611 also includes an engagement feature 614, 615 having neck portions 614A, 615A and arms 614B, 615B flaring outward in a lateral direction from neck 614A, 615A, respectively. An outer surface of arms 614B, 615B forms a partial circular surface so that the outer surface of the combined engagement features represents a second profile for adjustable rod structure 609 outside of the generally circular outer surface of rods 610, 611 themselves. A shape of the engagement features 614, 615 is tailored so that engagement with lighting tools, shims, retractor extensions, and other devices used during surgery, is possible and if already possible, improved. Each rod 610, 611 is configured to be retractable in tandem with each other, as well as independently in a linear or radial direction or in a direction that is a combination of both. Each rod can also be rotated either independently or in tandem with one or more of the other rods. As in other embodiments, adjustable rod structure 609 can be manufactured from metal, polymers, or a combination of both. Examples include a structure where the engagement features are metal and the rods are a polymer, a structure where the engagement feature is metal with plastic arms, or a structure where the rods are a composite of metal and polymer to accommodate neuro-monitoring. In another variant, each of the three rods includes a common cross-section. In yet another, all three are of a different size. In some variants, the hole in one or more rods can be oval, square or another shape. In addition, one or more rods may not have a hole at all.

In other variants, the hole is only disposed in the profile of the adjustable rod structure 609 over part of its length, with at least another part external to the circular perimeter. For example, the hole can be on the interior of the profile at a proximal end of a rod, extend within the profile in a distal direction, and then alter trajectory so that it continues outside of the rod as a tube to an end point proximal to the tapered tip. In other variants, the adjustable rod structure can include four or more rods with cross sectional shapes as described. In yet another variant, the rods of the adjustable rod structure may include a chamfer or notch on one corner facing the other two rods. In this way, when the rods are brought together into the closed position, a gap, or hole, remains between the three rods at a center of the adjustable rod structure profile. This space can be configured so that k-wire, y-wire or the like may be placed therethrough.

Figure 9A:
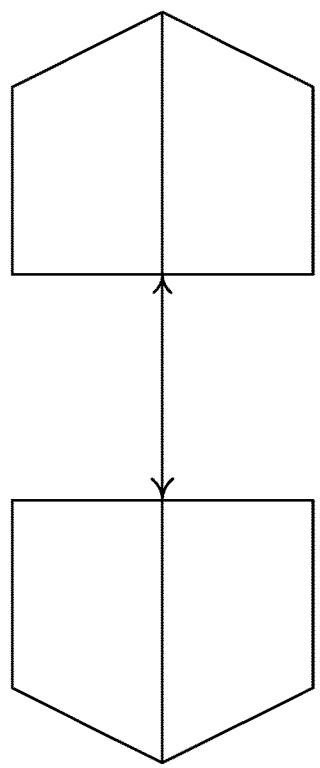
FIG. 9A is a rear facing view of an adjustable rod structure according to another embodiment of the present invention in a first position.
Figure 9C:
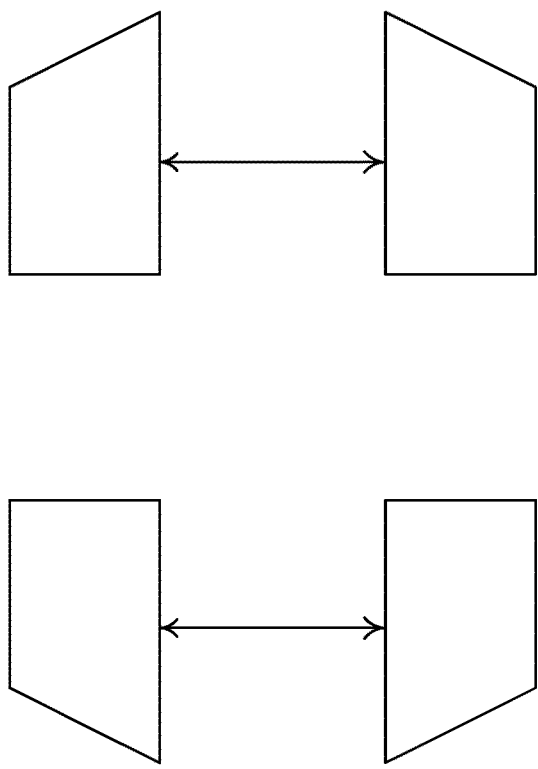
FIG. 9C is a rear facing view of the adjustable rod structure shown in FIG. 9A in a third position.
Figure 9B:
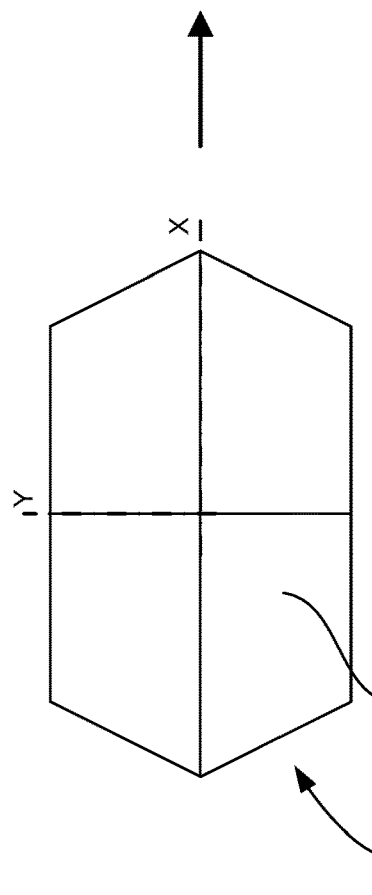
FIG. 9B is a rear facing view of the adjustable rod structure shown in FIG. 9A in a second position.
Figure 9D:
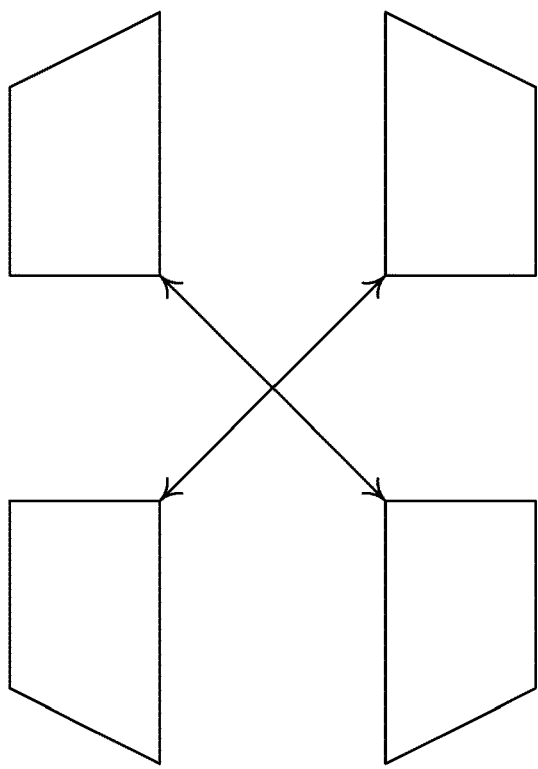
FIG. 9D is a rear facing view of the adjustable rod structure shown in FIG. 9A in a fourth position.

FIGS. 9A-9D illustrate another embodiment of an adjustable rod structure 709 that includes four polygonal rods 710. As shown, the combined structure 709 forms a hexagon shaped profile. The rods 710 are configured so that each can be retracted in the x-axis, y-axis or diagonal axes, as best shown in FIGS. 9C, 9D and 9B, respectively. In a variant, the adjustable rod structure 709 can be another polygonal shape, such as a pentagon, with each rod having a common cross section. In other variants, the adjustable rod structure 709 can include at least two rods having different cross sectional shapes.

Figure 10B:
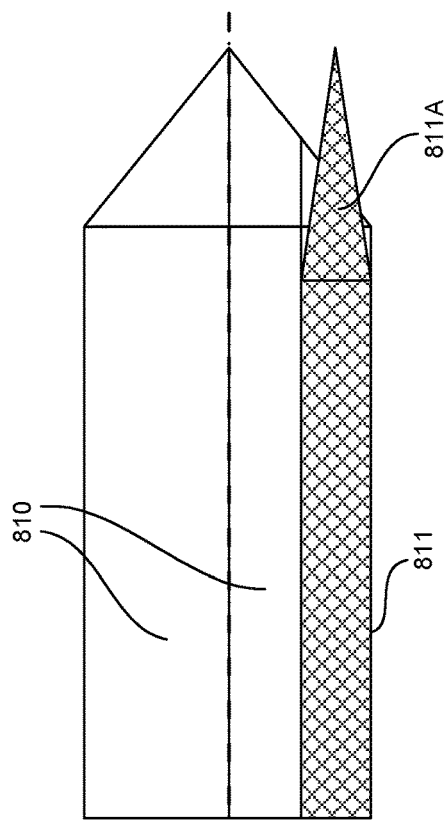
FIG. 10B is a rear facing view of the adjustable rod structure shown in FIG. 10A.
Figure 10A:
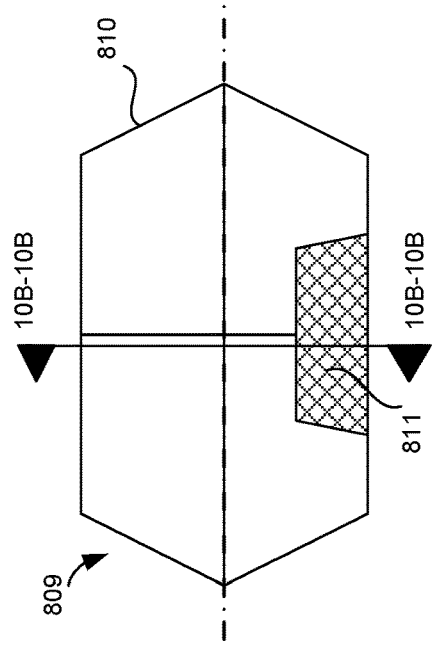
FIG. 10A is a rear facing view of the adjustable rod structure according to another embodiment of the present invention.

Illustrated in FIGS. 10A and 10B is another embodiment similar to that shown in FIGS. 9A-9D in that it includes a polygonal shaped adjustable rod structure 809 with four rods 810. However, it also includes a fixation post 811. In a closed position, rods 810 and fixation post 811 complete a hexagonal profile, as shown in FIG. 10A. A distal end of adjustable rod structure 809 terminates in a tapered end, as shown in FIG. 10B. However, the tapered end is based on the structure of combined rods 810 and excludes fixation post 811, as best seen in FIG. 10B. Fixation post 811 is independent of rods 810 and is configured to engage or become fixed to soft or hard tissue. For example, fixation post 811 can engage a vertebral body or disc located between vertebral bodies. An arrow shaped tip 811A at a distal end of fixation post 811 is a mechanism for engagement between post 811 and the tissue and is shown in FIG. 10B. In some variants, the tip can be threaded, kneaded or have other engagement features. In addition, the tip can be conical, as shown in FIG. 10B, for example, or it can be another shape such as a dome, pyramidal, and so on. In some variants the fixation post is monolithic. In others, it is not monolithic. In one example of a non-monolithic construction, a body of the fixation post is cylindrical and hollow and the tip includes a conical tip structure with an extension portion extending therefrom sized to fit within the hollow space of the fixation post body. In this manner, the fixation post is configured so that once the combined body and tip of the fixation post have been fully advanced to a target site, a proximal end of the extension portion of the tip can be accessed by a user to screw the tip into a target anatomical surface at the target site. Because there is negligible restraint on relative rotational movement between the body and tip components, the body will remain static as the tip is rotated via the extension. In yet another embodiment, two or more fixation posts can be included as part of an adjustable rod structure. In still further embodiments, the system can include at least one monolithic fixation post and at least one non-monolithic fixation post, such as a fixation post including a body and a tip component.

Figure 11B:
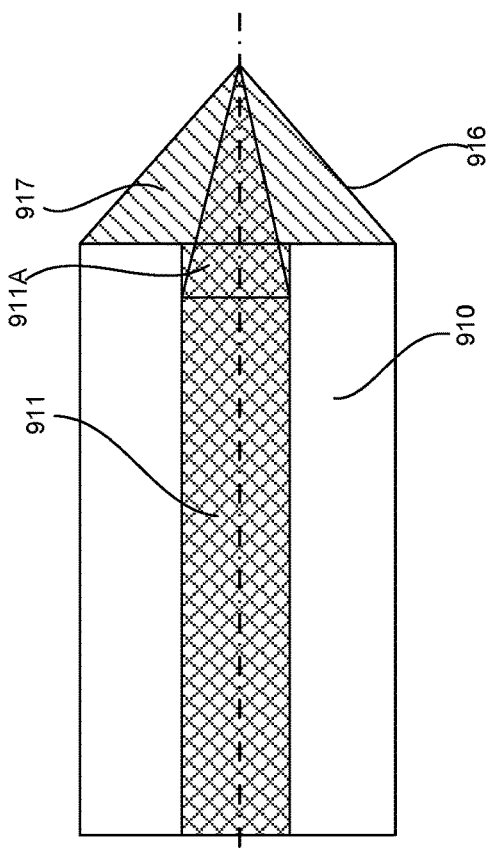
FIG. 11B is a rear facing view of the adjustable rod structure shown in FIG. 11A.
Figure 11A:
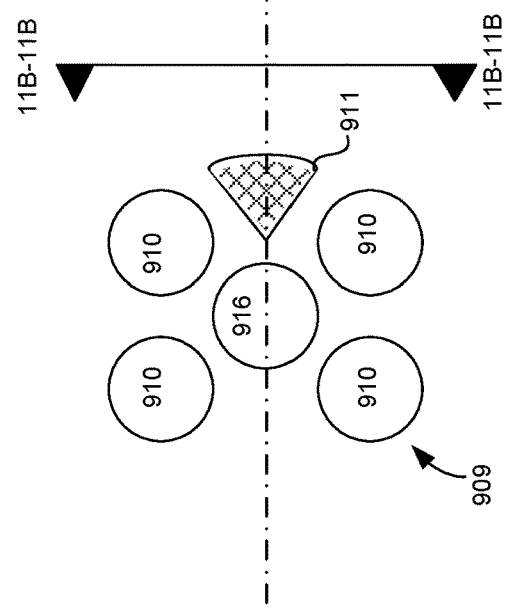
FIG. 11A is a rear facing view of the adjustable rod structure according to another embodiment of the present invention.

Another embodiment that depicts an adjustable rod structure 909 with a fixation post is depicted in FIGS. 11A and 11B. A probe 916 with a tapered insertion end 917 is surrounded by four rods 910. To one side of the probe 916 is a fixation post 911, as shown in FIG. 11A. Similar to the above, the fixation post 911 includes a cone shaped or pointed distal end 911A (FIG. 11B) and is configured so that it is movable independent of the other elements of structure 909. Fixation post 911 is configured so that it is securable to an intervertebral space, or other anatomical structure. In a variant, insertion end 917 of probe 916 can include a groove or recess (not shown) shaped to allow passage of fixation post 911. In this way, fixation post 911 may be inserted into the intended anatomical location prior to removing the probe 916 from the adjustable rod structure 909. Fixation post 911 is manufactured from materials such as those described above for the probe and rods. It is contemplated that fixation post 911 can be varied in the same ways as described above for fixation post 811.

Figure 13:
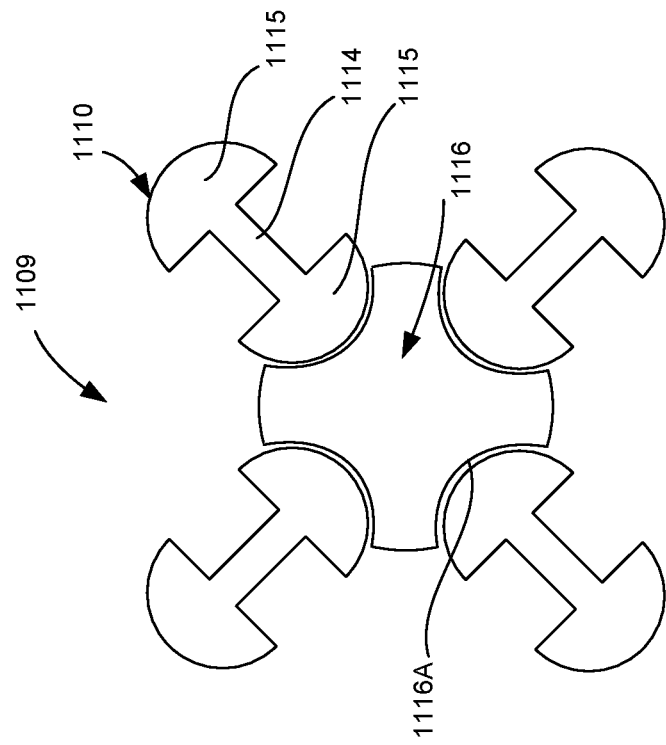
FIG. 13 is a rear facing view of an adjustable rod structure according to another embodiment of the present invention.
Figure 12:
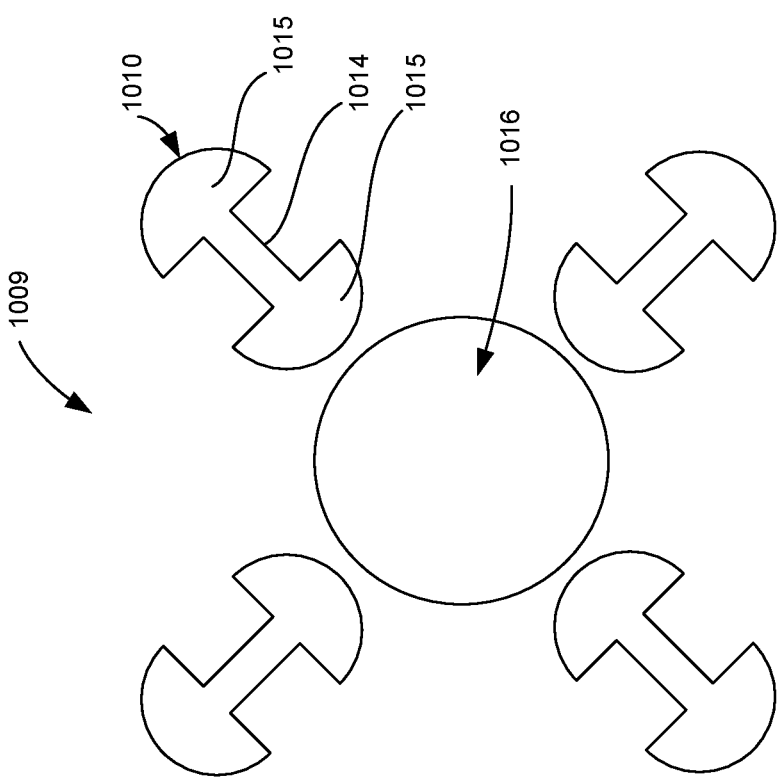
FIG. 12 is a rear facing view of an adjustable rod structure according to another embodiment of the present invention.

In another embodiment, rods of an adjustable rod structure are I-shaped, as shown in FIGS. 12 and 13. In the depicted embodiments, each group of I-shaped rods 1010, 1110 surrounds a probe element 1016, 1116, respectively. In FIG. 12, an adjustable rod structure 1009 includes a single probe 1016 and four rods 1010 of equal size. Probe 1016 has a circular cross section extending from a proximal end so that the probe is substantially cylindrical in shape. Towards a distal end of the probe, the surface tapers to a distal tip (not shown). Each rod 1010 has a narrow web 1014 and a wide flange 1015 at each end of web 1014, thereby forming the I-shape. Flanges 1015 are semicircular in shape when viewed in section and each flange 1015 is a mirror image of the other. The I-shape of rods 1010 provides strong flexural capacity (i.e., bending capacity) against loads bearing on the rods pushing the rods inwards, particularly where loads are distributed along a length of the rod. For example, when adjustable rod structure 1009 is advanced into muscle tissue and the rods are retracted, the tissue surrounding the rods bears on rods 1010 urging each rod inward.

In the embodiment of FIG. 13, a probe 1116 having indentations 1116A is included. Indentations 1116A are shaped to mate with a semicircular outer surface 1115 of rod flanges 1110. Although only visible in a sectional view, probe 1116 and indentations 1116A therein extend longitudinally in a distal direction over a portion of a length of probe 1116 and taper at a distal end to terminate in a tip. The indentations 1116A extend into a portion of the tapered portion of probe 1116 and fade into the tapered surface in the distal direction when the cross section of probe 1116 decreases in size to a point where it is smaller than the indentation surface (not shown). A profile of adjustable rod structure 1109 in a closed position is smaller than that of the adjustable rod structure of FIG. 12 as indentations 1116A on probe 1116 provide additional room for rods 1110 to be positioned closer to a centerline of the adjustable rod structure cross section. Thus, adjustable rod structure 1109 includes a minimal profile and has the advantage of improved strength in the rods through the I-shape of each. In addition, the extension of indentations 1116A into the bullet shaped end portion of probe 1116 improves ease of removal of probe 1116. It is contemplated in other variants of the above embodiment to include one or more rods that are a shape other than an I-beam, while the other rods include I-beam cross-sections.

Figure 14:
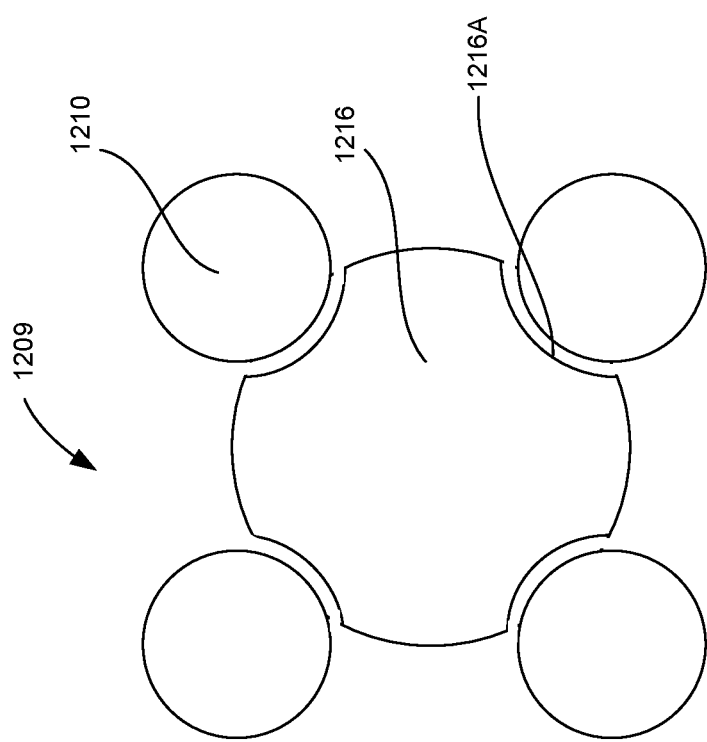
FIG. 14 is a rear facing view of an adjustable rod structure according to another embodiment of the present invention.

Other variations of the above embodiments are also contemplated. For example, an adjustable rod structure 1209 includes four circular rods 1210 having the same diameter surrounding a probe 1216, as shown in FIG. 14. Probe 1216 includes four indentations 1216A, each having a radius matching that of rods 1210, disposed in a symmetric manner around the cross section of probe 1216. In a closed position, as best shown in FIG. 14, each rod 1210 mates with a corresponding indentation 1216A so that the overall profile of the adjustable rod structure is smaller than it would be otherwise. Probe 1216 includes a tapered distal end (not shown). In a variant, the tapered distal end can comprise a taper commencing in rods 1210 and then proceeding distally into probe 1216 beyond ends of rods 1210.

Figure 15:
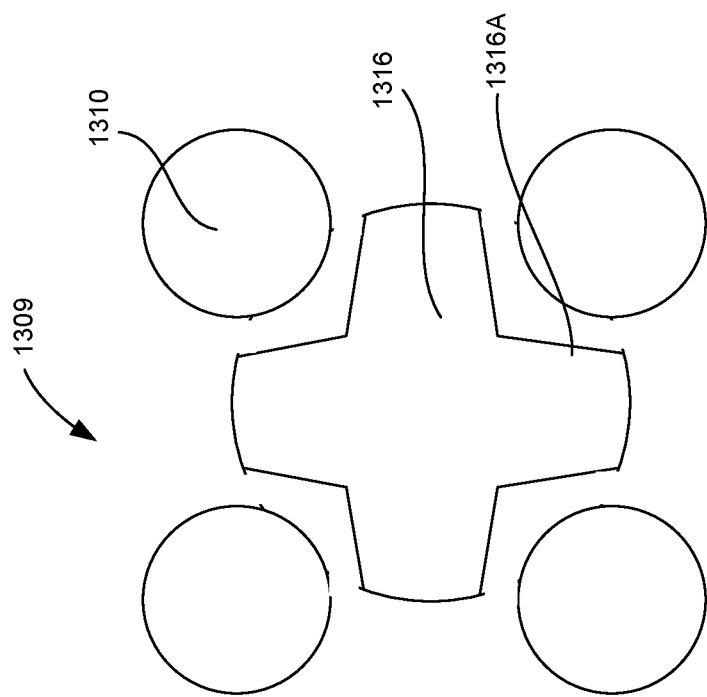
FIG. 15 is a rear facing view of an adjustable rod structure according to another embodiment of the present invention.

In another example depicted in FIG. 15, an adjustable rod structure 1309 includes a probe 1316 with indentations 1316A having a triangular section cut from an otherwise circular section probe element 1316. Each indentation 1316A includes two planar surfaces converging on a line extending from the proximal end of probe 1316 to a tapered distal end of probe 1316. As above, structure 1309 includes four rods 1310. In the closed position, rods 1310 correspond to indentations 1316A. The structure of probe 1316 in this embodiment can reduce the size of a kit as a larger variety of rod shapes can complement and correspond to the indentations in the probe than might otherwise be possible with other configurations. Thus, fewer probes are needed to complement a variety of rod shapes. For example, both square and circular rods can be positioned adjacent to indentations 1316A so that either corresponds with probe to create a minimal profile of structure 1309 in the closed position.

In other embodiments, the adjustable rod structure can have a wide variety of profiles based on a varying quantity, size and shape of the rods, with or without probes. Some examples of what is contemplated by the present invention in this regard are shown in FIGS. 16-19. As in the other embodiments described above, it is contemplated for each of the embodiments shown in FIGS. 16-19 that the adjustable rod structure can have various forms of a tapered distal end. For example, the tapered distal end can be bullet-shaped or it can be arrow-shaped with a pointed tip. In FIG. 16, an adjustable rod structure 1409 includes four rods 1410 and has an oval shaped profile in the closed position. In FIG. 17, an adjustable rod structure 1509 includes a probe 1516 and eight rods 1510 disposed radially surrounding probe 1516 in a symmetrical fashion. In a variant, probe 1516 can be substituted with a rod. In FIG. 18, an adjustable rod structure 1609 has an octagonal profile in a closed position. Each rod 1610 has the same five sided cross section, with rods 1610 being symmetrical about both x and y axes. In FIG. 19, an adjustable rod structure 1709 includes three rods 1710, 1711. As shown, rods 1710 have the same four sided cross section, while rod 1711 is somewhat smaller and has three sides.

The above embodiments may be varied in many respects. For example, the cross-section of the rods can be non-circular in shape (i.e., rectangular, oval or polygonal), as is shown in certain embodiments. Similarly, the cross section of the adjustable rod structure (i.e., the combined section of the rods) can be any shape, such as rectangular, oval, polygonal, and so on. The rods 10 can also include a tapering diameter so that the diameter tapers in a distal direction toward the distal (insertion) end or so that the diameter increases toward the distal end. In another example, the rods can include a telescoping or lengthening capability. Systems or kits with telescoping rods are advantageous in that fewer sizes (i.e., lengths) of rods would be required for use in an array of surgical conditions. In yet another example, the probe may be surrounded by any number of rods.

As in certain shown embodiments described elsewhere in the disclosure, the adjustable rod structure may also be comprised of rods without any probe element. For example, the adjustable rod structure can include five rods, where the combined rod structure forms an arrow shaped insertion end when in the closed position. In yet another example, the proximal end of the rods can include notches or divots spaced at approximately equal intervals. These surface features can be shaped to correspond with a retractor device to allow adjustment of the locked position of the rods relative to the retractor. Through the inclusion of notches or divots on the rods, it is possible to reduce the number of rod lengths necessary for inclusion in a kit. For example, providing rods with notches at specific interval (e.g., 5 mm intervals) could negate the need for rods with small, medium and large lengths in favor of just a one or two such sizes.

In other examples, the individual rods of an adjustable rod structure may vary. This variation can be differing diameters, differing shapes, cannulation and so on. For example, an adjustable rod structure includes five rods, where two have a diameter of 6 mm and the other three have a diameter of 8 mm. It is contemplated that other features of the rods may also vary rod to rod within an adjustable rod structure. In other examples, the position of the rods around a center of the adjustable rod structure can be asymmetrical. In other embodiments where two or more rods include the same cross-sectional shape at the proximal end of the adjustable rod structure, but have different features at the distal end, such as one being bullet shaped and the other not, indicators can be included on a proximal end face of the rods to identify and distinguish between them. For example, color coding can be used to signal to a surgeon whether a rod has a bullet shaped tip or whether it is cut orthogonally to its length at a distal end face. This can allow a surgeon to easily line up a given rod with a specific anatomical feature or in a specific orientation. Other indicators such as notches or dots can also be used. Indicators can also be used as a benchmark to adjust and align one or more of the rods. For example, to monitor rotation of a rod with a pointed end once it is engaged with an intervertebral disc. Indicators can be placed on the rods in many locations. For example, indicators can be placed on a proximal end surface of the rod or within the rod for measurement through medical equipment, such as an x-ray. The examples described here are merely illustrative and many other cross-sectional shapes, rod quantities, symmetry and so on are contemplated as within the scope of the invention. Also, the depiction and description of the insertion end of the adjustable rod structure as being arrow or bullet shaped is merely illustrative of one preferred embodiment. It is of course contemplated that for embodiments throughout the specification that the arrow or bullet shaped tip may be varied in a manner appropriate for tissue penetration using the knowledge of an ordinary artisan. For example, the insertion end can be a conical shape or have a pointed tip with a shape that is not specifically an arrow shape. The use of "tapered end" to describe the insertion or distal end of the adjustable rod structure throughout the specification contemplates the above possibilities and many others for a shape of a penetrating tip of the adjustable rod structure.

Ring Inserts

Once the rods of any of the above-discussed adjustable rods structures are opened via the use of a retractor (discussed below), the pathway may be maintained through the use of one or more rings or the like. For instance, FIGS. 21A-21D depict a series of rings 1920 that are advanced along individual rods 1910 of adjustable rod structure 1909, which can be in the form of any of the above-discussed rod structures. Each ring 1920 is configured so that it is insertable over rods 1910 of adjustable rod structure 1909. FIGS. 21B and 21D show the rings disposed over rods 1910 at proximal and distal positions, respectively. Thus, rings 1920 are adapted so that each can slide over a length of rod 1910. Although rings are shown as having a depth over a fraction of the rod length, rings can have a depth of an amount up to and above that of the rod length. They are also preferably rotatable with respect to rods 1910, as discussed below. Each ring 1910 includes a circular outer profile and extending from that profile, an engagement portion 1921. Engagement portion 1921 includes a narrow neck 1921A and arms 1921B extending in opposite directions from neck 1921A, as shown. An outer surface of arms 1921B of engagement portion 1921 includes a partial circular profile. The shape of engagement portion 1921 is configured so that tissue 1902 or other materials are held back when ring 1920 is rotated as shown in FIG. 21C so that engagement portion 1921 faces outward. Thus, rings 1920 can be inserted with engagement portions 1921 facing inward (FIG. 21B) and then individually rotated into place to push back tissue (FIG. 21D). The rings 1920 are made of a plastic material, although manufacture using other materials is also contemplated. Rings 1920 inserted over rods maintain a diameter of a portal opening while a retractor remains in place to hold the rods in their open position. In other embodiments as described below (e.g., FIGS. 22A-22B), the rings, once in position, can hold the rods in place and thus maintain a portal opening with or without the assistance of a retractor.

In a variant, rings 1921 can include additional engagement features configured for engagement with complementary features on rods 1910. Such features can be sized and positioned to control rotation and/or advancement of rings 1920. For instance, the rings could snap into place at different portions of the rod (e.g., at a distal end). Further, additional engagement features can be disposed at any location on the ring or distributed throughout. In other variants, the geometry of the engagement portion can be another shape deemed suitable for engagement to tissue expected to be encountered during surgery. In this and other embodiments, the rings can be manufactured in varying lengths so that a size best suited for a particular surgery may be used. For example, each ring can be 10 mm, 20 mm or 30 mm long, measured on an axis extending through holes of the rings. This is discussed in greater detail in the kit embodiments described below.

Figure 22A:
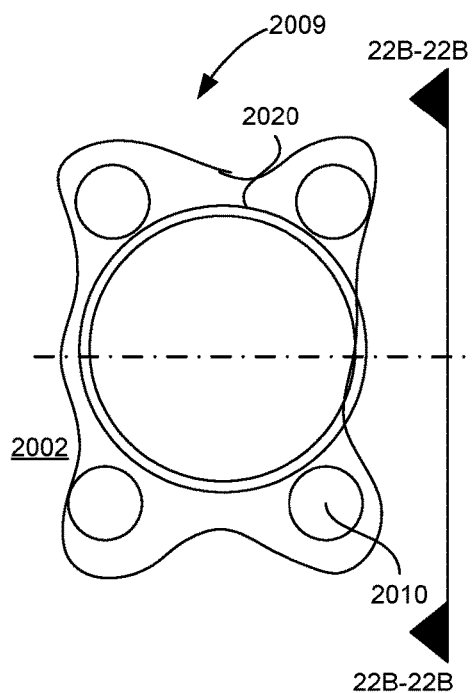
FIGS. 22A and 22B are rear facing and side views of a ring disposed between rods in another embodiment of the invention.
Figure 22B:
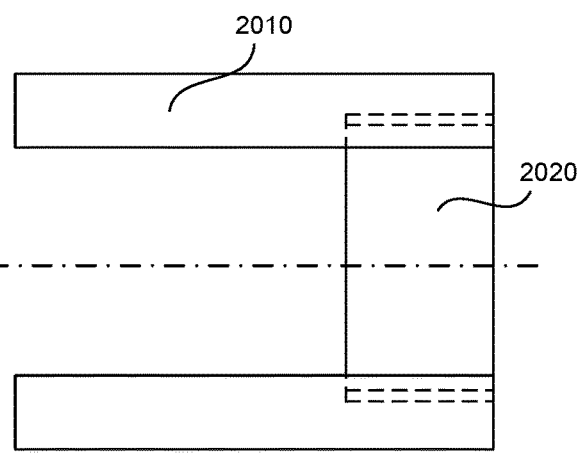
Figure 23A:
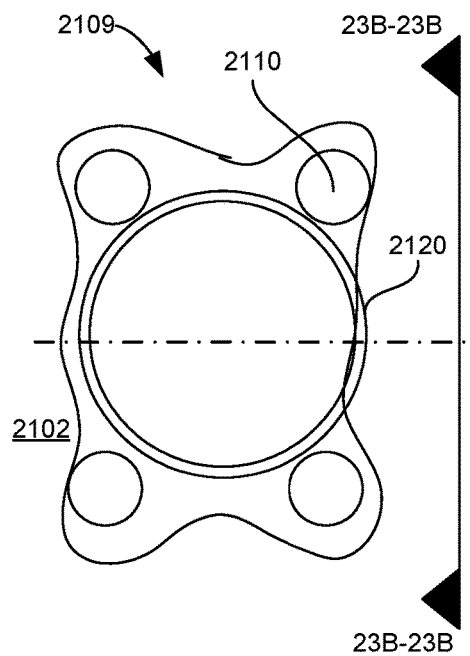
FIGS. 23A and 23B are rear facing and side views of a ring with a convex bottom surface disposed between rods in another embodiment of the invention.
Figure 23B:
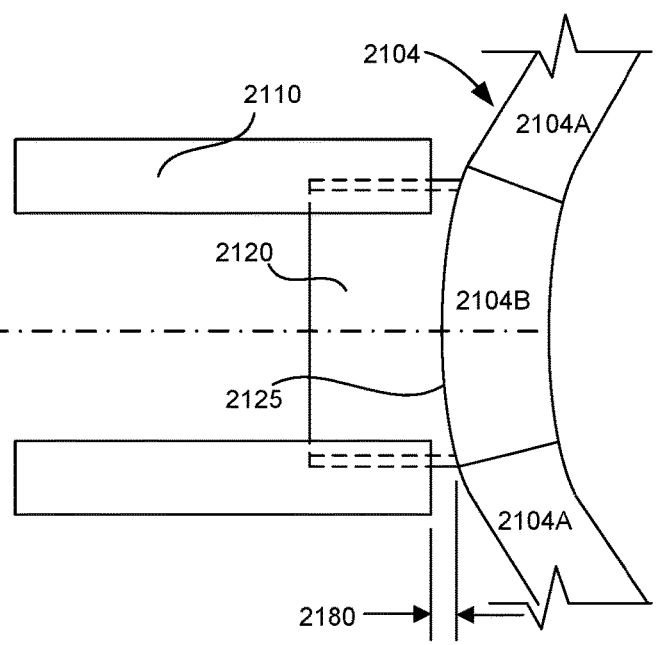

In another embodiment, a single ring 2020 is sized for insertion between rods 2010 when the rods 2010 are in the retracted position. FIGS. 22A and 22B illustrate four rods 2010 with a single ring 2020 disposed therein. Ring 2020 is a hollow tube with an opening sufficient for performance of an operation at an intended anatomical location in the body while ring 2020 is in position. Ring 2020 is manufactured so that an outer surface of the ring diameter contacts and holds rods 2010 when ring 2020 is positioned therebetween. This may entail the inclusion of depressions or slots formed on an outer surface of ring 2020 for receiving a portion of each of rods 2010. In another embodiment, a hollow tube ring 2120 (see FIGS. 23A and 23B) is similar to ring 2020, but includes a concave bottom surface 2125. Concave bottom surface 2125 of ring 2120 has an arcuate shape so that it can nest or otherwise mate with an intended anatomical location, such as an intervertebral disc 2104B between vertebral bodies 2104A. Of course, bottom surface 2125 may be tailored to cooperate with any anatomical structure or the like. In a variant, ring 2120 can have a depth so that ring 2120 abuts bone surface 2104B in a fully advanced position while simultaneously remaining engaged by rods 2110 which remain at a distance, or gap 2180, from the bone or disc surface. In this manner, gap 2180 between a distal end of rods 2110 and vertebral body or intervertebral disc 2104A, 2104B, is covered and protected by ring 2120, preventing tissue 2102 creep into the portal. The gap may be up to several millimeters over a portion of the ring depth. For example, it can be 0 mm or it can be up to 10 mm. Ring 2120 as shown in FIG. 23B is configured to perform with the aforementioned gap present while positioned proximal to a target anatomical location. In another variant of this embodiment, the gap may vary at different locations around the circumference of the ring. For example, the depth of the gap may be shorter on one side of the ring relative to the depth on the opposite side. Thus, the gap can be up to 10 mm on one side of the rod and another amount on the other side of the rod that is a function of the 10 mm value and a gradient of the vertebral body surface or a function of the 10 mm value and a radius of a curved surface of the vertebrae.

Figure 24B:
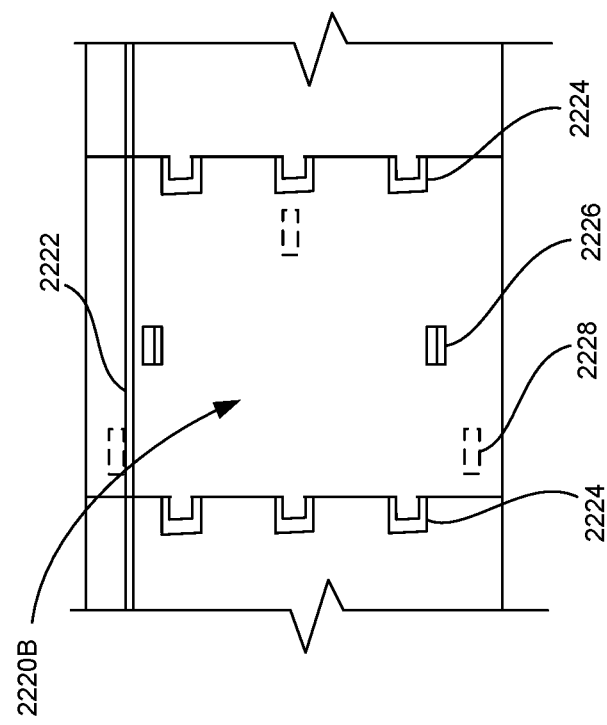
FIG. 24B is a close up partial interior view of a middle ring of the stacked rings of FIG. 24A showing an interior wall of the middle ring.
Figure 24A:
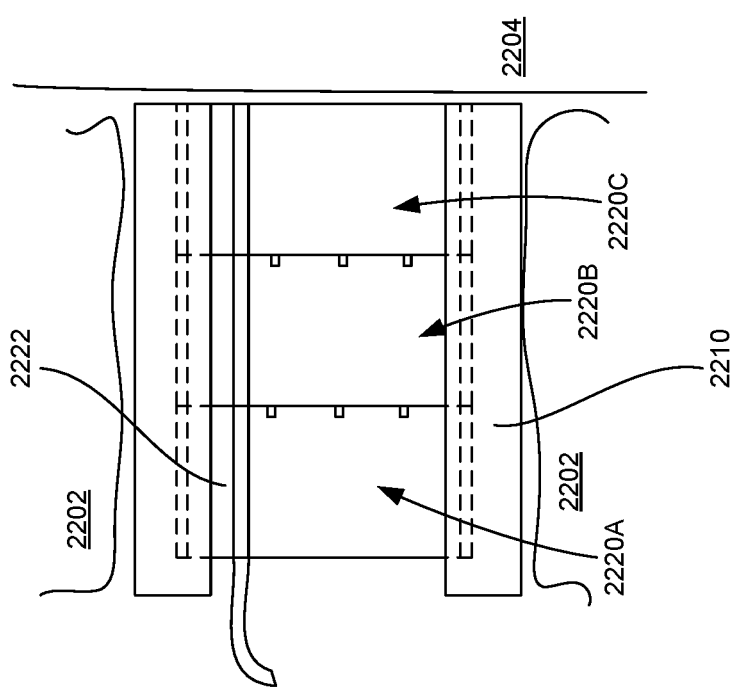
FIG. 24A is a side view of stacked rings disposed between rods in another embodiment of the invention.

In yet another embodiment, three rings 2220A, 2220B, 2220C are included as part of the system, where each ring is stackable as shown in FIG. 24A. As depicted in part in FIG. 24B, each ring has engagement features 2224 at roughly equal spacing around a rim of the ring to secure it to a corresponding engagement feature 2224 on an adjacent ring. For example, ring 2220B has engagement features on a top and bottom rim, as shown in FIG. 24B. The engagement features 2224 at either rim can be male or female. Some rings, such as those to be placed at an end of a stack, only have engagement features on one rim, while the other rim includes a flat surface. For example, ring 2220A has no engagement features on a top rim, as shown in FIG. 24A. In FIG. 24B, three engagement features 2224 are visible at the interface between rings, but it is contemplated that engagement features are placed as desired around a circumference of the ring. A tube 2222 for lighting is also shown affixed to the combined ring structure in FIGS. 24A and 24B. Tube 2222 can be, for example, a cannulated plastic tube with a wire (not shown) disposed therein. The wire extends to a location toward the distal end of rods 2210 and connects to a light, such as a light emitting diode ("LED"), and from that location light emanates. This ensures that the intended anatomical location is well lit, either through directed light focused only on the intended anatomical location or through light distributed over a depth of the opening of the adjustable rod structure measured from the proximal to the distal end of the rods, lighting an entire length of the opening spanning all three rings. Examples of lighting that may be included with the rings include that described in U.S. Pat. Nos. 7,946,982 and 9,206,947, the disclosure of both hereby incorporated by reference herein. Other lighting technology that may be included with the rings includes U.S. Pat. No. 9,429,746 and U.S. Pat. App. Pub. No. 2016/0338795, both assigned to Invuity, Inc., hereby incorporated by reference herein in their entirety.

Each ring 2220 shown also includes additional features. Namely, an inner surface of a wall of ring 2220B, as shown in FIG. 24B, includes grooves or holes 2226 having a size and shape so that a tool, such as a spring loaded telescoping tool, is adapted to grip ring 2220B via holes 2226. Another feature on ring 2220B, and shown in FIG. 24B, are tantalum markers 2228. As shown, there are three tantalum markers on ring 2220B. Rings are configured to include tantalum markers 2228 so that when the rings are placed into the body, the markers can be used as reference locations to ensure that alignment of the system continues to be maintained. For example, through performance of an x-ray, visualization of tantalum markers can be used to confirm that each ring is in alignment with each of the other rings, or that the rings are in alignment relative to the rods or to the vertebrae, all during the course of the surgery. Tanatalum markers can be placed pre-operatively or intra-operatively.

In a variant, a retracted adjustable rod structure can include any number of stacked rings (e.g., 2, 3, 4, or more). In some variants where stacked rings are included, none or only some of the rings may include engagement features to interconnect the rings. It is further contemplated that the rings can include additional physical features in addition to those described above. For example, the rings can include holes through their thickness sized for the placement of wire, fiber optic cable or cable for neuro-monitoring. Of course, the device used to supply lighting to the tube can be any device capable of lighting the distal end of the adjustable rod structure. One or more rings can also include an interior surface with a black color and having a matte finish. The black matte finish can improve the effect a lighting device has on the intended anatomical location by preventing tissue adjacent to the portal from lighting up among other advantages. For example, an LED may emit light at the insertion end of an adjustable rod structure where a ring at the same end has a black matte finish. Because of the finish on the ring, the visibility of the lit target site is improved as glare from the ring surface is minimized. Additionally or alternatively, at least one ring can be manufactured from illuminating material to provide lighting to the intended anatomical location.

In other variants, one or more rings can be assembled from two or more components or pieces. For example, a ring can include two combinable C-shaped semi-cylindrical components. In another example where two or more rings are included in the system, one or more rings can be monolithic and one or more rings can be assembled from two or more components. In yet another example where two or more rings are included, one ring can be smaller in cross-section than the other. Typically, a smaller ring will fit snugly within an inner diameter of a larger ring so that only a nominal amount of space remains between the rings. In some examples, the smaller and larger ring can be combined with an adhesive prior to surgery to create a combined, preformed ring. When rings are combined, each can have differing thicknesses and heights, provided their combined thickness and height is shaped to slide between, around or over the rods of the adjustable rod structure. For example, a first, smaller ring with uniform depth and thickness fits inside a second, larger L-shaped ring, where the L-shape denotes a dual thickness of the ring and the larger thickness equals the smaller thickness plus the thickness of the smaller ring. In other examples, the smaller ring is constructed of material condusive to lighting such as a clear lucite, lexan or polycarbonate, while the larger ring is a solid color capable of blocking the transmission of light, such as a black matte finish. In this configuration, direction of light into the target site is optimized because the outer ring keeps lighting within the portal, among other reasons. In other examples, one or more rings can be expandable.

Figure 25A:
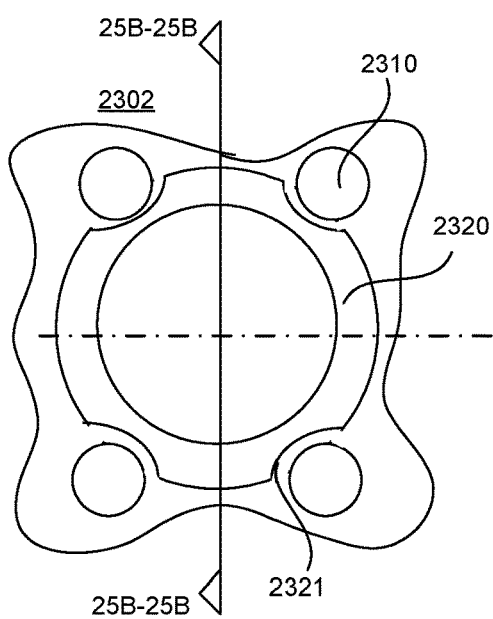
FIGS. 25A and 25B are rear facing and side views of a ring disposed between rods in accordance with another embodiment of the present invention.
Figure 25B:
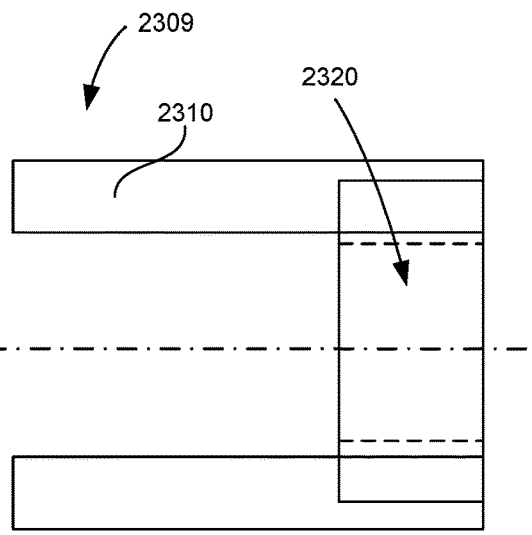
Figure 26:
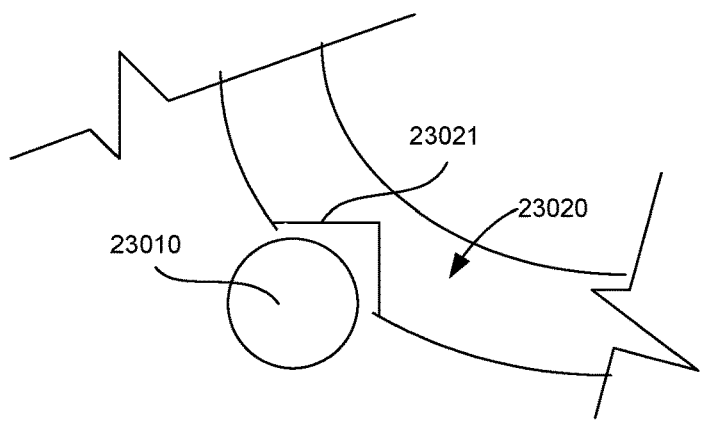
FIG. 26 is a close up partial rear facing view of a ring disposed between rods according to another embodiment of the present invention.

A further embodiment of ring 2320 is depicted in FIGS. 25A and 25B. Ring 2320 includes an inner surface that is entirely circular while an outer surface of ring 2320 includes concave indentations 2321. Concave indentations 2321 form arc shaped surfaces on the outer surface of ring 2321 and include a curvature sized so that rods 2310 of the adjustable rod structure 2309 are nested and mate with indentations 2321 when ring 2320 is positioned in between rods 2310. The indentations on the ring maintain an opening size through the access and concurrently minimize a cross-sectional space required for the retracted rods. In other words, the profile of the adjustable rod structure in the open position is minimized with placement of ring 2320. FIG. 26 depicts a ring 23020 having grooves 23021 with two planar surfaces adjoined at a line extending parallel to a longitudinal axis of the ring and recessed from an outer surface of the ring. In a manner similar to that described for indentations 2321, grooves 23021 are sized so that rods, such as circular rod 23010 shown in FIG. 26, correspond with groove 23021. Other rods may correspond as well, such as rods with an ovular or rectangular profile.

Figure 27A:
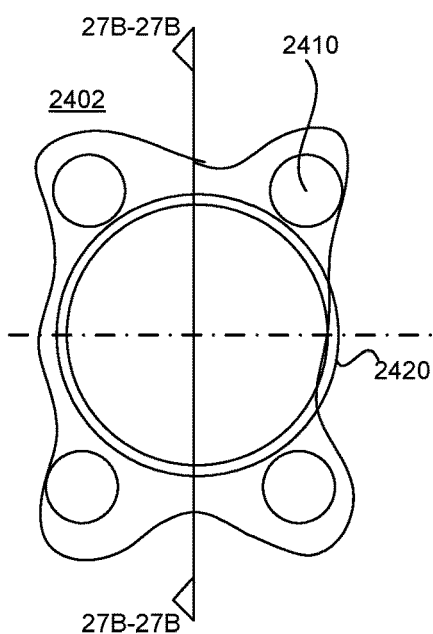
FIGS. 27A and 27B are rear facing and side views of a ring disposed between rods in accordance with another embodiment of the present invention.
Figure 27B:
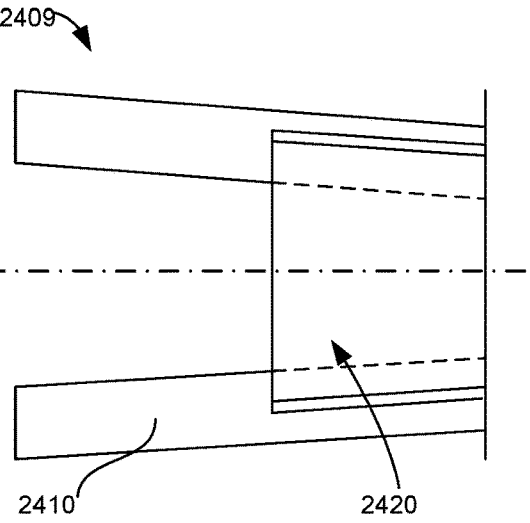

In other embodiments, an outer surface of the ring tapers in a longitudinal direction, such as ring 2420 shown in FIGS. 27A and 27B. This ring structure, when inserted between rods, creates a construct that tapers inward toward a distal end of the construct. Although rods 2410 can initially be in a parallel orientation, the placement of ring 2420 along with the pressure from surrounding tissue can result in the tapered orientation shown in FIG. 27B. In a variant, the ring can have outer surfaces that taper outward towards the distal end of the rods. In other variants, tapering of the outer surface of the ring in either direction may vary from a taper of an inner surface of the ring so that a wall thickness of the ring varies over its length. For example, where outer ring tapers inward toward the distal end of the rods, the inner surface can have no taper. In another example, the outer surface can taper outward while the inner surface tapers outward but at a lesser angle relative to the longitudinal axis of the ring.

Figure 28:
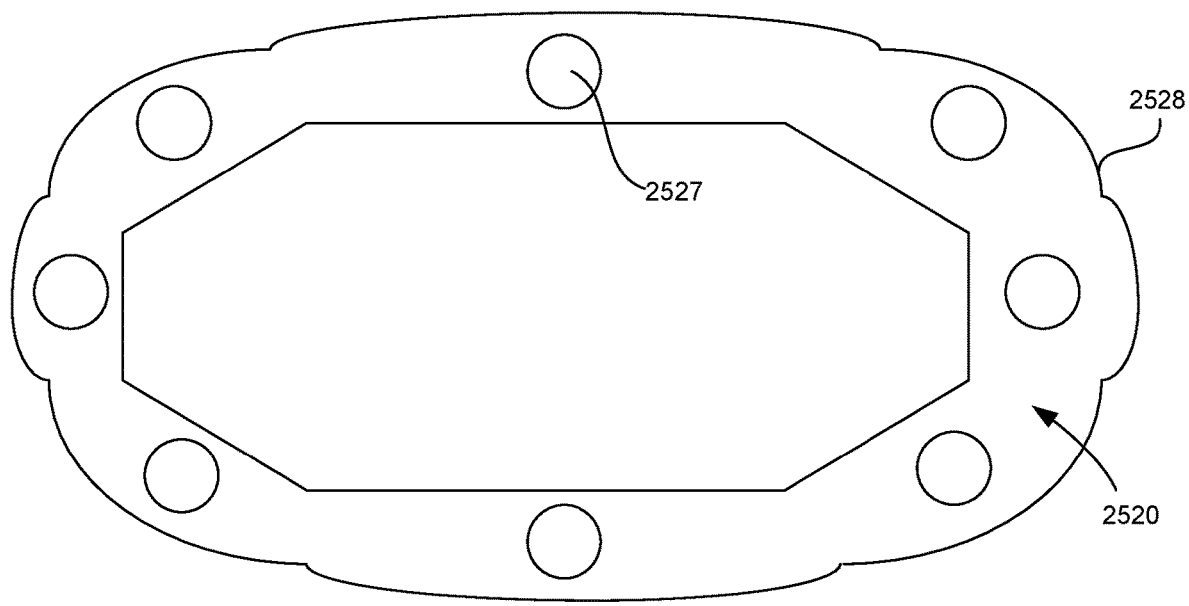
FIG. 28 is a rear facing view of a ring in accordance with another embodiment of the present invention.
Figure 29:
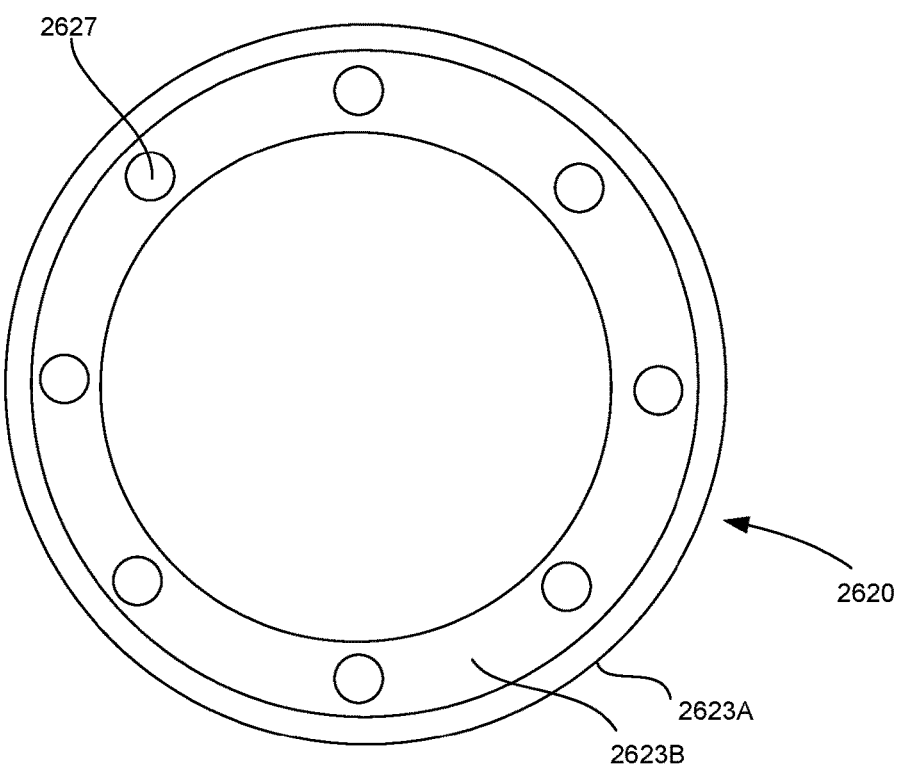
FIG. 29 is a rear facing view of a ring in accordance with another embodiment of the present invention.

In other embodiments, a ring for use with an adjustable rod structure can be placed over retracted rods, examples of which are shown in FIGS. 28 and 29. In the embodiment of FIG. 28, eight holes 2527 are distributed through a perimeter of a ring 2520. An outer surface 2528 of ring 2520 protrudes around each hole in a convex fashion to maintain a minimum thickness of the ring throughout. Ring 2520 is sized and otherwise configured so that it may be placed through rods (not shown) in a retracted position by advancing ring 2520 through the rods via holes 2527. Ring 2520, when disposed over retracted rods, provides a larger opening than what would otherwise be available when a ring is placed within an area inside the rods, such as would be the case with ring 2420 shown in FIG. 27A, for example. This is because only part of the cross-sectional area of ring is interior to the rods. Ring 2520 is further configured so that where retracted rods taper inward in a distal direction, advancement of ring 2520 causes further retraction of the rods. Put another way, ring 2520 reduces or negates any taper extant in the rods. It is further contemplated that with some adjustable rod structures, advancement of ring 2520 causes rods to retract from a closed to a fully retracted position. Another advantage of ring 2520 is that because of its polygonal shaped inner wall and holes for slidable engagement with rods, a surgeon can have more confidence knowing that the ring is properly aligned when it is slid over the rods. In FIG. 29, a circular ring 2620 is shown having two circular layers through its thickness including a metallic outer layer 2623A, and a polyurethane inner layer 2623B. The interface between the two layers is fixed so that neither layer moves with respect to the other. Within the thickness of polyurethane layer 2623B are holes 2627 distributed equidistantly as best shown in FIG. 29. In the illustrated embodiment, there are eight holes 2627 sized for rod placement therethrough. Ring 2620 is configured for placement over rods (not shown) in the same manner as ring 2520. Polyurethane layer 2623B includes an inherent malleability so that in the event that a rod cannot be disposed directly through opening 2627, hole 2627 may stretch to allow disposition of the rod therethrough.

Figure 30:
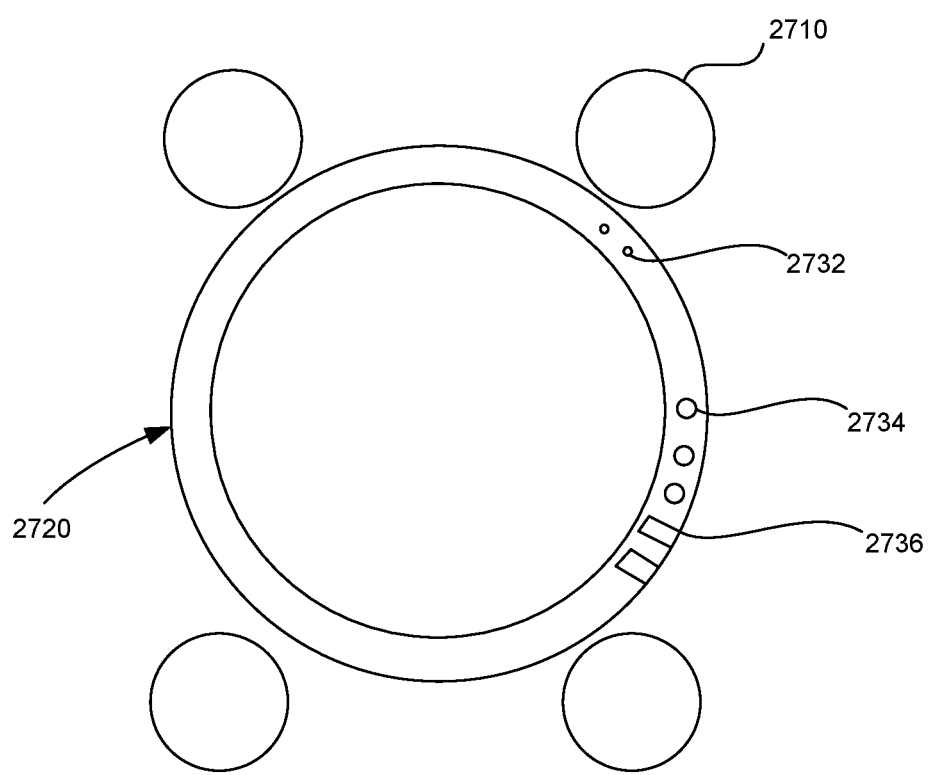
FIG. 30 is a rear facing view of a ring disposed between rods in one embodiment of the invention.

In any one of the above embodiments, the ring can include indicators such as those shown in FIG. 30 on a top surface of a ring 2720 in place between rods 2710. Indicators are used to identify the properties of a ring and can also be used to confirm the alignment of the ring when it is in position between the rods. FIG. 30 illustrates a ring that includes several types of indicators. One indicator is a quantity and/or pattern of dots 2732. In one example of how dots can be used, two dots can mean that ring 2720 is length X whereas three dots can mean that the ring is length Y. Other examples of what the indicators can represent include the diameter of the ring, any contours on its inner or outer surface, the shape of its distal end face (e.g., arcuate, flat), or other physical features such as notches, tantalum marks, and so on. In a similar way to a pattern of dots, colored dots 2734 can also represent different features of the rings, e.g., each color can be associated with a property of the ring. Another indicator shown is a physical marker on the rim. In FIG. 30, notches 2736 are shown on the upper surface of the ring. The shape and/or quantity of notches 2736 can be used to create a system of identifying the characteristics of the ring.

The above embodiments of the ring or rings may be varied in many respects. For example, the rings can have an ovular or polygonal profile to match an inner area of the adjustable rod structure when in the open position. In the same way, a thickness of the ring can be modified or be variable at different points on the ring to suit a particular surgery being performed. For example, where it is anticipated that loads from muscle tissue surrounding the adjustable rod structure will be high, rings with a greater thickness can be used than what would be used otherwise. In another example, if one side of the retracted rod portal in the patient is supported by a larger rod than the others, the ring may be thicker at that location of the perimeter to support the load from the rod. The rings can also include engagement features on an interior wall of the ring configured to engage with corresponding features on the rods so that the ring can be disposed entirely external to all rods of the adjustable rod structure.

Further embodiments of rings are contemplated, including rings having a profile configured to fit within an opening in a retractor when the retractor is holding rods so that the ring can be inserted into a portal into the patient without removing the retractor. Other characteristics of the rings that are contemplated and that may be a variable when assembling a kit include whether the ring is disposable, kitted, whether the ring has keys, what materials are used to manufacture the ring, and the variety of features on the ring surface for connecting to tools, other rings, and any other component used in the procedures described herein. Moreover, rings including holes for receiving rods (like those shown in FIGS. 28 and 29) can include any number of holes for receiving any number of rods. It is also contemplated to provide the rings with more holes than the included rods so as to allow the ring to be positioned in different orientations. For instance, ring 2520 of FIG. 28 includes eight holes 2527, but such could be utilized with a four rod adjustable rod structure.

Retractor

The system further includes a retractor to complement the adjustable rod structure and rings. In its most basic form, the retractor is configured to retract the rods of the adjustable rod structure using adjustable arms engagable with individual rods of the adjustable rod structure. The arms are adapted for movement so that an area interior to the rods progressively becomes larger with actuation of the arms. In one embodiment, the retractor is as shown in FIG. 31. The retractor 50 as shown is configured for engagement with the four rod adjustable rod structures shown in FIGS. 1 to 7, though may be configured for engagement with other adjustable rod structures, such as those described in other embodiments herein. The retractor 50 includes a semicircular frame 51 with a slot 52 over a portion of its length on an inward facing surface and openings 58A distributed along its length on a top surface and sized for the placement of pins therethrough, described in greater detail below. At each end face of frame 51 is an engagement feature. In FIG. 31, it can be seen that one end face has a male engagement member 53 with ratchet teeth and the other end face has a female engagement member 54 that corresponds to ratchet teeth 53. The structure is thus configured so that two frames 51 are engagable with each other, the general principle of which is shown in FIG. 31. When two frames 51 are engaged, the combined shape of the frames in one plane is circular. Ratchet teeth 53 are also configured so that single tooth adjustments can adjust the size of the combined frames 51, moving each frame 51 either closer together or further apart in a linear movement. With arms 56 attached to each frame 51 as shown in FIG. 31, moving frames 51 relative to each other concurrently retracts or brings together rods disposed in arms 56 of the frames. Each arm 56 is linear and includes lock pin holes 59 configured and sized for lock pins 58 and an opening 57 with a diameter corresponding to a rod 10. Openings 57 are configured so that rods of varying lengths can be used for one retraction operation by securing longer rods to the retraction mechanism at a location on the rod remote from its proximal end so the length below the retractor is similar to shorter rods attached to the retractor. Furthermore, openings 57 are further configured so that rods can be rotated about their longitudinal axes, either in tandem with one or more of the other rods, or independently. Lock pin holes 59 are distributed on the length of the rod in two rows and each is configured for receiving a lock pin 58. Lock pin 58 is disposed in one of openings 58A in frame 51 and is further disposed in one of lock pin holes 59. In addition to rotatable engagement with the frame 51 via lock pins 58, each arm is also configured to slide within slot 52. Lock pins 58 are configured so that with some actuation, the arm becomes sufficiently disengaged from the frame so that it can be slid within slot 52. The ease with which the arms rotate and/or slide is a function of how tightly pin 58 is secured to frame 51 and arm 56.

Retractor 50 can be varied in many respects. In one example shown in FIGS. 32A and 32B, one or more of the arms 2856 include an adjustable locking mechanism 2860 configured to engage with notches 2810A of a rod 2810 (FIG. 32B) of the adjustable rod structure (not shown). Each adjustable locking mechanism 2860 includes a spring 2862 so that a surgeon can quickly and easily draw back the locking mechanism 2860 from a rod 2810 disposed in hole 2857 of arm 2856. The spring as shown is a forward biased spring mechanism compressive in the direction of the frame, though the spring used can be varied as a matter of design choice. Thus, adjustable locking mechanism 2860 is configured so that rod 2810 disposed in an arm with the mechanism are releasably secured to the retractor, allowing for securement of the rod at different locations on its length. Locking mechanism 2860 can be used on one or more arms of a retractor and can include one or more variants of the illustrated structure on a particular retractor. Where two or more adjustable locking mechanisms are included on a retractor, each one is configured to be either individually actuated so that adjustments can be made to one rod without affecting the other rods or for simultaneous actuation and adjustment of the rods. One advantage of this variant of the retractor is it reduces the necessity for a wide range of rod sizes to be included a kit as individual rods can effectively cover a range of rod lengths.

Of course, many other embodiments of retractor 50 illustrated in FIG. 31 are contemplated. For instance, the shape of the frame can vary. In one example, the frame can be modified so that when fully assembled, a top and bottom surfaces are both curved (i.e., non-planar) and a slot on a side surface running parallel to the top and bottom surfaces is also curved. Thus, when an arm of the retractor is moved within the slot, it rotates and translates, the rotation occurring due to the curvature of the slot. In other examples, an assembled frame can have a polygonal, oval or other shape. The number of components to close the frame can also vary. For example, four frame components can be assembled to complete a polygonal shape, two frame components can be assembled to complete a square shape, and so on. Similarly, the shape and quantity of arms can also vary. For example, five arms can be attached to the frame. In another example, the arms can include a hole sized for rods that is at an angle relative to an axis orthogonal to the frame, allowing rods to be advanced at an angle with respect to an axis of an access portal inside the patient. Similarly, the arms and/or the holes in the arms can be adjustable to alter the angle of the axis through the hole of the arm. Structure for pins disposed in the frame is a matter of design choice. In some embodiments, an equivalent or other substitute for pins can be disposed in the frame. In these embodiments, openings in the frame can be configured for placement of the applicable connecting member. In one embodiment, the holes on the top surface of the frame can be replaced with a slot extending over a portion of the frame length. In other embodiments, holes can be placed at regular intervals on an inside surface of the frame in place of a slot. The holes can be configured to permit insertion of arms therein. In yet another embodiment, the arms can include a single channel within a width of the arm and extending parallel to its length in place of locking pin holes. An advantage of this variant is that adjustments of the rod position can be extremely precise due to the continuity of adjustment available through the channel in the arm structure (continuous control and movement). In other embodiments, slots, holes, channels and other similar features are interchangeable on the frame and arms and can be used in various locations on the structure as a matter of design choice. In one embodiment, the male engagement member can also be varied to include any surface features that can be shaped so as to correspond and interdigitate with features of the female engagement member. Alternatively, the male-female connection can be substituted with any form of anchoring mechanism to secure two or more frames.

Another embodiment of a retractor 150 is illustrated in FIGS. 33 and 34 and an example of a tool that can be used with retractor 150 is shown in FIG. 35. An exemplary adjustable rod structure for retractor 150 as shown is that depicted in FIGS. 11A-11B. Retractor 150 includes a hexagon-shaped frame 151. The structure forms a ring in that an interior portion of the frame is hollow. FIG. 33 shows five arms 156, 156B each positioned on a top surface of frame 151. Four of five arms 156 are configured for disposing rods used to expand an opening in the body, while fifth arm 156B is configured for independent adjustment and insertion of a fixation post, such as that shown in FIGS. 11A-11B. Of course, retractor could also be utilized with a five rod adjustable rod construct. Each of arms 156 is rigidly fixed to frame 151 using pins or other mechanisms for removable fixation (not shown) and includes a tapering end facing inward toward the center of the frame configured so that in a fully closed position, a distance between arms is minimized. In this way, each arm 156 corresponds to the others when positioned toward a center of the frame. Each arm in FIG. 33 includes two holes 159 configured for placement of a distracter tool 170 (FIG. 35) and described in greater detail below. The inclusion of two holes 159 provides greater flexibility in positioning distracter 170 when retracting opposing arms on the frame. Holes 159 are similarly positioned on each arm so that adjustment of the position of opposite facing arms produces similar movement of each arm but in opposite directions. At the tapering end of each arm 156 is a further hole 157A configured for disposing rods therein. In the retractor shown, when each arm is in the closed position, the tapering ends of each arm converge and nest with one other so that holes 157A disposed in each arm 156 correspond and align with rods of an adjustment rod structure as such rods would be aligned in the closed position. For example, all four rods 910 of adjustable rod structure 909 can be disposed in holes 157A while adjustable rod structure 909 is in the closed position. Arm 156B is shown with a hole 157B configured for placement of a fixation post therein. As evident from FIG. 33, arm 156B is independently moveable relative to arms 156.

As shown in FIG. 34, a release structure 160 is included within frame 151 and positioned below each arm 156, 156B. Corresponding to release structure 160 and also shown in FIG. 34, each arm 156 includes teeth 163 on a portion of its bottom surface. Upon linear movement of arm 156 toward or away from a center of frame 151, teeth 163 slide over release structure 160, locking a new tooth with release structure 160 as arm 156 is advanced. Release structure 160 is configured so that it has at least some resistance when engaged with teeth 163 in the arm so as to prevent accidental adjustment of arm 156, 156B when not desired or intended. Such resistance can be in the form of a spring (not shown). Distractor 170 shown in FIG. 35 includes two arms 171A, 171B configured to mirror each other and connected at a pivot location 172. At a distal end of each arm is an engagement block 174A, 174B configured to be disposed in and secured with holes 159 of arms 156. The distracter is configured so that actuation of arms 171A, 171B causes opposing arms 156 to be retracted or brought together linearly and in unison. As shown, distracter 170 is configured for manual operation by a surgeon, however, automated technologies for actuation of the arms are also contemplated as within the scope of the invention.

Retractor 150 can be varied in many respects. In one example, the shape of the frame is square. In another, it is circular. In other examples, four arms are disposed on the frame. In others, any number of arms can be included. The arm shape can vary as a matter of design choice. The retractor can be configured so that each arm is movable independently or in tandem with one or more of the other arms. In one example with an arm for a fixation post, the arm for the fixation post moves in tandem with the other arms. In other examples, the retractor does not include a separate arm for a fixation post.

Figure 36:
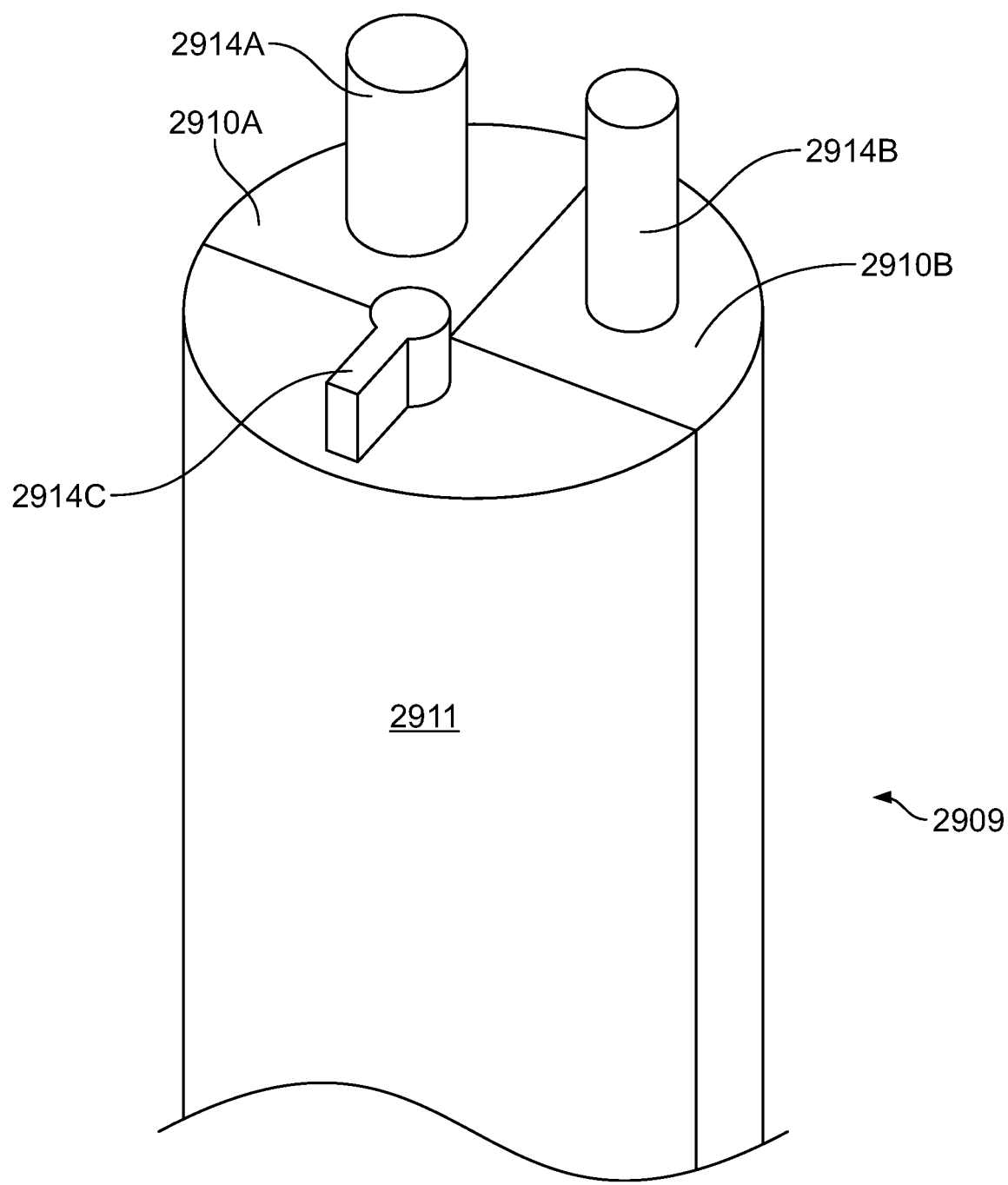
FIG. 36 is a perspective view of an adjustable rod structure according to another embodiment of the present invention.
Figure 37:
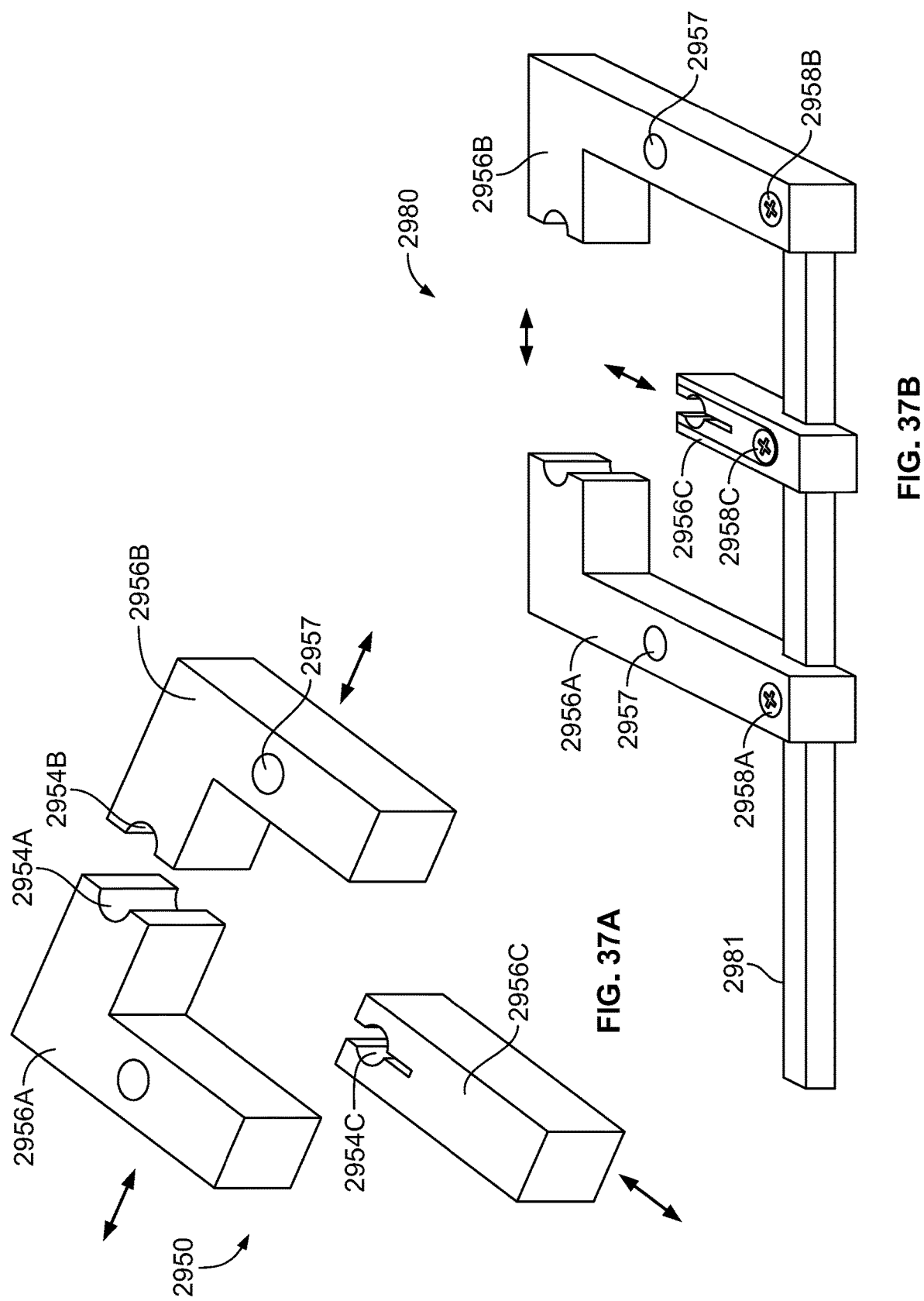
FIG. 37A is a perspective view of arm elements of a retractor according to another embodiment of the present invention.
FIG. 37B is a perspective view of a retractor in one embodiment of the invention with a handle connected to the arms as depicted in FIG. 37A. The retractor also includes a mechanism for actuation of the arms (not shown).

Yet another embodiment of a retractor is shown in FIGS. 37A and 37B. An exemplary adjustable rod structure that is compatible with the retractor 2950 shown in FIGS. 37A, 37B is depicted in FIGS. 8A and 8B combined with features of rods shown in FIG. 36. As shown in FIG. 37A, retractor 2950 includes three arms 2956A, 2956B, 2956C. Each arm includes features configured to correspond to protrusions 2914A-2914C on a proximal end surface of an adjustable rod structure 2909 (FIG. 36). Thus, each of arms 2956A, 2956B includes notches 2954A, 2954B, respectively, that correspond to protrusions 2914A, 2914B on the proximal end face of rods 2910A, 2910B, seen in FIG. 36. Similarly, notch 2954C on arm 2956C corresponds to protrusion 2914C on rod 2911. Protrusions 2914A and 2914B are circular in dimension while protrusion 2914C has a key shape. Of course, the shape of these protrusions can vary depending upon the corresponding structure on arms 2956A-

C. Arms 2956A and 2956B can further include holes 2957 configured for engagement by a tool adapted to rotate the arms and hence rotate the attached rods, as needed. Arms 2956A-2956C as shown provide a similar function to the LITe® Pedicle Based Retractor by Stryker®, which is described in U.S. Pat. Pub. No. 2015/0164569, the disclosure of which is incorporated by reference herein in its entirety. Arms 2956A-2956C are further configured to be combined into a tool 2980 as shown in FIG. 37B. Tool 2980 as shown includes a handle 2981. Handle 2981 extends linearly and defines a rack onto which arms 2956A-C are releasably attached. Fully assembled, tool 2980 includes handle 2981 with arms 2956A-C releasably disposed thereon. As shown, arms 2956A, B are connected so that actuatable structural features 2958A-2958B, such as knobs, of arm 2956A, B, are positioned over the rack of handle 2981. Such features are configured so that translational, radial, arcuate and rotational movement of arms 2956A, B about respective structural features 2958A, B is possible. Also shown in FIG. 37B, arm 2956C is configured to translate laterally relative to a length of handle 2981. Movement is effected through manipulation of an actuatable structural feature 2958C, e.g., a pinion, the rotation of which causes arm 2956C to translate through interconnection between the structural feature 2958C and grooves in arm 2956C. Put another way, actuation is facilitated through a rack and pinion mechanism. Thus, the actuatable structural features 2958A-C facilitate custom retraction to create a portal as desired for a particular surgery.

Tool 2980 with arms 2956A-C can be varied in many ways. For example, arm 2956C can be configured so that it can translate and rotate. In another example, any single arm or combination of arms can be configured to be movable in one, two, or more of the ways described above. In other examples, the pivot point of the tool is positioned at locations on the arms other than those shown in the figures or those already described as a matter of design choice. In yet another example, the arms can be configured to be movable out of a plane passing through arms 2956A-C and handle 2981 of tool 2980 as shown. In still further examples, the retractor can be self-retracting. Yet another example of a retractor is described in U.S. Pat. No. 8,992,558, assigned to Osteomed LLC, and in *Surgical Technique Guide: primaLIF™ LLIF Lateral Lumbar Interbody Fusion System* by Osteomed LLC, the disclosures of which are hereby incorporated by reference herein.

Endoscopic Access System

In some embodiments, an endoscopic access system (not shown) can be used in conjunction with the adjustable rod structure and retractor to perform surgical procedures. Such systems can operate as an effective aid in visualizing a target anatomical site. One example of the endoscopic access system includes a frame securable to a retractor, an access portal with a scope holder that is securable to the frame, a probe secured to the scope holder at a proximal end of the probe and having a lens at a distal end of the probe, the probe being adjustable through actuation of a screw or another similar mechanism in the scope holder. In one example, the probe is a tube. An eye piece is connected to the scope holder and is used to view what is visible from the lens. Actuation of the screw adjusts a depth of the lens within a patient. One variant of the above described system is described in U.S. Pat. App. Pub. No. 2015/0257784, hereby incorporated by reference herein in its entirety. In other examples, the endoscopic access system can further include a microprocessor or other forms of automation that can be configured to manipulate the location and focus of the lens during operation of the system when disposed within a portal of a patient during surgery. In yet another example, the frame of the system can be configured to dock and be secured to a table or another structure other than a retractor. In another embodiment, the endoscopic system can be partially or fully automated through coupling with robotic devices. In other embodiments, visualization within a portal, the portal defined by the retracted rods as described above, can be accomplished with the naked eye.

Robotic Devices

In some embodiments, the adjustable rod structure and retractor are further accompanied by a robotic device, or robot (not shown). The robot can be incorporated into the system and used for many purposes. For example, it is contemplated that the robot can assist a surgeon who otherwise performs surgical steps through physical movements by complementing those movements. In one specific example, and as described below, a robot can assist a surgeon in advancing an adjustable rod structure into a patient in a controlled manner. In this manner, the surgeon retains the ability to physically perform the advancement function, albeit with feedback from the robot. This can be coupled with preoperative planning steps that help dictate the proper positioning of the adjustable rod structure within a three-dimensional space inside the body, i.e., planning to set outer boundaries for tools and other objects inside the body. In another example, a working surface area at the target anatomical location is controlled. For example, a boundary is set to limit movement over a surface of a vertebral body. In yet another example, the robot can be used to track the location of an implant being advanced through a portal in a patient toward a target anatomical site. In this manner, the robot can serve a navigational function. The robot can also include structure allowing for visualization of a target anatomical site through a portal created in a patient. In these and other examples, the robot can also be used to trigger signals to a user regarding the proximity between a tracked object and an identified boundary or location to avoid, such as a nerve or a boundary determined based on that defined during the preoperative planning and setting of the tool and/or implant trajectory. For example, feedback by the robot can vary based on the proximity of the tool to the boundary. In addition to the semi-autonomous usages described above, it is also contemplated that some or all of the functions available through robotic devices can also be fully automated. The degree of assistance to be provided by the robot may depend on and be determined by the experience or comfort level of the surgeon, or on the difficulty of the procedure being performed, among other factors.

In one embodiment, a surgical system includes a computer, a robot in the form of a haptic device and a tracking system (none shown). The computer sends, receives and stores information from the other components and external data sources as deemed appropriate for a particular type of surgery and/or a particular patient. In particular, physical measurements within the body of the patient can be taken with data received by the computer so that detailed information regarding the dimensions of a patient's anatomy can be stored. This establishes a coordinate system in the body so that a position of any tool or other object in the body can be identified relative to structures inside the body during surgery. Tool or object location is possible through a connection between the tool and the computer through the haptic device connected to the tool. Once the computer has information on the patient's anatomy, preoperative planning can be used to establish a haptic boundary, i.e., a three-dimensional space, for the planned surgery. The haptic boundary is defined using coordinates to delineate a boundary limiting an operable area, where the coordinates are based on the established coordinate system and calculated based at least in part on the surgery being performed and the tools being used. For example, input of a trajectory into the body for adjustable rod structure will allow the computer to calculate an appropriate haptic boundary.

With preoperative planning complete, including determinations of tool trajectory for surgery, the haptic device is prepared for use. The haptic device is configured to, among other functions, move tools such as adjustable rod structure through physical manipulation of the device by the user. For example, the user pushes a handle of the haptic device connected to the adjustable rod structure. The haptic device can be programmed in many ways to adjust how a tool is controlled and whether a user receives feedback during use. The response the user receives from the haptic device during advancement of a tool is also referred to as haptic guidance. In one example, the user can be made aware of such limits through force feedback by the haptic device, such as a vibration. In some variants, such vibration can increase in intensity as the user moves closer to the haptic boundary. In other variants, the haptic device can fully prevent further manipulation of a tool by the user if the haptic boundary is reached. The robot can be configured so that the user holds a component of the robot or the tool itself for manipulation of the tool. In another example, the haptic device, coupled with neuromonitoring technology, can be programmed to limit movement of a tool, e.g., the rod structure, if it has been advanced to a location too close to a nerve based on a predetermined safe distance programmed into the system. In another embodiment, the user can use a joystick to move a tool, e.g., adjustable rod structure. With the use of a joystick, the user's movements are not physically connected to the tool and a position of the tool may be viewed via a monitor. As in the other embodiments, the system can be configured so that haptic guidance, i.e., force feedback, occurs in the joystick. In yet another embodiment, in addition or alternatively to a haptic device, audio announcements can be used to warn the user when movement outside of defined boundaries is imminent. Similarly, other forms of guidance known in the art other than haptic guidance are also contemplated to assist a surgeon.

The tracking system includes a tracker that is affixed to an object to be tracked, the object being, for example, a tool such as adjustable rod structure or an implant. Information about the tracker is sent to the computer to provide position information for the robot. The tracker can further include LEDs which, by their pattern, indicate a position of the tool being tracked. The LEDs may be placed on the tool or remotely on a rim of the retractor or other structure. Remotely placed LEDs can communicate with the tool through a wired or wireless connection. The LEDs can function to alert a surgeon of the proximity of a tool, implant or other object either to the retractor, to boundaries within the surgical site set through preoperative planning, or to other locations of concern, such as nerves. One example of a robotic device that can achieve the above functions is described in U.S. Pat. No. 8,010,180, hereby incorporated by reference herein in its entirety. Other examples of robotic devices, their components, and systems and methods of use respecting same, are described in U.S. Pat. Nos. 7,683,565, 7,747,311, 8,095,200, 8,571,628, 8,287,522 and U.S. Pat. App. Pub. Nos. 2015/0119987, 2015/0080717, and 2017/0000562, hereby incorporated by reference herein in their entirety.

Method of Use

Another aspect of the present invention relates to a method of using the apparatuses, systems and kits as described herein. Several approaches are presently known for accessing the spine for purposes of excising a portion of or an entire intervertebral disc and thereafter implanting a spinal implant or the like. Of these, the apparatuses, systems and kits described herein are ideally suited for a lateral trans-psoas approach. Other approaches that can be adopted include oblique, such as an oblique lateral interbody fusion; anterior; and posterior. Examples of some of these approaches are found in, for example, U.S. Pat. Pub. No. 2016/0081681 and U.S. Pat. Pub. No. 2012/0035730, the disclosures of which are hereby incorporated by reference herein. One advantage of the lateral approach is that a surgeon has the ability to place a larger implant into the body than would otherwise be possible or even place two implants.

In a first embodiment, the method is described in the context of a lateral trans-psoas approach to the spine. Initially and prior to placing any tools through an incision in the skin, the adjustable rod structure 1 is brought into a closed position. Once in a closed position, the adjustable rod structure is ready for advancement. The adjustable rod structure can be advanced on its own in a manual fashion or alternatively, additional elements can be used, for example, a holding element 96. When a holding element 96 is used it is secured to the rods or rods and probe by sliding holding element 96 over the rods and probe using handle 98. Securement of holding element 96 to rods and probe is achieved with a bayonet structure built onto the surface of the rods and a surface within the holes of the holding element, although other lock and release mechanisms are also contemplated. The holding element, as described above, keeps rods and probe fixed relative to one another when in the locked position. With holding element 96 in place, a clamping device 94 is then engaged with a proximal end of adjustable rod structure 9 for additional support, and, in conjunction with handle 98, used to advance adjustable rod structure 9 to a target site (FIG. 1). In another example of this step, advancement is accomplished with holding element 96 alone, and thus without clamp 94 or handle 98. Alternatively, holding element 96 with handle 98 alone can be used. In still further examples, a mechanism other than holding element 96 can also be used to hold the rods and advance rod structure 9. When measurements and other preparation including x-rays and/or fluoroscopy are completed to confirm an entry point for placement of adjustable rod structure 9 into the body and a trajectory for the portal/opening into the body, a percutaneous incision is created in the skin. Adjustable rod structure 9, in the closed position, is then inserted through the incision as shown in FIG. 38. Because probe 16 includes a tapered insertion end 17 and exhibits a small enough overall profile in a closed position, advancement of the adjustable rod structure proceeds smoothly through various internal obstacles. For example, in advancing toward the psoas muscle 2 (FIG. 38), insertion end 17 of probe 16 splits muscle fibers apart as it advances. Splitting of muscle fibers is more likely and occurs with greater consistency with a smaller angle between the conical surface of insertion end 17 of probe 16 and the longitudinal axis of probe 16, particularly when the angle is less than 45 degrees. Because the adjustable rod structure remains in the closed position with a diameter of its outer profile in the range of 7-10 mm, the impact of rod structure 9 on muscle tissue 2 is minimal. In addition, insertion end 17 of probe 16 is subject to compression forces during advancement through muscle tissue 2, and such compression operates to resist any possibility that probe 16 would drop ahead of or otherwise fall out of adjustable rod structure 9. Put another way, the compression force on probe 16 acts to keep it in place between rods 10 during advancement.

Figure 39:
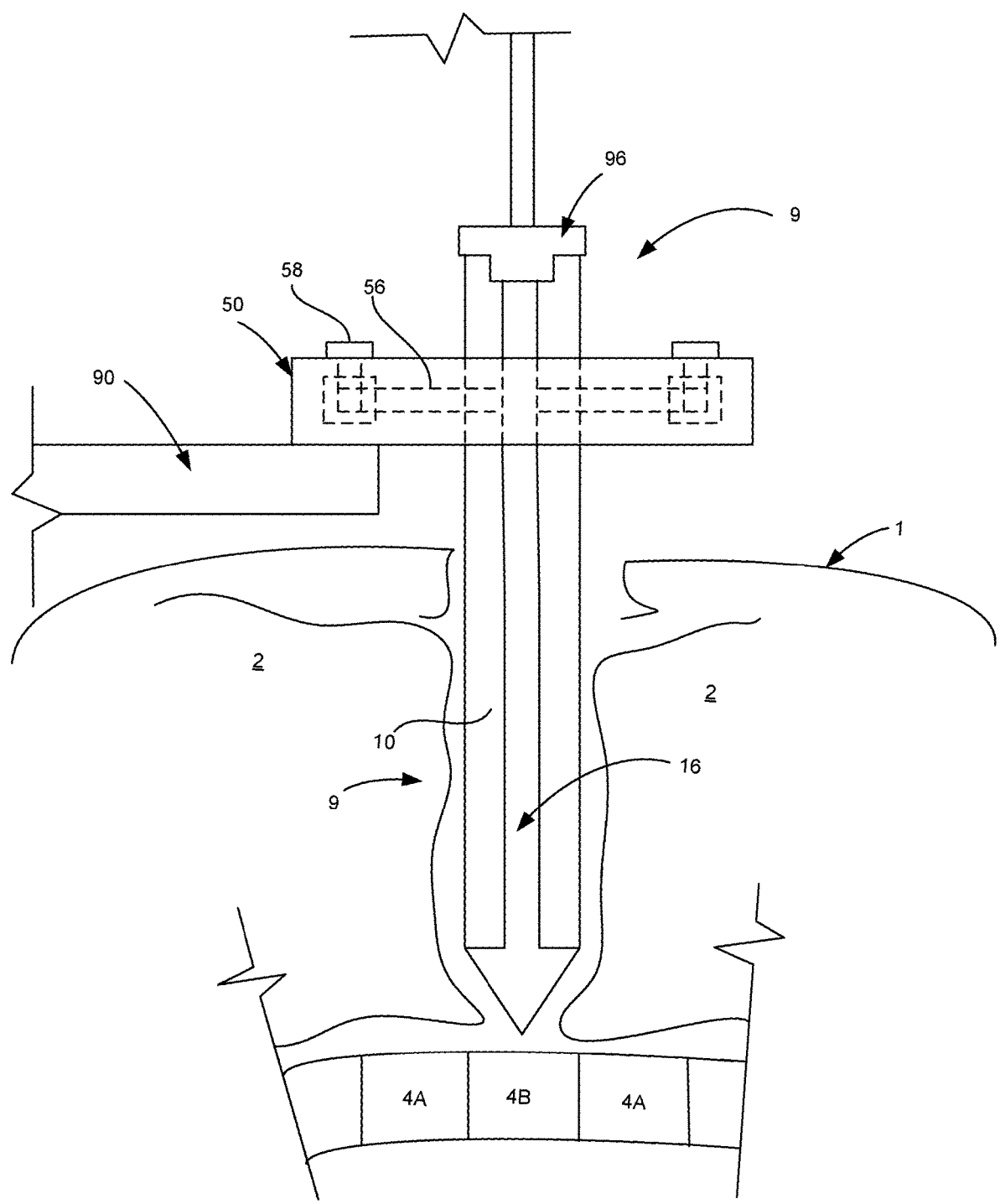

As best shown in FIG. 38, probe 16 is cannulated and an electrode 13 (e.g., wiring) is disposed in the cannulation with a sensor for neuro-monitoring 13A on insertion end 17 of probe 16. With advancement of adjustable rod structure 9 through muscle 2, neuro-monitor sensor 13A on the head of probe 16 moves relative to a longitudinal axis of the probe and at regular intervals determines a distance to any nerves from sensor 13A, in accordance with well-established neuro-monitoring procedures. Because sensor 13A is offset from a centerline of probe 16, proximity to nerves is measured in all directions around probe 16. Neuro-monitoring allows the surgeon to avoid making contact with any nerves by adjusting the trajectory of advancement if necessary to avoid same. Adjustable rod structure 9 is advanced until the probe is positioned proximal to the intended anatomical location, in this case, intervertebral body 4B, as shown in FIG. 39. Although the embodiment shown in FIG. 38 depicts an electrode 13 for neuro-monitoring in probe 16, similar electrodes and sensors could additionally or alternatively be placed in rods 10. Neuromonitoring techniques used in conjunction with this method can include those described above, such as EMG, MMG and ultrasound. Examples of such techniques are also incorporated by reference above. The electrode and sensor on the probe can be modified and/or substituted as necessary to accommodate the type of neuromonitoring technique being implemented. Risks due to contact between the tip of probe 16 and intervertebral space, i.e., intervertebral body 4B, or another target anatomical site following advancement of adjustable rod structure 9 are muted as a result of the dullness of the tip. In particular, if the tip of probe 16 contacts an intervertebral surface, no penetration or injury will occur as the tip is too dull to cause such a result in the embodiments contemplated herein. This improves safety in the performance of the method as the risk of injury is reduced and it also improves efficiency as surgeons can advance the adjustable structure with less hesitation with the knowledge that impact onto bone or other tissue will most likely not cause injury.

Upon confirmation that the probe has reached the intended anatomical location, retractor 50 is introduced to retract rods 10 of the adjustable rod structure 9. To prepare retractor 50 for engagement with structure 9, frame halves 51 are first engaged as shown in FIG. 31. A table 90 is then positioned, if not already, proximal to the incision location and retractor 50 is secured to such table 90, as shown in FIG. 39. Of course, the stabilizing structure is not limited to a table. The stabilizing structure for retractor 50 can be any deemed preferable by the surgeon, such as a robot configured to secure adjacent rod structures and further configured to retract rods. Such robots can further be configured for image guided motion and can incorporate CT scan technology, for example.

Figure 40:
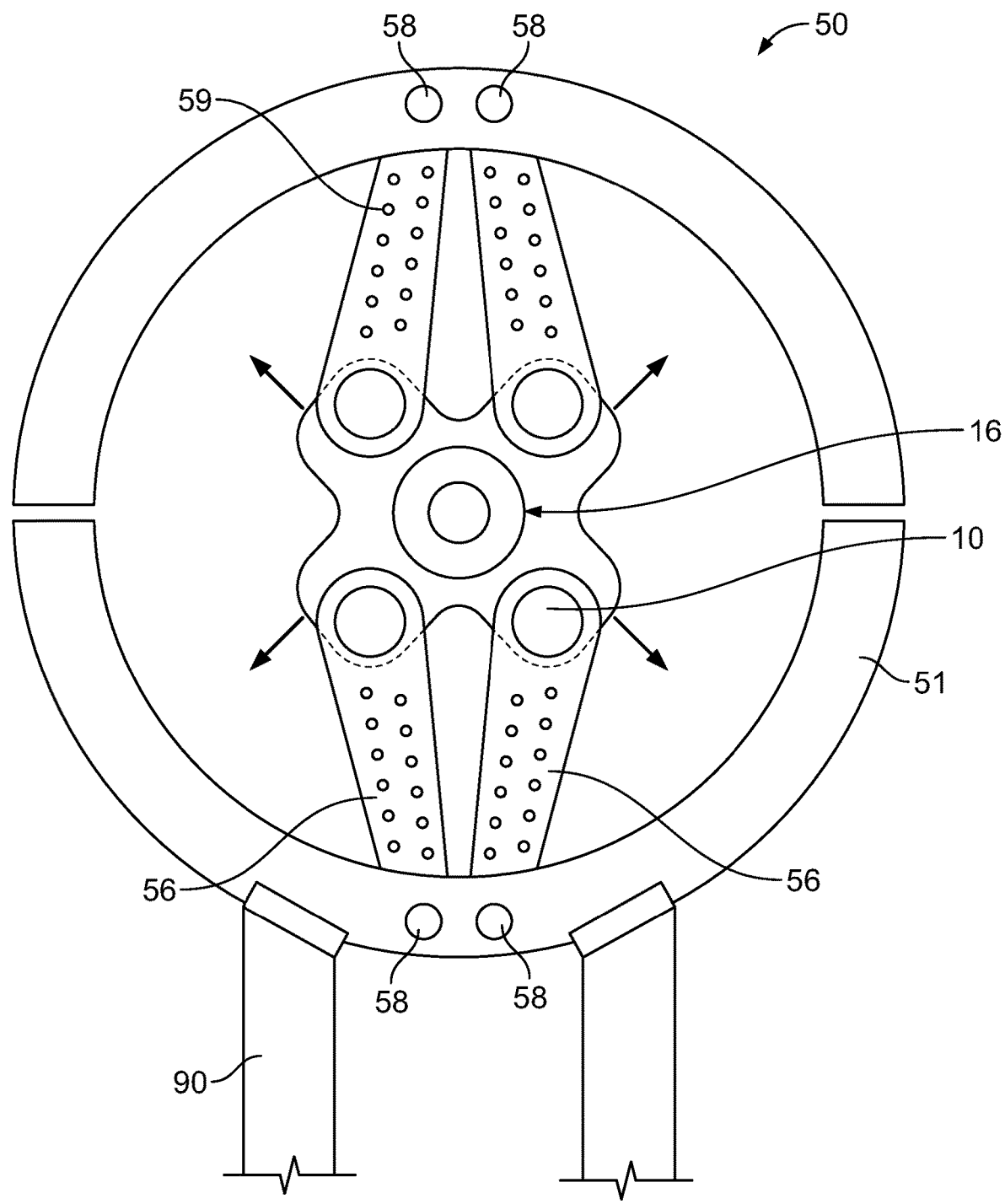
Figure 41:
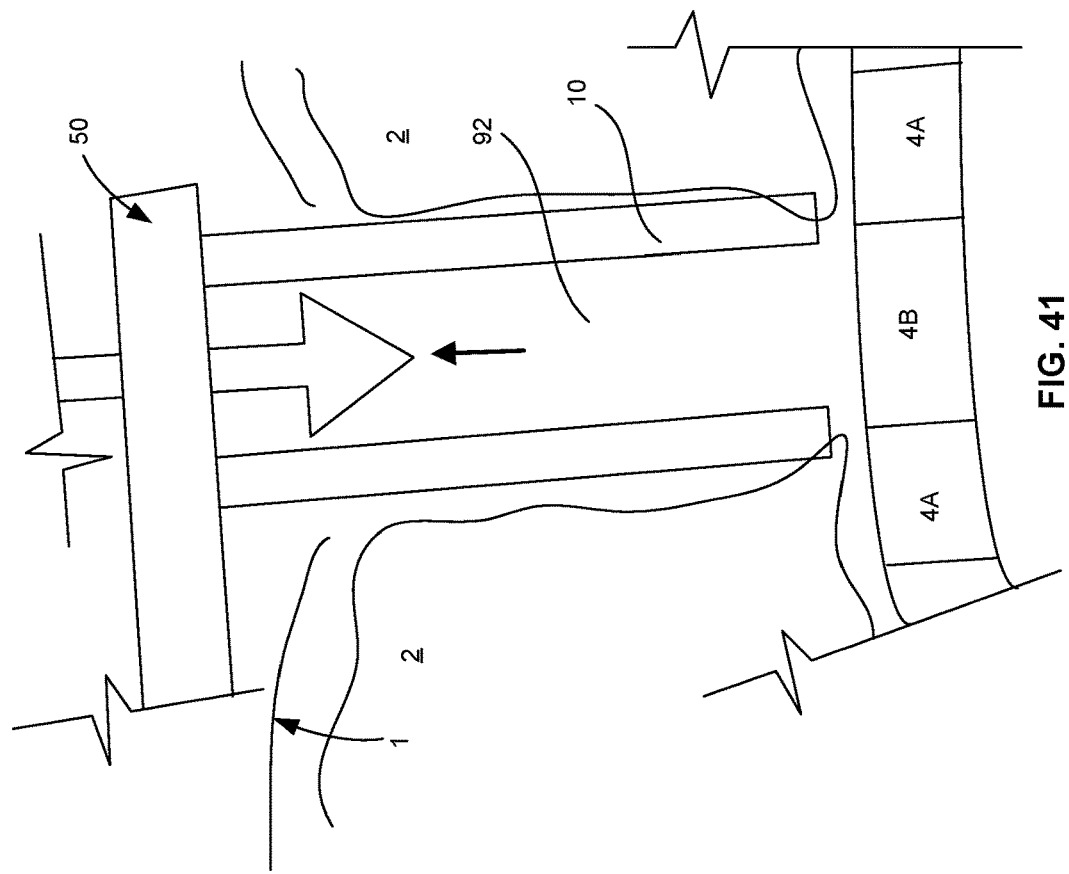

With adjustable rod structure 9 and retractor 50 in position, arms of retractor 50 are engaged to rods at a proximal end of adjustable rod structure 9. During these steps of the method, where applicable, holding element 96 remains secured to the rods and probe to ensure the combined structure remains stable, particularly prior to engaging adjustable rod structure 9 with retractor 50. However, once retractor 50 is secured, holding element 96 is removed from adjustable rod structure. In variants where a clamp 94 is used, it is also removed by the time of this step. To perform the retraction, each of the four arms 56 of the retractor 50 is actuated so that all four move apart from one another, as best shown in FIG. 40. Actuation of the arms can be manual or automated (e.g. with a robot). If it is determined that a desired adjustment of a rod cannot be sufficient based on a range of movement of arm 56 as it is secured to frame 51, arm 56 is adjusted via pin 58 prior to retraction so that the range of possible movement for the rod is sufficient to achieve the desired retraction. For example, pin 58 for arm 56 can be removed and the arm reconnected to the frame on another hole 59 on the arm. Rods 10 are retracted with arms 56 until the retraction is sufficient to create a desired access portal 92, and in any event, at least large enough to create a space sufficient to remove the tapered insertion end 17 of probe 16 from between the rods. Retraction is performed by retracting arms 56 together in tandem, though it is contemplated that one or more arms can be retracted independently with respect to one or more of the other arms. In FIG. 40 and FIG. 2D, rods 10 are shown as retracted sufficiently for removal of probe 16. Probe 16 is then removed as shown in FIG. 41 while rods 10 are held in position by retractor 50.

Figure 42:
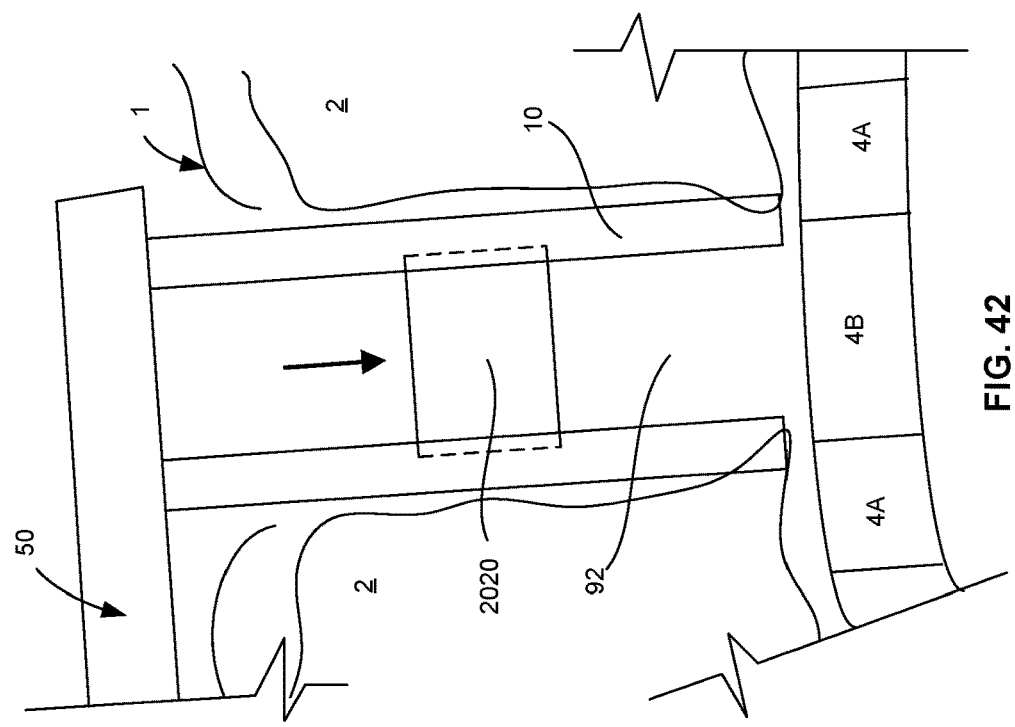
Figure 43:
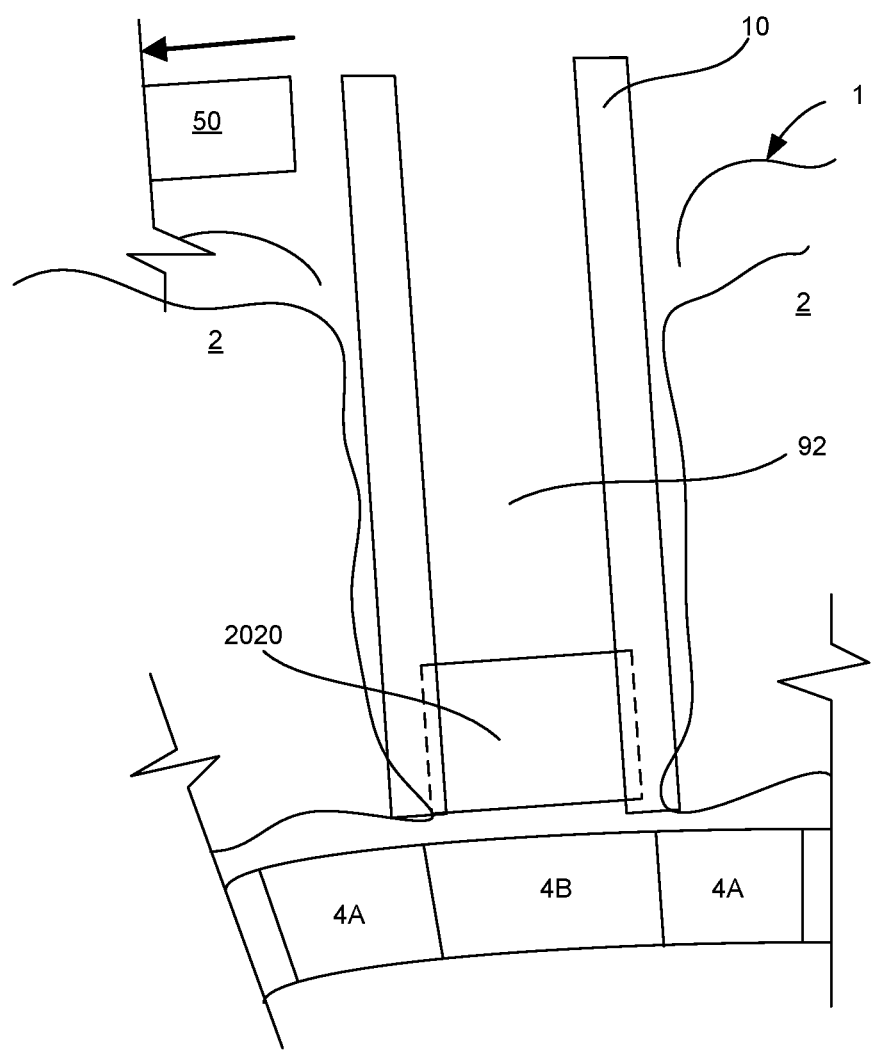

With rods retracted as desired, a ring 2020 as shown in FIG. 22 is then inserted into portal 92 from above retractor 50 and in between rods 10. The ring is advanced as shown in FIG. 42 until it is positioned at a distal end of rods 10. With the ring in place, the rods are held in position and muscle 2 or other tissue is prevented from creeping into portal 92 from outside rods 10. Retractor 50 is then removed as shown in FIG. 43 and the ring continues to hold the rods in place. Removal of the retractor leaves room for surgical access to the intervertebral disc 4B via portal 92. The procedure continues by preparing the intended anatomical location, in the embodiment shown, an intervertebral disc space 4B, for implant placement. An implant is then implanted into the body of the patient through portal 92. The implant can be any kind of implant including those described in U.S. Pat. App. No. 62/319,513, the disclosure of which is hereby incorporated by reference herein; expandable, such as AccuLIF® Expandable Interbody Fusion Technology by Stryker®; Aero® Interbody Fusion Device by Stryker®; Tritanium® PL Posterior Lumbar Cage by Stryker®; peek; bone; or other types of implants. When implantation is complete, the rods are closed, with or without assistance of a mechanical device such as retractor 50, and subsequently removed from the patient manually or using clamp 94 or another device capable of gripping the rods.

As described above, the types of surgeries for which implants, including those listed above, can be performed can vary. For example, the Aero® Interbody Fusion Device by Stryker® can be used in at least anterior and lateral approaches to lumbar surgery while the Tritanium® PL Posterior Lumbar Cage implant can be used in posterior lumbar surgery.

The method of creating a portal to access a portion of the vertebrae can be varied in many ways. In one example, the adjustable rod structure is initially inserted in an already partially dilated position. In another example, holding element 96 is configured so that rods can be retracted while holding element 96 continues to contain the probe, and the holding element 96 remains in place for a period of time after retraction. This keeps the probe from falling to a side of the portal after the rods are retracted. In yet another example, the probe includes a groove as shown in FIGS. 4A and 4B. When using adjustable rod structure 209 to advance to an intended anatomical location, the surgeon places a finger or instrument into the groove to aid in guiding the probe. Rod structure 209 is also sized so that a fixation post can be included in the space of the groove and therefore included as an additional form of securement to a disc space during the procedure. In other examples, the adjustable rod structure does not include a probe. In FIGS. 5A and 5B, a four rod adjustable rod structure is shown that is configured for use as a tool for creation of a portal to access the vertebrae. Adjustable rod structure 309 includes a conical tip based on a tapering end of each of four rods 310 when in the closed position, and the tip is configured to penetrate through muscle in the same way a probe would be. Upon retraction, nothing needs to be removed prior to placement of a ring or other element to stabilize the rods in the retracted position. The method is otherwise the same as described above.

In a further example of an adjustable rod structure without a probe, shown in FIGS. 8A-8D, rods 610 include holes 613 through at least part of the length of the rod so that a distal end of the holes faces an interior of rod structure 609. Thus, when rods 610, 611 are retracted, light is channeled through the rods so that at least an area near the intended anatomical location is lit up. Lighting of the portal can be further varied with rings as described below. In another example, rods of the adjustable rod structure can be of varying length and can be employed by securing each rod to the retractor at different points on respective rods based on rod length. In this way, a corresponding rod length among all rods between the retractor and intended anatomical location is achieved. In other examples the method can be performed with an adjustable rod structure having no cannulations and using blunt finger dilation or other techniques in place of neuro-monitoring. In still others, a wire or cable can be placed external to a rod or probe and connected to a location on the bullet shaped tip with a neuro-monitoring sensor. It is contemplated that any combination and quantity of holes can be used for disposition of k-wire or y-wire, wiring or cable for neuro-monitoring, lighting or other sensors. One exemplary combination is illustrated in FIGS. 20A-20B. Also, lighting can be configured to light up the entire portal. Any addition contemplated as being positionable through a hole in a rod can also be placed external to the rod.

In another example, the method is performed with an adjustable rod structure that includes a fixation post, such as those shown in FIGS. 10A, 10B, 11A and 11B. With structure 909 shown in FIGS. 11A and 11B, rods 910 and probe 916 are advanced independently of fixation post 911. Thus, one approach to the method with structure 909 involves first advancing fixation post 911 to the intended anatomical location, here, an intervertebral disc space, and then engaging the disc. As noted above, either monolithic or non-monolithic fixation posts can be secured to a target site. Where the fixation post is not monolithic, the tip may be rotated relative to the body of the post to secure the post. Then, adjustable rod structure 909 is advanced through the psoas muscle and retracted as done with other methods described herein. Because fixation post 911 is independently adjustable relative to rods 910 and probe 916, fixation post 911 can be removed at any step of the method. Alternatively, the fixation post can be entirely separate from adjustable rod structure 909 and can further be placed without first being secured to a retractor. In yet another example of the method, one or more rods can be replaced once a ring is in place within the rod. This can be done to replace a rod with a fixation post, for example, such as replacing a rod as shown in FIG. 2A with a rod as depicted in FIG. 6B, to provide additional securement of the adjustable rod structure to the vertebrae while performing a procedure through the portal.

In other examples, rings configured for an alternative insertion method can be used, such as the method of inserting rings as shown in FIGS. 21A-21D. Ring 1921 insertion begins when rods 1910 are retracted to the extent necessary to form a desired portal. In the embodiment shown, each of four rods includes a ring 1920, with an engagement portion 1921. When the rings are initially placed over the rods, engagement portion 1921 for each ring is turned inward toward portal 1992. This minimizes the intrusion of the rings into the retracted muscle tissue. The rings are then advanced over rods 1910 as shown in FIG. 21B. When the rings are fully advanced to the distal ends of rods 1910, as shown in FIG. 21D, rings 1920 are rotated so that engagement portions 1921 face away from portal 1992. Each ring 1920 can include engagement features that correspond to engagement features on the rods. This improves rotational control and movement of the ring on the rod. To the extent that the rod has an engagement feature for this purpose, it can extend over part of or the entire length of the rod. The contours of engagement portions 1921 aid in preventing tissue from penetrating into the portal and thus provide added stability. In a variant, rings 1920 can be stackable and two or more rings can be stacked onto each rod 1910. When the rings of FIGS. 21A-21D are used to hold back tissue from creep into a surgical portal, the retractor remains secured to the rods over the duration of the procedure to maintain the position of the rods.

Similarly with a single ring for all rods, where a height of ring 2020 only covers a portion of a length of the rods, additional rings 2020 can be stacked onto the first ring. An example of the resulting series of rings disposed between the rods is shown in FIG. 24A. In other variants, rings can include various features to aid in successfully completing spinal access preparation. For example, as shown in FIG. 24B, physical engagement features 2224 can be built into each ring so that when second, third or more rings (of generally the same cross-section as the first ring) are stacked on rings already in position between the rods, the next ring in the sequence can lock into place. In variants of this example, the series of rings that are stacked may have varying lengths or wall thicknesses provided that the cross-section of each ring is approximately the same. In the example as shown, after one ring 2220 is advanced into position at the distal ends of rods 2210, a second rod is placed over the first and recesses of the ring are aligned with projections extending from a top surface of the lower, positioned ring. As shown in FIG. 24B, engagement features 2224 are configured so that each ring can lock into an adjacent ring. In another example, each ring includes tantalum markers 2228, as shown. In other examples, an additional step of combining ring components each constituting part of a complete ring cross-section takes place to form a complete ring. Once a surgeon has placed one or more rings to prepare a portal for access to the spine, an x-ray (i.e., radiography) can be used to view the ring to verify alignment and proper positioning of the opening through the body. In another example, tantalum markers 2228 can also be configured to be a unique identifier to distinguish different ring properties such as ring length or wall thickness. In this way, if two or three different ring types are to be inserted into the retracted opening, the surgeon can verify whether the inserted rings are in the proper sequence.

Features of the rings can also include holes 2226 sized for engagement by a tool. When a procedure involving the intervertebral disc is completed, features of the ring can be used to remove it from its position in the body. In particular, the retractor is once again engaged with the rods. Then, the surgeon inserts a tool into the portal, such as a spring-loaded telescoping tool, the tool having features that correspond to holes 2226 on the ring, and the tool is used to engage holes 2226. Using this technique, one or more of the rings can be removed simultaneously from the patient. The location of the engagement features on the ring is a matter of design choice and the features can also be indentations, notches, recesses or other contoured surfaces that are easy to clean. In some examples, the rings may be strategically placed so that those with a black matte finish or constructed from clear lucite are positioned to promote effective lighting of a target anatomical site through the portal. As with other embodiments described above, removal of the rings is followed by closure and removal of the rods of the adjustable rod structure.

In another example, the step of placing rings into the retracted adjustable rod structure includes reviewing markers on an end surface of the ring such as those shown in FIG. 30 to confirm that the proper ring is being placed and that the ring is properly oriented for placement. Markers such as shape patterns 2732, colors 2734, and physical notches 2736, among others, can all provide the necessary information to a surgeon to aid in proper placement of the rings.

In other embodiments, the method involves placement of at least two rings between the rods where the second ring is larger or smaller than the first ring. Where the second ring is larger, both rings are advanced into the portal simultaneously. Where the second ring is smaller, the rings can be advanced simultaneously or the second ring can be advanced after the first ring is advanced into position in the portal. In one example, the smaller and larger ring are adhered together prior to insertion into the portal creating a combined dual layer ring. It is contemplated that this approach can be performed in a similar manner where three, four or even more rings are used. It is further comtemplated that this multiple ring approach can be applied to any number of rings having varying shapes and sizes provided that the sequence of insertion involves placement of rings having the same size one after the other or by inserting larger rings first followed by those that are smaller.

In other embodiments, the rings disposed into the retracted adjustable rod structure can also be placed entirely around an outer surface of the retracted rods. For example, ring 2520 shown in FIG. 28 is placed over retracted rods (not shown) immediately following removal of the retractor. The rods are placed through openings 2527 in the ring and advanced to a distal end of the rods, thus holding the rods in place. As with other embodiments, the ring as shown in FIG. 28 can be stackable. In another example, the ring can be as shown in FIG. 29. A method of inserting ring 2620 is similar to that described for ring 2520 above, however, ring 2620 has the additional advantage of having holes 2627 in a urethane layer 2623B of the ring, providing additional tolerance for adjustment in the event that the rods have closed to a position inside that of holes 2627 after removal of the retractor but prior to placement of the ring 2620 over the rods. This is advantageous because it can provide a surgeon with at least several extra seconds for successfully placing the ring after removing the retractor from the rods. Other advantages of the rings as shown in FIGS. 28 and 29 include that advancement of ring 2520, 2620 onto rods tapering inward toward each other can cause the rods to retract through the advancement of the ring. In other variants, dimensions of the ring are such that advancement of a ring over rods retracts rods from a fully closed position to a fully retracted position.

In other variants of the method, various adjustments can be made to the rods with the retractor to ensure that the retraction performed yields an intended result. For example, after initial securement of rods 2810 to retractor 50, rod depth can be adjusted with adjustable locking mechanism 2860 to account for variations in a distance to the intended anatomical location between different rods, as shown in FIG. 32A. Rod depth can also be adjusted in the event that the rods are too long, for example, among other reasons. As part of the method, arms 56 of retractor 50 can be adjusted either laterally via slot 52 or longitudinally via pin 58 to account for the multitude of sizes and geometries of the adjustable rod structure profile. For example, a rod structure including four circular rods will likely require different arm placement than a rod structure with eight rods having an ovular shape. In addition, male-female connection 53, 54 can be adjusted to alter the position of the rods. For example, teeth 53 can be partially removed from opening 54 so that a distance between opposing frames 51 is further apart, altering the relative position of arms 56. In another way, certain variants of the retractor can have an arcuate bottom surface so that movement of the arms along slot 52 causes the attached rods to rotate to an angle relative to an axis parallel to the intended portal. Advancing the rods at such angles can create a tapered portal (opening) in the body of the patient.

In other embodiments, another retractor can be used. For example, the retractor 150 shown in FIG. 33. Following initial preparation of the percutaneous incision location and determination of the trajectory of the cut through the tissue, rods of the adjustable rod structure (not shown) are placed through holes 157A of retractor 150. The adjustable rod structure is advanced in the closed position to the target anatomical location using techniques as described above. When advancement is complete, one or more of the rods is retracted to create a portal to the intended anatomical location. The arms are configured so that retraction can be based on adjustment of one arm 156, two arms, or any other number of arms, such as all four arms 156 for rods. For the retraction of two opposing rods concurrently, a distracter 170 can be used as shown in FIG. 35, which engages with holes 159 in opposing arms and is actuated to cause arms to be moved apart, hence retracting corresponding rods connected to the arms. Each arm includes a release structure 160 to control movement of the arms as adjustments are made. Other tools and manual adjustment of the arms are also contemplated in conjunction with the use of retractor 150. In addition, retractor 150 shown in FIG. 33 includes a separate arm 156B for securement and advancement of a fixation post through hole 157B. Arm 156B is configured so that a fixation post can be advanced independent of other rods, but in some variants, all rods and the fixation post can be advanced into the body in unison.

In another exemplary retractor 2950, shown in FIGS. 37A and 37B, arms 2956A-C of tool 2980 are engaged with respective protrusions 2914A-C on adjustable rod structure 2909 following advancement of the adjustable rod structure through a percutaneous incision of the patient to a target site. After confirming the accuracy of rod position, the arms 2956A-C of tool 2980 are actuated to retract rods 2910A, 2910B, 2911. The arms can be retracted individually or collectively. In one variant, retraction can be lateral for rods disposed in arms 2956A, 2956B while orthogonal to the lateral direction for the rod disposed in arm 2956C, as shown in FIG. 37A. In other variants, the tool can be adapted so that the arms can pivot from different locations on the tool, thus tailoring the function of the tool as may be needed under different circumstances. With tool 2980, each arm can be configured for translational, radial, arcuate and rotational movement. In one embodiment, retractor arm 2956C is configured so that it only translatable. In further embodiments, other retractors can be used. For example, a retractor can have engagement features on one arm that correspond to engagement features of two or more rods. In this way, one arm of a retractor member can engage with at least two rods while a second arm can engage with another pair of rods. Thus, actuation of one arm retracts two arms secured thereto. This approach can be further configured so that each arm of the retractor can secure any number of rods. Four or more arms can also be included with the retractor.

In yet another variant, the method can be performed by attaching the retractor to the adjustable rod structure prior to completing advancement of the rod structure to the target site. In still further variants, the retractor is configured so that it can be used to secure the rods for advancement through a percutaneous incision and into the body, as well as retract the rods upon reaching a target site. Also, in some of the embodiments described above, placement of a k-wire can follow creation of a percutaneous incision so that the k-wire can be advanced to a target site prior to inserting the adjustable rod structure over the k-wire through a cannulation of the probe, such as that shown in FIG. 20. In this way, the k-wire can be used to aid in guiding adjustable rod structure to the target site.

In other embodiments, the method can be complemented by the use of the endoscopic access system following retraction of the rods and in some variants, following insertion of rings into the portal created through retraction. Initially, the frame of the system is secured to the retractor. To properly secure the frame, the scope holder is aligned over the portal. In this manner, the probe is aligned so that its axis extends through a volume within the profile of the retracted rods. If necessary, the screw of the support holder is then actuated to lower the probe and accompanying lens into the portal. Actuation of the screw can be achieved using any means known in the art. For example, the screw can be turned counterclockwise to allow free movement of the probe then turned clockwise to secure the screw to the probe. In another example, the actuation of the screw itself can adjust the position of the probe. During actuation, a surgeon viewing the outlet at the lens from an eye piece of the system uses the current position of the lens to determine whether further adjustment of the probe is necessary. Through the lens, the surgeon can identify whether any adjustments to the position of the adjustable rod structure are necessary or, during the placement of an implant or other surgical procedure, the surgeon can refine his or her approach for implant placement. In some variants, the frame of the endoscopic access system is secured to a structure other than the retractor. For example, it can be secured to a table, a robot, or any other physical construction that provides stability.

In still further embodiments, the method can be complemented through the use of a robot as described above. The robot can be incorporated into the methods described herein at various steps and in varying degrees. For example, the robot can assist a surgeon in the placement of the adjustable rod structure. To do so, the surgeon will operate the robot to assist in advancing the rod structure rather than doing so solely using manual means, i.e. so that the procedure is semi-autonomous. Many variants of this approach are contemplated. In one, the surgeon will experience physical feedback if the advancement of the rod structure approaches too closely to nerves or a predetermined surgical boundary in a three-dimensional space. This is made possible in part by a tracking device connected to the rod structure which communicates with the robot to determine, and update, a location of the rod structure during advancement. In another example, similar principles are used to advance an implant into a target anatomical site.

Kits

In another aspect, the elements of the above apparatuses and systems can also be included as part of a kit. In one embodiment, a kit includes three rods (e.g., FIGS. 8A-8B), a ring and a retractor. In a variant, the kit can include more than three rods, more than one ring and a retractor. In another variant, the kit can include at least one rod of a first size and a second rod of a second size. In yet another variant, the kit can include at least one ring of a first size and at least one ring of a second size. Rods included in the kit can vary according to any combination of the following variables: length, profile (i.e., cross-sectional shape), shape of distal end (e.g., flat, curved for conformance with vertebral surface, conical, bullet shaped, pointed or otherwise tapered (e.g., forming part of a pointed tip in combination with other rods)), taper along length, diameter, cannulations, and materials, including whether composite materials are used, among others. Rings included in the kit can vary by length, profile, whether one end surface is arcuate, diameter, wall thickness (and similarly diameter of opening through ring), external features on the ring, openings within the thickness of the ring, materials and number of layers of material on the ring. In one example of this embodiment, a kit includes three or more rods of a first size, three or more rods of a second size and three or more rods of a third size. The kit also includes a plurality of rings having at least a first diameter and a length so that at least one ring is approximately 10 mm longer than at least one other ring. The kit further includes a retractor with arms configured to hold at least three rods in a releasably engagable manner. In another example, the kit includes at least three rods and at least five rings, each having a length different from at least one other ring by at least 10 mm, along with a retractor. In yet another example, the kit includes a first rod 30 mm long, a second rod 100 mm long, a third rod 170 mm long, a ring 30 mm long, a ring 40 mm long and a ring 50 mm long, along with a retractor.

In another embodiment, the kit can include at least three rods, at least one probe, at least one ring and at least one retractor. In any one of the above embodiments, the kit can further include equipment for neuro-monitoring including an electrode such as wire or cable for transmission of signals, a sensor and an interface for a user. The kit can also include k or y-wire. Other embodiments further include lighting adapted for use with the physical scale of the adjustable rod structure, such as those incorporated by reference above. In still other embodiments, the kit can include an endoscopic access system, a robot, a navigation system or any combination of these.

Navigation System

In some embodiments, the apparatuses, systems and methods can also include a navigation system. In its most basic form the navigation system includes a power source, a controller with an interface to monitor advancement of the adjustable rod structure, a connective element to connect the controller with a sensor, and a sensor adapted to monitor the location of a probe or rod it is connected to. The connective element is wireless but can also include a physical wire attached to the sensor. The controller and accompanying monitoring equipment are positioned outside of the body throughout the procedure. In one example, the interface included with the monitoring equipment uses LEDs for monitoring the position of the probe and/or rods. The interface is configured so that the intended anatomical location remains visible throughout the procedure. An exemplary navigation system of the variety described above that can be employed in conjunction with the methods described herein is the SpineMask® Non-Invasive Tracker by Stryker® described in U.S. Pat. Pub. No. 2015/0327948, the disclosure of which is hereby incorporated by reference herein in its entirety. The navigation system is configured so that when the adjustable rod structure is inserted into the patient, the location and trajectory of the rods can be monitored during advancement and adjusted prior to reaching a final position adjacent to an anatomical location associated with surgery. Through this approach, the need for adjustment after the rods are fully inserted into the body is either eliminated or minimized. In a variant, two or more sensors can be placed on one or more of the rods and probe of the adjustable rod structure.

In another variant, a tracker as described above for use as part of a robotic device can be incorporated into the navigation system. The tracker can be physically placed on the object to be tracked, such as the adjustable rod structure or an implant.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for implantation of spinal implants comprising:
a retractor including a frame and first, second and third arms secured thereto, at least one of the first, second and third arms movable in predetermined increments relative to the frame; and
first, second and third rods each secured to one of the arms, the first, second and third rods having an I-shaped cross-section over a portion of a length of each rod and a partially convex perimeter,
wherein the first, second and third rods are movable between a first position and a second position, and
wherein the first, second and third rods are moved from the first position to the second position when one or more of the first, second and third arms is moved away from the other arms by a predetermined amount.

2. The system of claim 1, wherein the cross-sectional shape of each of the rods tapers from a proximal end of the rod to a distal portion of the rod, decreasing in cross-sectional size from the proximal end.

3. The system of claim 1, wherein the first, second and third rods together in the first position form a tapered shape toward a distal tip, the tapered shape comprised of a tapered end on each of the first, second and third rods.

4. The system of claim 1, wherein the first, second and third rods are in the first position when each of the rods is prevented from being moved further inward by one of an arm secured to another rod, another rod, or a structure disposed in between the rods.

5. The system of claim 1, wherein the first, second and third rods are parallel to one another in the first position and in the second position.

6. The system of claim 1, further comprising a probe disposed between the first, second and third rods, the probe removable from in between the first, second and third rods when the rods are in the first position.

7. The system of claim 6, wherein the probe includes first, second and third indentations to receive the first, second and third rods, respectively.

8. The system of claim 1, wherein any one of the first, second and third rods is movable relative to any other of the first, second and third rods through actuation of an arm secured to the rod.

9. The system of claim 8, wherein the first, second and third arms are movable in a linear manner.

10. The system of claim 8, wherein the first, second and third rods are individually rotatable relative to the frame such that rotation of one of the rods alters an orientation of the rotated one of the rods relative to the other rods.

11. The system of claim 1, wherein each of the rods is adjustable in a direction of a longitudinal axis of the rod when attached to a respective arm of the retractor.

12. The system of claim 1, wherein the partially convex perimeter of one of the first, second or third rods is on a flange of the I-shaped cross-section.

13. A retraction system comprising:
first, second and third rods movable between a first position and a second position with respect to each other;
a probe disposed between the first, second and third rods; and
a retractor attached to the first, second and third rods and configured to move the rods between the first and second positions in predetermined increments,
wherein the probe includes first, second and third grooves each extending along a length of the probe with the first rod disposed within the first groove, the second rod disposed within the second groove and the third rod disposed within the third groove when the rods are in the first position, and
wherein the probe is removable from in between the first, second and third rods when the first, second and third rods are in the first position.

14. The system of claim 13, wherein the first, second and third rods are I-shaped.

15. The system of claim 13, wherein the probe tapers to a tip at a distal end of the probe.

16. The system of claim 15, wherein the first, second and third rods taper to a distal end of the respective first, second and third rods remote from the retractor, the distal ends of each of the rods being closer to the retractor than the distal end of the probe.

17. The system of claim 15, wherein the first, second and third rods in the first position with the probe disposed therebetween form a conical tip remote from the retractor.

18. The system of claim 13, wherein the probe is cannulated.

19. The system of claim 13, wherein the first, second and third rods are flexible under loads borne within a human body.

* * * * *